US010239058B2

(12) United States Patent
Lavieu et al.

(10) Patent No.: US 10,239,058 B2
(45) Date of Patent: Mar. 26, 2019

(54) METHODS, SYSTEMS AND DEVICES FOR SELECTION AND GENERATION OF GENOME EDITED CLONES

(71) Applicant: Berkeley Lights, Inc., Emeryville, CA (US)

(72) Inventors: Gregory G. Lavieu, Vitry sur Seine (FR); Annamaria Mocciaro, San Francisco, CA (US); Xiao Guan Radstrom, San Rafael, CA (US); Jason M. McEwen, El Cerrito, CA (US); Magali Soumillon, Berkeley, CA (US); J. Tanner Nevill, El Cerrito, CA (US); Volker L. S. Kurz, Oakland, CA (US); Patricia A. Dyck, San Francisco, CA (US); Ravi K. Ramenani, Fremont, CA (US)

(73) Assignee: Berkeley Lights, Inc., Emeryville, CA (US)

( * ) Notice: Subject to any disclaimer, the term of this patent is extended or adjusted under 35 U.S.C. 154(b) by 0 days.

(21) Appl. No.: 15/802,174

(22) Filed: Nov. 2, 2017

(65) Prior Publication Data
US 2018/0147576 A1 May 31, 2018

Related U.S. Application Data

(63) Continuation of application No. PCT/US2017/022518, filed on Mar. 15, 2017.

(60) Provisional application No. 62/351,846, filed on Jun. 17, 2016, provisional application No. 62/309,301, filed on Mar. 16, 2016.

(51) Int. Cl.
| G01N 15/00 | (2006.01) |
| B01L 3/00 | (2006.01) |
| C12M 3/06 | (2006.01) |
| C12N 15/10 | (2006.01) |
| G01N 15/10 | (2006.01) |
| B03C 7/02 | (2006.01) |
| G01N 15/02 | (2006.01) |

(52) U.S. Cl.
CPC ... B01L 3/502761 (2013.01); B01L 3/502792 (2013.01); C12M 23/16 (2013.01); C12N 15/1003 (2013.01); C12N 15/1024 (2013.01); C12N 15/1086 (2013.01); G01N 15/10 (2013.01); B01L 2200/0647 (2013.01); B01L 2200/0668 (2013.01); B01L 2300/0816 (2013.01); B01L 2300/0864 (2013.01); B01L 2400/0424 (2013.01); B01L 2400/0427 (2013.01); C12N 2310/00 (2013.01); C12N 2510/00 (2013.01); G01N 2015/0288 (2013.01); G01N 2015/1081 (2013.01)

(58) Field of Classification Search
CPC .. B01L 3/502761; B01L 3/5027; B01L 3/502; B01L 3/50; B01L 3/502792; C12N 15/1003; C12N 15/10; C12N 15/09; C12N 15/1024
USPC .......................................... 422/504, 500, 50
See application file for complete search history.

(56) References Cited

U.S. PATENT DOCUMENTS

| 6,294,063 | B1 | 9/2001 | Becker et al. |
| 6,942,776 | B2 | 9/2005 | Medoro |
| 7,090,759 | B1 | 8/2006 | Seul |
| 8,921,041 | B2 | 12/2014 | Wang et al. |
| 2003/0008364 | A1 | 1/2003 | Wang et al. |
| 2004/0072278 | A1* | 4/2004 | Chou ................ B01L 3/502761 435/29 |
| 2004/0191789 | A1 | 9/2004 | Manaresi et al. |
| 2005/0112548 | A1 | 5/2005 | Segawa et al. |
| 2005/0129581 | A1 | 6/2005 | McBride et al. |
| 2005/0175981 | A1 | 8/2005 | Voldman et al. |
| 2006/0091015 | A1 | 5/2006 | Lau |
| 2007/0095669 | A1 | 5/2007 | Lau et al. |
| 2008/0302732 | A1 | 12/2008 | Soh et al. |
| 2009/0170186 | A1 | 7/2009 | Wu et al. |
| 2010/0003666 | A1 | 1/2010 | Lee et al. |
| 2010/0101960 | A1 | 4/2010 | Ohta et al. |
| 2011/0117634 | A1 | 5/2011 | Halamish et al. |

(Continued)

FOREIGN PATENT DOCUMENTS

WO   WO 2017/123978   7/2017

OTHER PUBLICATIONS

Cho et al, Targeted genome engineering in human cells with the Cas9 RNA-guided endonuclease, Nautre Biotechnology, vol. 31, No. 3, Mar. 2013, pp. 230-232. (Year: 2013).*
Cho et al., "Targeted Genome Engineering in Human Cells with the Cas9 RNA-Guided Endonuclease," Nat Biotechnol., 2013, 31(3):230-2.
Cong et al., "Multiplex Genome Engineering Using CRISPR/Cas Systems," Science, 2013, 339:819-23.

(Continued)

Primary Examiner — Christine T Mui
(74) Attorney, Agent, or Firm — McNeill Baur PLLC

(57) ABSTRACT

Methods are described herein for isolating clonal populations of cells having a defined genetic modification. The methods are performed, at least in part, in a microfluidic device comprising one or more sequestration pens. The methods include the steps of: maintaining individual cells (or precursors thereof) that have undergone a genomic editing process in corresponding sequestration pens of a microfluidic device; expanding the individual cells into respective clonal populations of cells; and detecting, in one or more cells of each clonal population, the presence of a first nucleic acid sequence that is indicative of the presence of an on-target genome edit in the clonal population of cells. Also described are methods of performing genome editing within a microfluidic device, and compositions comprising one or more clonal populations of cells generated according to the methods disclosed herein.

30 Claims, 21 Drawing Sheets

Specification includes a Sequence Listing.

(56) References Cited

U.S. PATENT DOCUMENTS

| | | |
|---|---|---|
| 2012/0118740 A1 | 5/2012 | Garcia et al. |
| 2012/0208266 A1 | 8/2012 | Bookbinder et al. |
| 2012/0325665 A1 | 12/2012 | Chiou et al. |
| 2013/0118905 A1 | 5/2013 | Morimoto et al. |
| 2013/0171628 A1 | 7/2013 | Di Carlo et al. |
| 2013/0190212 A1 | 7/2013 | Handique et al. |
| 2013/0204076 A1 | 8/2013 | Han et al. |
| 2013/0288065 A1 | 10/2013 | Chen et al. |
| 2014/0017791 A1 | 1/2014 | Chapman et al. |
| 2014/0116881 A1 | 5/2014 | Chapman et al. |
| 2015/0151298 A1* | 6/2015 | Hobbs ............... B01L 3/502761 435/7.1 |
| 2015/0151307 A1 | 6/2015 | Breinlinger et al. |
| 2015/0165436 A1 | 6/2015 | Chapman et al. |
| 2015/0166326 A1 | 6/2015 | Chapman et al. |
| 2015/0306599 A1 | 10/2015 | Khandros et al. |
| 2016/0158757 A1 | 6/2016 | Breinlinger et al. |
| 2016/0171686 A1 | 6/2016 | Du et al. |
| 2016/0184821 A1 | 6/2016 | Hobbs et al. |
| 2016/0193604 A1 | 7/2016 | McFarland et al. |
| 2016/0199837 A1 | 7/2016 | Breinlinger et al. |
| 2016/0252495 A1 | 9/2016 | Ricicova et al. |
| 2016/0312165 A1 | 10/2016 | Lowe, Jr. et al. |
| 2017/0224734 A1 | 8/2017 | Chapman et al. |

OTHER PUBLICATIONS

Han et al., "CRISPR-Cas9 Delivery to Hard-to-Transfect Cells via Membrane Deformation," Sci. Adv., 2015, 1(7):1-8.
He, et al., "Knock-in of Large Reporter Genes in Human Cells via CRISPR/Cas9-Induced Homology-Dependent and Independent DNA Repair," Nucleic Acids Research, 2016, 44(9):e85.
Hultquist et al., "A Cas9 Ribonucleoprotein Platform for Functional Genetic Studies of HIV-Host Interactions in Primary Human T Cells," Cell Reports, 2016, 17(5):1438-52.
International Search Report for PCT/US2017/022518, dated Aug. 7, 2017, 19 pages.
Jinek et al., "RNA-Programmed Genome Editing in Human Cells," eLife, 2013, 2:e00471.
Liang et al., "Rapid and Highly Efficient Mammalian Cell Engineering via Cas9 Protein Transfection," J. Biotechnol., 2015, 208:44-53.
Mali et al., "RNA-Guided Human Genome Engineering via Cas9," Science, 2013, 339:823-26.
Peterson et al., "Long-Term Multilineage Engraftment of Autologous Genome-Edited Hematopoietic Stem Cells in Nonhuman Primates," Blood, 2016, 127(20):2416-26.
Poirot et al., "Multiplex Genome Edited T-Cell Manufacturing Platform for "Off-the-Shelf" Adoptive T-Cell Immunotherapies," Cancer Res, 2015, 37 pages (published as Cancer Res, 2015, 75(18):3853-64).
Schumann et al., "Generation of Knock-In Primary Human T Cells using Cas9 Ribonucleoproteins," PNAS, 2015, 112(33):10437-42.
Wickham et al., "Targeted Adenovirus-Mediated Gene Delivery to T Cells via CD3," J Virology, 1997, 71(10):7663-69.
Chiou et al., "Massively Parallel Manipulation of Single Cells and Microparticles Using Optical Images," Nature, 2005, 436:370-372.
Chiou, "Massively parallel optical manipulation of cells, micro- and nano-particles on optoelectronic devices," Dissertation, University of California at Berkeley, 2005 (147 pages).
Chung et al., "DNA-Tethered Membranes Formed by Giant Vesicle Rupture," Journal of Structural Biology, 2009, 168:190-199.
Di Carlo et al., "Dynamic Single Cell Analysis for Quantitative Biology," Analytical Chemistry, 2006, 7918-7925.
Gel et al., "Microorifice-Based High-Yield Cell Fusion on Microfluidic Chip: Electrofusion of Selected Pairs and Fusant Viability," IEEE Transactions on Nanobioscience, 2009, 8(4):300-305.
Hsu et al., "Sorting of Differentiated Neurons using Phototransistor-Based Optoelectronic Tweezers for Cell Replacement Therapy of Neurodegenerative Diseases," IEEE Conference on Transducers, 2009, 4 pages.
Hu et al., "A High-Throughput Dielectrophoresis-Based Cell Electrofusion Microfluidic Device," Electrophoresis, 2011, 32:2488-2495.
Hung et al., "Continuous Perfusion Microfluidic Cell Culture Array for High-Throughput Cell-Based Assays," Biotech and Bioengineering, 2004, 89(1):1-8.
Lin et al., "An Optically Induced Cell Lysis Device Using Dielectrophoresis," Applied Physics Letters, 2009, 94:033901.
Lowe, Jr., "Controlled Vapor Deposition of Azide-Terminated Siloxane Monolayers: A Platform for Tailoring Oxide Surfaces," Dissertation, Stanford University, Aug. 2011, 152 pages.
Lowe, Jr. et al., "Deposition of Dense Siloxane Monolayers from Water and Trimethoxyorganosilane Vapor," Langmuir, 2011, 27:9928-9935.
Nevill et al., "Integrated Microfluidic Cell Culture and Lysis on a Chip," Lab on a Chip, 2007, 7:1689-95.
Poirot et al., "Multiplex Genome Edited T-Cell Manufacturing Platform for "off-the-shelf" Adoptive T-Cell Immunotherapies," Cancer Research, 2015, 75(12), 37 pages.
Somaweera et al., "Generation of a Chemical Gradient Across an Array of 256 Cell Cultures in a Single Chip," Analyst, 2013, 138(19):5566-5571.
Valley et al, "Optoelectronic Tweezers as a Tool for Parallel Single-Cell Manipulation and Stimulation," IEEE Transactions on Biomedical Circuits and Systems, 2009, 3(6):424-30.
Yi et al., "Microfluidics Technology for Manipulation and Analysis of Biological Cells," Analytica Chimica Acta, 2006, 560:1-23.

* cited by examiner ly modified cells in a microfluidic device having a at least one sequestration pen. The

```
                           SEQUENCE LISTING

<160> NUMBER OF SEQ ID NOS: 6

<210> SEQ ID NO 1
<211> LENGTH: 23
<212> TYPE: DNA
<213> ORGANISM: Artificial Sequence
<220> FEATURE:
<223> OTHER INFORMATION: Guide RNA targeting endogenous ARF1 sequence

<400> SEQUENCE: 1
actggctgtc caatcagctc cgg                                              23

<210> SEQ ID NO 2
<211> LENGTH: 876
<212> TYPE: DNA
<213> ORGANISM: Artificial Sequence
<220> FEATURE:
<223> OTHER INFORMATION: Donor template DNA comprising a portion of ARF1
      fused in-frame with an insertion encoding Green Fluorescence
      Protein (GFP)

<400> SEQUENCE: 2
ctgcactcac tacgccacag gaactggtac attcaggcca cctgcgccac cagcggcgac      60
gggctctatg aaggactgga ctggctgtcc aatcaactac gaaaccagaa gggatcgtca     120
ggtcgggatc caggctcagg ttctggagtg agcaagggcg aggagctgtt caccggggtg     180
gtgcccatcc tggtcgagct ggacggcgac gtaaacggcc acaagttcag cgtgtccggc     240
gagggcgagg gcgatgccac ctacggcaag ctgaccctga agttcatctg caccaccggc     300
aagctgcccg tgccctggcc caccctcgtg accaccctga cctacggcgt gcagtgcttc     360
agccgctacc ccgaccacat gaagcagcac gacttcttca agtccgccat gcccgaaggc     420
tacgtccagg agcgcaccat cttcttcaag gacgacggca actacaagac ccgcgccgag     480
gtgaagttcg agggcgacac cctggtgaac cgcatcgagc tgaagggcat cgacttcaag     540
gaggacggca acatcctggg gcacaagctg gagtacaact acaacagcca caacgtctat     600
atcatggccg acaagcagaa gaacggcatc aaggtgaact tcaagatccg ccacaacatc     660
gaggacggca gcgtgcagct cgccgaccac taccagcaga cacccccat cggcgacggc      720 cccgtgctgc tgcccgacaa ccactacctg agcacccagt ccgccctgag caaagacccc     780
aacgagaagc gcgatcacat ggtcctgctg gagttcgtga ccgccgccgg gatcactctc     840
ggcatggacg agctgtacaa gtaggcggcc gcgact                               876

<210> SEQ ID NO 3
<211> LENGTH: 24
<212> TYPE: DNA
<213> ORGANISM: Artificial Sequence
<220> FEATURE:
<223> OTHER INFORMATION: Forward primer F1 designed to amplify a region
      of ARF1 that lacks a GFP insert

<400> SEQUENCE: 3
acctccccaa cgccatgaat gcgg                                             24

<210> SEQ ID NO 4
<211> LENGTH: 18
```

```
<212> TYPE: DNA
<213> ORGANISM: Artificial Sequence
<220> FEATURE:
<223> OTHER INFORMATION: Reverse primer R1 designed to amplify a region
      of ARF1 that lacks a GFP insert

<400> SEQUENCE: 4
tgctaggcgg ggtctccc                                                    18

<210> SEQ ID NO 5
<211> LENGTH: 24
<212> TYPE: DNA
<213> ORGANISM: Artificial Sequence
<220> FEATURE:
<223> OTHER INFORMATION: Forward primer F2 designed to amplify the first
      100 bps of an ARF1 allele having a GFP-encoding nucleic acid
      inserted therein

<400> SEQUENCE: 5
acctccccaa cgccatgaat gcgg                                             24

<210> SEQ ID NO 6
<211> LENGTH: 21
<212> TYPE: DNA
<213> ORGANISM: Artificial Sequence
<220> FEATURE:
<223> OTHER INFORMATION: Reverse primer R2 designed to amplify the first
      100 bps of an ARF1 allele having a GFP-encoding nucleic acid
      inserted therein

<400> SEQUENCE: 6
gtggcatcgc cctcgccctc g                                                21
```

METHODS, SYSTEMS AND DEVICES FOR SELECTION AND GENERATION OF GENOME EDITED CLONES

CROSS REFERENCE TO RELATED APPLICATIONS

This application is a continuation application of PCT/US2017/022518, filed on Mar. 15, 2017, which claims the benefit under 35 U.S.C. § 119 of U.S. Patent Application No. 62/351,846, filed on Jun. 17, 2016, and U.S. Patent Application No. 62/309,301, filed on Mar. 16, 2016, the entire disclosure of each of which is incorporated herein by reference.

REFERENCE TO SEQUENCE LISTING SUBMITTED AS A TEXT FILE VIA EFS-WEB

A sequence listing is submitted concurrently with the specification as an ASCII formatted text file via EFS-Web, with a file name of "2017-11-02_01149-0005-00US_SL_ST25.txt", a creation date of Nov. 2, 2017, and a size of 3294 bytes. The sequence listing filed via EFS-Web is part of the specification and is hereby incorporated by reference in its entirety.

FIELD

The field generally relates to methods, systems and devices for performing genome editing on a population of cells.

BACKGROUND

Genome modification technologies have been used for decades to study gene function. Over the years, the field has progressively developed tools that enable greater and greater target specificity. Transposable elements offered one of the first means of stably altering genome structure, but their target site specificity is typically poor, allowing them to integrate at many different locations within a single genome. To achieve greater targeting accuracy and fewer targeting events, "targeted nucleases" were developed. Early targeted nucleases were formed by fusing the site-specific DNA-binding domains of transcription factors with the endonuclease domains of restriction enzymes. Examples of such targeted nucleases include the Zinc Finger Nucleases (ZFNs) and Transcriptional Activator-Like Effector Nucleases (TALENS). By changing the DNA-binding domain, the target specificity of such targeted nucleases could be selectively modified.

A third, most recently developed technology is based on the prokaryotic Clustered Regularly Interspersed Short Palindromic Repeat (CRISPR)-CRISPR associated (Cas) system. Found in bacteria and archaea, CRISPR/Cas functions as an adaptive immune system in which a "programmable endonuclease" associates with small RNAs derived from CRISPR transcripts. The small RNAs direct the programmable endonuclease to complementary DNA sequences, typically found in infectious agents such as bacteriophage, which are then cleaved. To be cleaved, a target site must not only be complementary to the CRISPR RNA, but also must be positioned adjacent to a short sequence motif (the Protospacer Adjacent Motif or "PAM") that is recognized by the programmable endonuclease. In 2013, it was discovered that a simplified version of the CRISPR/Cas system consisting of a Cas9 endonuclease and a single RNA molecule (referred to as a guide RNA or "gRNA") could be used to induce targeted nucleolytic cleavage of endogenous genomic sites in mammalian cells. Cong et al. (2013), Multiplex genome engineering using CRISPR/Cas systems, Science 339, 819-823; Mali et al. (2013), RNA-guided human genome engineering via Cas9, Science 339, 823-826; Jinek et al. (2013), RNA-programmed genome editing in human cells, eLife 2, e00471. The relative ease of programming the Cas9 nuclease with short gRNAs specifically targeted to individual loci has led to its rapid adoption as the method of choice for genome editing.

Following nucleolytic cleavage by targeted endonucleases, endogenous cellular DNA repair pathways are activated. DNA breaks are generally repaired via one of two major pathways referred to as non-homologous end-joining (NHEJ) and homology-directed repair (HDR). In NHEJ, double-strand breaks are repaired by religation of the cleaved ends without the involvement of any additional donor or template DNA. This repair pathway is error prone, resulting in insertions and/or deletions (indels) of various sizes at the site of the break. Thus, the most straightforward form of gene editing relies upon indel-mediated disruption of gene function; for example, the introduction of frameshift mutations in the coding sequence of a gene. HDR-mediated mechanisms afford the opportunity to edit genomic sites in a more precise manner by providing donor DNA as a template for repair. While the sister chromosome is naturally available to serve as the donor, exogenously introduced DNA can function as a donor template, particularly in the context of an induced double-strand break. The exogenous donor template allows for the replacement of endogenous nucleotides with any desired sequence. Using this approach, a mutant gene can be converted to its wild-type counterpart, or vice versa.

Although genome modification/editing technologies have become excellent tools for introducing precise, targeted alterations in a genome, the problems of NHEJ and off-target modifications still exist. Moreover, identifying NHEJ and off-target modifications can be costly and time consuming. The present disclosure addresses, among other things, these and other related problems that exist in current genome modification/editing technologies.

SUMMARY

In a first aspect, a method is disclosed for generating a clonal population of genetically modified cells in a microfluidic device having a at least one sequestration pen. The microfluidic device can include a plurality of sequestration pens. The method can include: maintaining a first cell in a first sequestration pen; expanding the first cell into a clonal population of cells; and detecting, in one or more (but not all) cells of the clonal population of cells, the presence of a first nucleic acid sequence, wherein the first nucleic acid sequence indicates the presence of an on-target genome edit in the clonal population of cells. In some embodiments, the first cell may be a mammalian cell, such as a cell derived from a human, ape, monkey, rat, mouse, hamster, guinea pig, cow, pig, sheep, horse, dog, or cat. In some embodiments, the first cell can be an immunological cell, such as a T cell, a B cell, an NK cell, a macrophage, or a precursor thereof. In some embodiments, the first cell can be a stem cell, such as embryonic stem cell, a mesenchymal stem cell, an umbilical vein mesenchymal stem cell, an induced pluripotent stem cell (iPSC), a hematopoietic stem cell, an adipose-derived stem cell, a gingival stem cell, a renal stem cell, or a neural stem cell. In some embodiments, the first cell may be a progenitor cell, such as osteochondroprogenitor cell, a myofibroblast, a dermal fibroblast, or an endothelial progenitor cell.

In some embodiments, the method includes contacting the first cell with a genome editing biomolecule, and introducing the first cell into the microfluidic device. The genome editing biomolecule can comprise a donor template nucleic acid molecule. Alternatively, the method can further include contacting the first cell with a donor template nucleic acid molecule that is distinct from the genome editing biomolecule. The donor template nucleic acid molecule can include all or part of the first nucleic acid sequence. The contacting step(s) can be performed prior to, or after, introducing the first cell into the microfluidic device. The first cell can be selected for transfection based upon one or more characteristics, such as morphology, size, production of a protein of interest, the presence of one or more cell surface markers, and a specific binding interaction with an antibody. The selection can take place prior to loading the first cell into the microfluidic device and/or as part of positioning the first cell in the sequestration pen.

In some embodiments, detecting the first nucleic acid sequence comprises selecting one or more (but not all) daughter cells from the clonal population of cells, and extracting nucleic acid from the one or more selected daughter cells. The nucleic acid can be extracted, for example, in a region of the microfluidic device other than the first sequestration pen or after exporting the one or more daughter cells from the microfluidic device. The extracted nucleic acid can include DNA (e.g., genomic DNA), RNA, or the like. Once extracted, the nucleic acid can be amplified, such as by PCR or whole genome amplification (WGA).

In certain embodiments, the on-target genome edit comprises a deletion of endogenous DNA and/or an insertion of exogenous DNA at a target site in the genome. The insertion can comprise (or encode) at least one of a functional biomolecule, a barcode, and a reporter molecule. For on-target genome edits that include an insertion of exogenous DNA, detecting the presence of the first nucleic acid sequence can include detecting all or part of the insertion.

In certain embodiments, the method can include detecting, in one or more cells of the clonal population of cells, the presence of a second nucleic acid sequence and/or a third nucleic acid sequence. The combination of the first nucleic acid sequence and the second nucleic acid sequence can indicate the presence of the on-target genome edit in the clonal population of cells. The presence of the third nucleic acid sequence can indicate the presence of an off-target genome edit in the clonal population of cells.

In certain embodiments, expanding the first cell into a clonal population of cells further comprises monitoring one or more characteristics of the cells of the clonal population for a period of time. The monitoring can be performed periodically or continuously (e.g., substantially continuously). The monitoring can include identifying changes in the size and/or morphology of the cells in the clonal population. Alternatively, or in addition, the monitoring can include determining the rate of proliferation of the first cell into the clonal population of cells, assessing the production of a protein of interest by the cells in the clonal population, assessing the presence of one or more cell surface markers in the cells in the clonal population, and/or assessing reaction of the cells in the clonal population with an antibody that specifically binds to an antigen of interest.

In some embodiments, at least one surface of the sequestration pen (e.g., an internal surface) is a conditioned surface. The conditioned surface can include covalently-linked molecules, each having a linking group covalently bound to the surface of the sequestration pen (or the portion thereof) and a moiety covalently bound to the linking group. The moieties of the covalently-linked molecules can provide, for example, a layer of organic and/or hydrophilic molecules suitable for maintenance and/or growth of the genome-edited first cell. The moieties can be polymers that comprise polyethylene glycol, saccharides, or amino acids. In certain embodiments, each moiety of a first subset of the covalently-linked molecules is a polymer that comprises amino acids and each moiety of a second subset of the covalently-linked molecules is a polymer that comprises polyethylene glycol or saccharides.

In another aspect, a method is disclosed for performing targeted genome editing within a microfluidic device. The microfluidic device can be configured as described elsewhere herein. The method can include the steps of selecting a first cell for genome editing, positioning the first cell within an editing region of the microfluidic device, and while the first cell is located within the editing region, contacting the first cell with a genome editing biomolecule and allowing the genome editing biomolecule to edit the genome of the first cell at a target site. Contacting the first cell can include permeabilizing the first cell. Permeabilizing the first cell can involve, for example, electroporating or chemically permeabilizing the first cell.

The genome editing biomolecule can comprise a targeting nucleic acid. The targeting biomolecule can comprise DNA or RNA. The genome editing biomolecule can comprise or encode an endonuclease. The endonuclease can be a programmable endonuclease, such as Cas9, Cpf1, or NgAgo. Alternatively, the endonuclease can be a targeted endonuclease, such as a TALEN protein or a Zinc Finger Nuclease (ZFN). The endonuclease can be fused to a cell-penetrating peptide. The genome editing biomolecule can comprise one or more expression cassettes that encode the targeting nucleic acid and/or the endonuclease.

In certain embodiments, the genome editing biomolecule can comprise a viral vector, such as a lentiviral vector or an adenoviral vector. In some embodiments, the lentiviral vector is integrase deficient. In other embodiments, the genome editing biomolecule can be associated with a nanoparticle delivery vehicle. Thus, contacting the first cell with a genome editing biomolecule can comprise contacting the first cell with the nanoparticle delivery vehicle.

In some embodiments, contacting the first cell with a genome editing biomolecule further comprises contacting the first cell with a donor template DNA. The donor template DNA, for example, may be bound to or part of the genome editing biomolecule. Alternatively, the genome editing biomolecule and the donor template DNA may be separate molecular entities. In some embodiments, the donor template DNA may comprise an insertion sequence. Optionally, the insertion sequence can comprise or encode at least one of a functional biomolecule, a barcode sequence, and a reporter molecule.

In another aspect, a composition comprising a clonal population of genetically modified cells is disclosed. The clonal population can be generated by any one of the methods disclosed herein. The composition can include a plurality of clonal populations of genetically modified cells, each generated by any one of the methods disclosed herein. The composition can include at least 1000 genetically modified cells, or at least 10,000 genetically modified cells. The composition can further comprise a pharmaceutically acceptable carrier.

In yet another aspect, a microfluidic device having an editing region is disclosed. The editing region can be configured as described elsewhere herein. For example, the editing region can include a DEP-configuration that supports electroporation of cells. The editing region can include at least one surface that is a conditioned surface. The microfluidic device can further include at least one sequestration pen.

Additional aspects and embodiments are disclosed or otherwise made evident in the detailed description, associated drawings, and claims that follow.

DETAILED DESCRIPTION

Figure 1A:
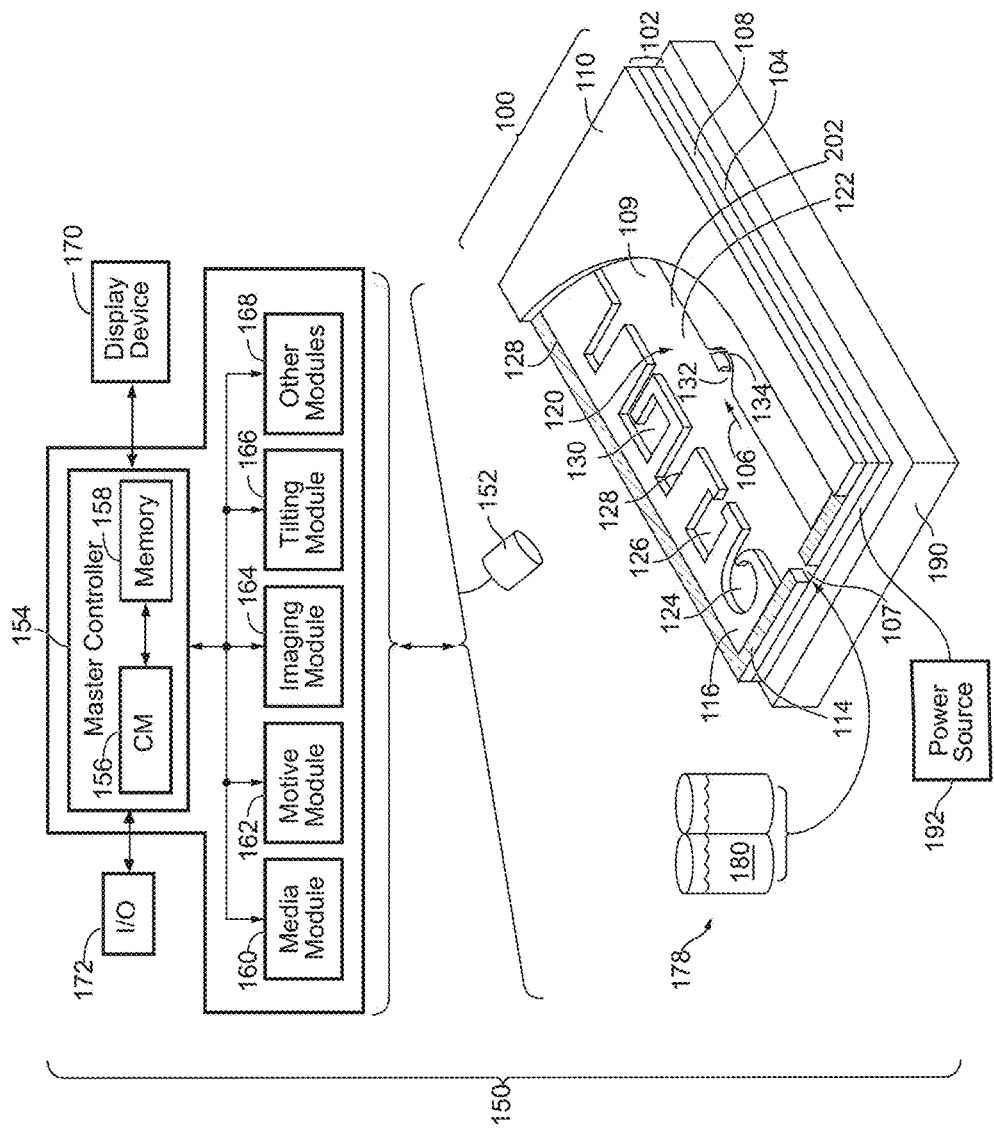
FIG. 1A illustrates an example of a system for use with a microfluidic device and associated control equipment according to some embodiments of the disclosure.

This specification describes exemplary embodiments and applications of the disclosure. The disclosure, however, is not limited to these exemplary embodiments and applications or to the manner in which the exemplary embodiments and applications operate or are described herein. Moreover, the figures may show simplified or partial views, and the dimensions of elements in the figures may be exaggerated or otherwise not in proportion. In addition, as the terms "on," "attached to," "connected to," "coupled to," or similar words are used herein, one element (e.g., a material, a layer, a substrate, etc.) can be "on," "attached to," "connected to," or "coupled to" another element regardless of whether the one element is directly on, attached to, connected to, or coupled to the other element or there are one or more intervening elements between the one element and the other element. Also, unless the context dictates otherwise, directions (e.g., above, below, top, bottom, side, up, down, under, over, upper, lower, horizontal, vertical, "x," "y," "z," etc.), if provided, are relative and provided solely by way of example and for ease of illustration and discussion and not by way of limitation. In addition, where reference is made to a list of elements (e.g., elements a, b, c), such reference is intended to include any one of the listed elements by itself, any combination of less than all of the listed elements, and/or a combination of all of the listed elements. Section divisions in the specification are for ease of review only and do not limit any combination of elements discussed.

Where dimensions of microfluidic features are described as having a width or an area, the dimension typically is described relative to an x-axial and/or y-axial dimension, both of which lie within a plane that is parallel to the substrate and/or cover of the microfluidic device. The height of a microfluidic feature may be described relative to a z-axial direction, which is perpendicular to a plane that is parallel to the substrate and/or cover of the microfluidic device. In some instances, a cross sectional area of a microfluidic feature, such as a channel or a passageway, may be in reference to a x-axial/z-axial, a y-axial/z-axial, or an x-axial/y-axial area.

As used herein, "substantially" means sufficient to work for the intended purpose. The term "substantially" thus allows for minor, insignificant variations from an absolute or perfect state, dimension, measurement, result, or the like such as would be expected by a person of ordinary skill in the field but that do not appreciably affect overall performance. When used with respect to numerical values or parameters or characteristics that can be expressed as numerical values, "substantially" means within ten percent.

The term "ones" means more than one.

As used herein, the term "plurality" can be 2, 3, 4, 5, 6, 7, 8, 9, 10, or more.

As used herein, the term "disposed" encompasses within its meaning "located."

As used herein, a "microfluidic device" or "microfluidic apparatus" is a device that includes one or more discrete microfluidic circuits configured to hold a fluid, each microfluidic circuit comprised of fluidically interconnected circuit elements, including but not limited to region(s), flow path(s), channel(s), chamber(s), and/or pen(s), and at least one port configured to allow the fluid (and, optionally, microobjects suspended in the fluid) to flow into and/or out of the microfluidic device. Typically, a microfluidic circuit of a microfluidic device will include a flow region, which may include a microfluidic channel, and at least one chamber, and will hold a volume of fluid of less than about 1 mL, e.g., less than about 750, 500, 250, 200, 150, 100, 75, 50, 25, 20, 15, 10, 9, 8, 7, 6, 5, 4, 3, or 2 µL. In certain embodiments, the microfluidic circuit holds about 1-2, 1-3, 1-4, 1-5, 2-5, 2-8, 2-10, 2-12, 2-15, 2-20, 5-20, 5-30, 5-40, 5-50, 10-50, 10-75, 10-100, 20-100, 20-150, 20-200, 50-200, 50-250, or 50-300 μL. The microfluidic circuit may be configured to have a first end fluidically connected with a first port (e.g., an inlet) in the microfluidic device and a second end fluidically connected with a second port (e.g., an outlet) in the microfluidic device.

As used herein, a "nanofluidic device" or "nanofluidic apparatus" is a type of microfluidic device having a microfluidic circuit that contains at least one circuit element configured to hold a volume of fluid of less than about 1 μL, e.g., less than about 750, 500, 250, 200, 150, 100, 75, 50, 25, 20, 15, 10, 9, 8, 7, 6, 5, 4, 3, 2, 1 nL or less. A nanofluidic device may comprise a plurality of circuit elements (e.g., at least 2, 3, 4, 5, 6, 7, 8, 9, 10, 15, 20, 25, 50, 75, 100, 150, 200, 250, 300, 400, 500, 600, 700, 800, 900, 1000, 1500, 2000, 2500, 3000, 3500, 4000, 4500, 5000, 6000, 7000, 8000, 9000, 10,000, or more). In certain embodiments, one or more (e.g., all) of the at least one circuit elements is configured to hold a volume of fluid of about 100 pL to 1 nL, 100 pL to 2 nL, 100 pL to 5 nL, 250 pL to 2 nL, 250 pL to 5 nL, 250 pL to 10 nL, 500 pL to 5 nL, 500 pL to 10 nL, 500 pL to 15 nL, 750 pL to 10 nL, 750 pL to 15 nL, 750 pL to 20 nL, 1 to 10 nL, 1 to 15 nL, 1 to 20 nL, 1 to 25 nL, or 1 to 50 nL. In other embodiments, one or more (e.g., all) of the at least one circuit elements are configured to hold a volume of fluid of about 20 nL to 200nL, 100 to 200 nL, 100 to 300 nL, 100 to 400 nL, 100 to 500 nL, 200 to 300 nL, 200 to 400 nL, 200 to 500 nL, 200 to 600 nL, 200 to 700 nL, 250 to 400 nL, 250 to 500 nL, 250 to 600 nL, or 250 to 750 nL.

A "microfluidic channel" or "flow channel" as used herein refers to flow region of a microfluidic device having a length that is significantly longer than both the horizontal and vertical dimensions. For example, the flow channel can be at least 5 times the length of either the horizontal or vertical dimension, e.g., at least 10 times the length, at least 25 times the length, at least 100 times the length, at least 200 times the length, at least 500 times the length, at least 1,000 times the length, at least 5,000 times the length, or longer. In some embodiments, the length of a flow channel is in the range of from about 100,000 microns to about 500,000 microns, including any range therebetween. In some embodiments, the horizontal dimension is in the range of from about 100 microns to about 1000 microns (e.g., about 150 to about 500 microns) and the vertical dimension is in the range of from about 25 microns to about 200 microns, e.g., from about 40 to about 150 microns. It is noted that a flow channel may have a variety of different spatial configurations in a microfluidic device, and thus is not restricted to a perfectly linear element. For example, a flow channel may be, or include one or more sections having, the following configurations: curve, bend, spiral, incline, decline, fork (e.g., multiple different flow paths), and any combination thereof. In addition, a flow channel may have different cross-sectional areas along its path, widening and constricting to provide a desired fluid flow therein. The flow channel may include valves, and the valves may be of any type known in the art of microfluidics. Examples of microfluidic channels that include valves are disclosed in U.S. Pat. Nos. 6,408,878 and 9,227,200, each of which is herein incorporated by reference in its entirety.

As used herein, the term "obstruction" refers generally to a bump or similar type of structure that is sufficiently large so as to partially (but not completely) impede movement of target micro-objects between two different regions or circuit elements in a microfluidic device. The two different regions/circuit elements can be, for example, the connection region and the isolation region of a microfluidic sequestration pen.

As used herein, the term "constriction" refers generally to a narrowing of a width of a circuit element (or an interface between two circuit elements) in a microfluidic device. The constriction can be located, for example, at the interface between the isolation region and the connection region of a microfluidic sequestration pen of the instant disclosure.

As used herein, the term "transparent" refers to a material which allows visible light to pass through without substantially altering the light as is passes through.

As used herein, the term "micro-object" refers generally to any microscopic object that may be isolated and/or manipulated in accordance with the present disclosure. Non-limiting examples of micro-objects include: inanimate micro-objects such as microparticles; microbeads (e.g., polystyrene beads, Luminex™ beads, or the like); magnetic beads; microrods; microwires; quantum dots, and the like; biological micro-objects such as cells; biological organelles; vesicles, or complexes; synthetic vesicles; liposomes (e.g., synthetic or derived from membrane preparations); lipid nanorafts, and the like; or a combination of inanimate micro-objects and biological micro-objects (e.g., microbeads attached to cells, liposome-coated micro-beads, liposome-coated magnetic beads, or the like). Beads may include moieties/molecules covalently or non-covalently attached, such as fluorescent labels, proteins, carbohydrates, antigens, small molecule signaling moieties, or other chemical/biological species capable of use in an assay. Lipid nanorafts have been described, for example, in Ritchie et al. (2009) "Reconstitution of Membrane Proteins in Phospholipid Bilayer Nanodiscs," Methods Enzymol., 464:211-231.

As used herein, the term "cell" is used interchangeably with the term "biological cell." Non-limiting examples of biological cells include eukaryotic cells, plant cells, animal cells, such as mammalian cells, reptilian cells, avian cells, fish cells, or the like, prokaryotic cells, bacterial cells, fungal cells, protozoan cells, or the like, cells dissociated from a tissue, such as muscle, cartilage, fat, skin, liver, lung, neural tissue, and the like, immunological cells, such as T cells, B cells, natural killer cells, macrophages, and the like, embryos (e.g., zygotes), oocytes, ova, sperm cells, hybridomas, cultured cells, cells from a cell line, cancer cells, infected cells, transfected and/or transformed cells, reporter cells, and the like. A mammalian cell can be, for example, from a human, a mouse, a rat, a horse, a goat, a sheep, a cow, a primate, or the like.

A colony of biological cells is "clonal" if all of the living cells in the colony that are capable of reproducing are daughter cells derived from a single parent cell. In certain embodiments, all the daughter cells in a clonal colony are derived from the single parent cell by no more than 10 divisions. In other embodiments, all the daughter cells in a clonal colony are derived from the single parent cell by no more than 14 divisions. In other embodiments, all the daughter cells in a clonal colony are derived from the single parent cell by no more than 17 divisions. In other embodiments, all the daughter cells in a clonal colony are derived from the single parent cell by no more than 20 divisions. The term "clonal cells" refers to cells of the same clonal colony.

As used herein, a "colony" of biological cells refers to 2 or more cells (e.g. about 2 to about 20, about 4 to about 40, about 6 to about 60, about 8 to about 80, about 10 to about 100, about 20 to about 200, about 40 to about 400, about 60 to about 600, about 80 to about 800, about 100 to about 1000, or greater than 1000 cells).

As used herein, the term "maintaining (a) cell(s)" refers to providing an environment comprising both fluidic and gaseous components and, optionally a surface, that provides the conditions necessary to keep the cells viable and/or expanding.

As used herein, the term "expanding" when referring to cells, refers to increasing in cell number.

A "component" of a fluidic medium is any chemical or biochemical molecule present in the medium, including solvent molecules, ions, small molecules, antibiotics, nucleotides and nucleosides, nucleic acids, amino acids, peptides, proteins, sugars, carbohydrates, lipids, fatty acids, cholesterol, metabolites, or the like.

As used herein, "capture moiety" is a chemical or biological species, functionality, or motif that provides a recognition site for a micro-object. A selected class of micro-objects may recognize the in situ-generated capture moiety and may bind or have an affinity for the in situ-generated capture moiety. Non-limiting examples include antigens, antibodies, and cell surface binding motifs.

As used herein, "flowable polymer" is a polymer monomer or macromer that is soluble or dispersible within a fluidic medium (e.g., a pre-polymer solution). The flowable polymer may be input into a microfluidic flow region and flow with other components of a fluidic medium therein.

As used herein, "photoinitiated polymer" refers to a polymer (or a monomeric molecule that can be used to generate the polymer) that upon exposure to light, is capable of crosslinking covalently, forming specific covalent bonds, changing regiochemistry around a rigidified chemical motif, or forming ion pairs which cause a change in physical state, and thereby forming a polymer network. In some instances, a photoinitiated polymer may include a polymer segment bound to one or more chemical moieties capable of crosslinking covalently, forming specific covalent bonds, changing regiochemistry around a rigidified chemical motif, or forming ion pairs which cause a change in physical state. In some instances, a photoinitiated polymer may require a photoactivatable radical initiator to initiate formation of the polymer network (e.g., via polymerization of the polymer).

As used herein, "antibody" refers to an immunoglobulin (Ig) and includes both polyclonal and monoclonal antibodies; primatized (e.g., humanized); murine; mouse-human; mouse-primate; and chimeric; and may be an intact molecule, a fragment thereof (such as scFv, Fv, Fd, Fab, Fab' and F(ab)'2 fragments), or multimers or aggregates of intact molecules and/or fragments; and may occur in nature or be produced, e.g., by immunization, synthesis or genetic engineering. An "antibody fragment," as used herein, refers to fragments, derived from or related to an antibody, which bind antigen and which in some embodiments may be derivatized to exhibit structural features that facilitate clearance and uptake, e.g., by the incorporation of galactose residues. This includes, e.g., F(ab), F(ab)'2, scFv, light chain variable region (VL), heavy chain variable region (VH), and combinations thereof.

As used herein in reference to a fluidic medium, "diffuse" and "diffusion" refer to thermodynamic movement of a component of the fluidic medium down a concentration gradient.

The phrase "flow of a medium" means bulk movement of a fluidic medium primarily due to any mechanism other than diffusion. For example, flow of a medium can involve movement of the fluidic medium from one point to another point due to a pressure differential between the points. Such flow can include a continuous, pulsed, periodic, random, intermittent, or reciprocating flow of the liquid, or any combination thereof. When one fluidic medium flows into another fluidic medium, turbulence and mixing of the media can result.

The phrase "substantially no flow" refers to a rate of flow of a fluidic medium that, averaged over time, is less than the rate of diffusion of components of a material (e.g., an analyte of interest) into or within the fluidic medium. The rate of diffusion of components of such a material can depend on, for example, temperature, the size of the components, and the strength of interactions between the components and the fluidic medium.

As used herein in reference to different regions within a microfluidic device, the phrase "fluidically connected" means that, when the different regions are substantially filled with fluid, such as fluidic media, the fluid in each of the regions is connected so as to form a single body of fluid. This does not mean that the fluids (or fluidic media) in the different regions are necessarily identical in composition. Rather, the fluids in different fluidically connected regions of a microfluidic device can have different compositions (e.g., different concentrations of solutes, such as proteins, carbohydrates, ions, or other molecules) which are in flux as solutes move down their respective concentration gradients and/or fluids flow through the microfluidic device.

As used herein, a "flow path" refers to one or more fluidically connected circuit elements (e.g. channel(s), region(s), chamber(s) and the like) that define, and are subject to, the trajectory of a flow of medium. A flow path is thus an example of a swept region of a microfluidic device. Other circuit elements (e.g., unswept regions) may be fluidically connected with the circuit elements that comprise the flow path without being subject to the flow of medium in the flow path.

As used herein, "isolating a micro-object" confines a micro-object to a defined area within the microfluidic device. The micro-object may still be capable of motion within an in situ-generated capture structure.

A microfluidic (or nanofluidic) device can comprise "swept" regions and "unswept" regions. As used herein, a "swept" region is comprised of one or more fluidically interconnected circuit elements of a microfluidic circuit, each of which experiences a flow of medium when fluid is flowing through the microfluidic circuit. The circuit elements of a swept region can include, for example, regions, channels, and all or parts of chambers. As used herein, an "unswept" region is comprised of one or more fluidically interconnected circuit element of a microfluidic circuit, each of which experiences substantially no flux of fluid when fluid is flowing through the microfluidic circuit. An unswept region can be fluidically connected to a swept region, provided the fluidic connections are structured to enable diffusion but substantially no flow of media between the swept region and the unswept region. The microfluidic device can thus be structured to substantially isolate an unswept region from a flow of medium in a swept region, while enabling substantially only diffusive fluidic communication between the swept region and the unswept region. For example, a flow channel of a micro-fluidic device is an example of a swept region while an isolation region (described in further detail below) of a microfluidic device is an example of an unswept region.

The capability of biological micro-objects (e.g., biological cells) to produce specific biological materials (e.g., proteins, such as antibodies) can be assayed in such a microfluidic device. In a specific embodiment of an assay, sample material comprising biological micro-objects (e.g., cells) to be assayed for production of an analyte of interest can be loaded into a swept region of the microfluidic device. Ones of the biological micro-objects (e.g., mammalian cells, such as human cells) can be selected for particular characteristics and disposed in unswept regions. The remaining sample material can then be flowed out of the swept region and an assay material flowed into the swept region. Because the selected biological micro-objects are in unswept regions, the selected biological micro-objects are not substantially affected by the flowing out of the remaining sample material or the flowing in of the assay material. The selected biological micro-objects can be allowed to produce the analyte of interest, which can diffuse from the unswept regions into the swept region, where the analyte of interest can react with the assay material to produce localized detectable reactions, each of which can be correlated to a particular unswept region. Any unswept region associated with a detected reaction can be analyzed to determine which, if any, of the biological micro-objects in the unswept region are sufficient producers of the analyte of interest.

Microfluidic devices and systems for operating and observing such devices. FIG. 1A illustrates an example of a microfluidic device 100 and a system 150 which can be used generate clonal populations of genetically modified cells. A perspective view of the microfluidic device 100 is shown having a partial cut-away of its cover 110 to provide a partial view into the microfluidic device 100. The microfluidic device 100 generally comprises a microfluidic circuit 120 comprising a flow path 106 through which a fluidic medium 180 can flow, optionally carrying one or more micro-objects (not shown) into and/or through the microfluidic circuit 120. Although a single microfluidic circuit 120 is illustrated in FIG. 1A, suitable microfluidic devices can include a plurality (e.g., 2 or 3) of such microfluidic circuits. Regardless, the microfluidic device 100 can be configured to be a nanofluidic device. As illustrated in FIG. 1A, the microfluidic circuit 120 may include a plurality of microfluidic sequestration pens 124, 126, 128, and 130, where each sequestration pens may have one or more openings in fluidic communication with flow path 106. In some embodiments of the device of FIG. 1A, the sequestration pens may have only a single opening in fluidic communication with the flow path 106. As discussed further below, the microfluidic sequestration pens comprise various features and structures that have been optimized for retaining micro-objects in the microfluidic device, such as microfluidic device 100, even when a medium 180 is flowing through the flow path 106. Before turning to the foregoing, however, a brief description of microfluidic device 100 and system 150 is provided.

As generally illustrated in FIG. 1A, the microfluidic circuit 120 is defined by an enclosure 102. Although the enclosure 102 can be physically structured in different configurations, in the example shown in FIG. 1A the enclosure 102 is depicted as comprising a support structure 104 (e.g., a base), a microfluidic circuit structure 108, and a cover 110. The support structure 104, microfluidic circuit structure 108, and cover 110 can be attached to each other. For example, the microfluidic circuit structure 108 can be disposed on an inner surface 109 of the support structure 104, and the cover 110 can be disposed over the microfluidic circuit structure 108. Together with the support structure 104 and cover 110, the microfluidic circuit structure 108 can define the elements of the microfluidic circuit 120.

The support structure 104 can be at the bottom and the cover 110 at the top of the microfluidic circuit 120 as illustrated in FIG. 1A. Alternatively, the support structure 104 and the cover 110 can be configured in other orientations. For example, the support structure 104 can be at the top and the cover 110 at the bottom of the microfluidic circuit 120. Regardless, there can be one or more ports 107 each comprising a passage into or out of the enclosure 102. Examples of a passage include a valve, a gate, a pass-through hole, or the like. As illustrated, port 107 is a pass-through hole created by a gap in the microfluidic circuit structure 108. However, the port 107 can be situated in other components of the enclosure 102, such as the cover 110. Only one port 107 is illustrated in FIG. 1A but the microfluidic circuit 120 can have two or more ports 107. For example, there can be a first port 107 that functions as an inlet for fluid entering the microfluidic circuit 120, and there can be a second port 107 that functions as an outlet for fluid exiting the microfluidic circuit 120. Whether a port 107 function as an inlet or an outlet can depend upon the direction that fluid flows through flow path 106.

The support structure 104 can comprise one or more electrodes (not shown) and a substrate or a plurality of interconnected substrates. For example, the support structure 104 can comprise one or more semiconductor substrates, each of which is electrically connected to an electrode (e.g., all or a subset of the semiconductor substrates can be electrically connected to a single electrode). The support structure 104 can further comprise a printed circuit board assembly ("PCBA"). For example, the semiconductor substrate(s) can be mounted on a PCBA.

The microfluidic circuit structure 108 can define circuit elements of the microfluidic circuit 120. Such circuit elements can comprise spaces or regions that can be fluidly interconnected when microfluidic circuit 120 is filled with fluid, such as flow regions (which may include or be one or more flow channels), chambers, pens, traps, and the like. In the microfluidic circuit 120 illustrated in FIG. 1A, the microfluidic circuit structure 108 comprises a frame 114 and a microfluidic circuit material 116. The frame 114 can partially or completely enclose the microfluidic circuit material 116. The frame 114 can be, for example, a relatively rigid structure substantially surrounding the microfluidic circuit material 116. For example, the frame 114 can comprise a metal material.

The microfluidic circuit material 116 can be patterned with cavities or the like to define circuit elements and interconnections of the microfluidic circuit 120. The microfluidic circuit material 116 can comprise a flexible material, such as a flexible polymer (e.g. rubber, plastic, elastomer, silicone, polydimethylsiloxane ("PDMS"), or the like), which can be gas permeable. Other examples of materials that can compose microfluidic circuit material 116 include molded glass, an etchable material such as silicone (e.g. photo-patternable silicone or "PPS"), photo-resist (e.g., SU8), or the like. In some embodiments, such materials—and thus the microfluidic circuit material 116—can be rigid and/or substantially impermeable to gas. Regardless, microfluidic circuit material 116 can be disposed on the support structure 104 and inside the frame 114.

The cover 110 can be an integral part of the frame 114 and/or the microfluidic circuit material 116. Alternatively, the cover 110 can be a structurally distinct element, as illustrated in FIG. 1A. The cover 110 can comprise the same or different materials than the frame 114 and/or the microfluidic circuit material 116. Similarly, the support structure 104 can be a separate structure from the frame 114 or microfluidic circuit material 116 as illustrated, or an integral part of the frame 114 or microfluidic circuit material 116. Likewise, the frame 114 and microfluidic circuit material 116 can be separate structures as shown in FIG. 1A or integral portions of the same structure.

In some embodiments, the cover 110 can comprise a rigid material. The rigid material may be glass or a material with similar properties. In some embodiments, the cover 110 can comprise a deformable material. The deformable material can be a polymer, such as PDMS. In some embodiments, the cover 110 can comprise both rigid and deformable materials. For example, one or more portions of cover 110 (e.g., one or more portions positioned over sequestration pens 124, 126, 128, 130) can comprise a deformable material that interfaces with rigid materials of the cover 110. In some embodiments, the cover 110 can further include one or more electrodes. The one or more electrodes can comprise a conductive oxide, such as indium-tin-oxide (ITO), which may be coated on glass or a similarly insulating material. Alternatively, the one or more electrodes can be flexible electrodes, such as single-walled nanotubes, multi-walled nanotubes, nanowires, clusters of electrically conductive nanoparticles, or combinations thereof, embedded in a deformable material, such as a polymer (e.g., PDMS). Flexible electrodes that can be used in microfluidic devices have been described, for example, in U.S. 2012/0325665 (Chiou et al.), the contents of which are incorporated herein by reference. In some embodiments, the cover 110 can be modified (e.g., by conditioning all or part of a surface that faces inward toward the microfluidic circuit 120) to support cell adhesion, viability and/or growth. The modification may include a coating of a synthetic or natural polymer. In some embodiments, the cover 110 and/or the support structure 104 can be transparent to light. The cover 110 may also include at least one material that is gas permeable (e.g., PDMS or PPS).

FIG. 1A also shows a system 150 for operating and controlling microfluidic devices, such as microfluidic device 100. System 150 includes an electrical power source 192, an imaging device (incorporated within imaging module 164), and a tilting device 190 (incorporated within tilting module 166).

The electrical power source 192 can provide electric power to the microfluidic device 100 and/or tilting device 190, providing biasing voltages or currents as needed. The electrical power source 192 can, for example, comprise one or more alternating current (AC) and/or direct current (DC) voltage or current sources. The imaging device (part of imaging module 164, discussed below) can comprise a device, such as a digital camera, for capturing images inside microfluidic circuit 120. In some instances, the imaging device further comprises a detector having a fast frame rate and/or high sensitivity (e.g. for low light applications). The imaging device can also include a mechanism for directing stimulating radiation and/or light beams into the microfluidic circuit 120 and collecting radiation and/or light beams reflected or emitted from the microfluidic circuit 120 (or micro-objects contained therein). The emitted light beams may be in the visible spectrum and may, e.g., include fluorescent emissions. The reflected light beams may include reflected emissions originating from an LED or a wide spectrum lamp, such as a mercury lamp (e.g. a high pressure mercury lamp) or a Xenon arc lamp. As discussed with respect to FIG. 3B, the imaging device may further include a microscope (or an optical train), which may or may not include an eyepiece.

System 150 further comprises a tilting device 190 (part of tilting module 166, discussed below) configured to rotate a microfluidic device 100 about one or more axes of rotation. In some embodiments, the tilting device 190 is configured to support and/or hold the enclosure 102 comprising the microfluidic circuit 120 about at least one axis such that the microfluidic device 100 (and thus the microfluidic circuit 120) can be held in a level orientation (i.e. at 0° relative to x- and y-axes), a vertical orientation (i.e. at 90° relative to the x-axis and/or the y-axis), or any orientation therebetween. The orientation of the microfluidic device 100 (and the microfluidic circuit 120) relative to an axis is referred to herein as the "tilt" of the microfluidic device 100 (and the microfluidic circuit 120). For example, the tilting device 190 can tilt the microfluidic device 100 at 0.1°, 0.2°, 0.3°, 0.4°, 0.5°, 0.6°, 0.7°, 0.8°, 0.9°, 1°, 2°, 3°, 4°, 5°, 10°, 15°, 20°, 25°, 30°, 35°, 40°, 45°, 50°, 55°, 60°, 65°, 70°, 75°, 80°, 90° relative to the x-axis or any degree therebetween. The level orientation (and thus the x- and y-axes) is defined as normal to a vertical axis defined by the force of gravity. The tilting device can also tilt the microfluidic device 100 (and the microfluidic circuit 120) to any degree greater than 90° relative to the x-axis and/or y-axis, or tilt the microfluidic device 100 (and the microfluidic circuit 120) 180° relative to the x-axis or the y-axis in order to fully invert the microfluidic device 100 (and the microfluidic circuit 120). Similarly, in some embodiments, the tilting device 190 tilts the microfluidic device 100 (and the microfluidic circuit 120) about an axis of rotation defined by flow path 106 or some other portion of microfluidic circuit 120.

In some instances, the microfluidic device 100 is tilted into a vertical orientation such that the flow path 106 is positioned above or below one or more sequestration pens. The term "above" as used herein denotes that the flow path 106 is positioned higher than the one or more sequestration pens on a vertical axis defined by the force of gravity (i.e. an object in a sequestration pen above a flow path 106 would have a higher gravitational potential energy than an object in the flow path). The term "below" as used herein denotes that the flow path 106 is positioned lower than the one or more sequestration pens on a vertical axis defined by the force of gravity (i.e. an object in a sequestration pen below a flow path 106 would have a lower gravitational potential energy than an object in the flow path).

In some instances, the tilting device 190 tilts the microfluidic device 100 about an axis that is parallel to the flow path 106. Moreover, the microfluidic device 100 can be tilted to an angle of less than 90° such that the flow path 106 is located above or below one or more sequestration pens without being located directly above or below the sequestration pens. In other instances, the tilting device 190 tilts the microfluidic device 100 about an axis perpendicular to the flow path 106. In still other instances, the tilting device 190 tilts the microfluidic device 100 about an axis that is neither parallel nor perpendicular to the flow path 106.

System 150 can further include a media source 178. The media source 178 (e.g., a container, reservoir, or the like) can comprise multiple sections or containers, each for holding a different fluidic medium 180. Thus, the media source 178 can be a device that is outside of and separate from the microfluidic device 100, as illustrated in FIG. 1A. Alternatively, the media source 178 can be located in whole or in part inside the enclosure 102 of the microfluidic device 100. For example, the media source 178 can comprise reservoirs that are part of the microfluidic device 100.

FIG. 1A also illustrates simplified block diagram depictions of examples of control and monitoring equipment 152 that constitute part of system 150 and can be utilized in conjunction with a microfluidic device 100. As shown, examples of such control and monitoring equipment 152 include a master controller 154 comprising a media module 160 for controlling the media source 178, a motive module 162 for controlling movement and/or selection of micro-objects (not shown) and/or medium (e.g., droplets of medium) in the microfluidic circuit 120, an imaging module 164 for controlling an imaging device (e.g., a camera, microscope, light source or any combination thereof) for capturing images (e.g., digital images), and a tilting module 166 for controlling a tilting device 190. The control equipment 152 can also include other modules 168 for controlling, monitoring, or performing other functions with respect to the microfluidic device 100. As shown, the equipment 152 can further include a display device 170 and an input/output device 172.

The master controller 154 can comprise a control module 156 and a digital memory 158. The control module 156 can comprise, for example, a digital processor configured to operate in accordance with machine executable instructions (e.g., software, firmware, source code, or the like) stored as non-transitory data or signals in the memory 158. Alternatively, or in addition, the control module 156 can comprise hardwired digital circuitry and/or analog circuitry. The media module 160, motive module 162, imaging module 164, tilting module 166, and/or other modules 168 can be similarly configured. Thus, functions, processes acts, actions, or steps of a process discussed herein as being performed with respect to the microfluidic device 100 or any other microfluidic apparatus can be performed by any one or more of the master controller 154, media module 160, motive module 162, imaging module 164, tilting module 166, and/or other modules 168 configured as discussed above. Similarly, the master controller 154, media module 160, motive module 162, imaging module 164, tilting module 166, and/or other modules 168 may be communicatively coupled to transmit and receive data used in any function, process, act, action or step discussed herein.

The media module 160 controls the media source 178. For example, the media module 160 can control the media source 178 to input a selected fluidic medium 180 into the enclosure 102 (e.g., through an inlet port 107). The media module 160 can also control removal of media from the enclosure 102 (e.g., through an outlet port (not shown)). One or more media can thus be selectively input into and removed from the microfluidic circuit 120. The media module 160 can also control the flow of fluidic medium 180 in the flow path 106 inside the microfluidic circuit 120. For example, in some embodiments media module 160 stops the flow of media 180 in the flow path 106 and through the enclosure 102 prior to the tilting module 166 causing the tilting device 190 to tilt the microfluidic device 100 to a desired angle of incline.

The motive module 162 can be configured to control selection, trapping, and movement of micro-objects (not shown) in the microfluidic circuit 120. As discussed below with respect to FIGS. 1B and 1C, the enclosure 102 can comprise a dielectrophoresis (DEP), optoelectronic tweezers (OET) and/or opto-electrowetting (OEW) configuration (not shown in FIG. 1A), and the motive module 162 can control the activation of electrodes and/or transistors (e.g., phototransistors) to select and move micro-objects (not shown) and/or droplets of medium (not shown) in the flow path 106 and/or sequestration pens 124, 126, 128, 130.

The imaging module 164 can control the imaging device. For example, the imaging module 164 can receive and process image data from the imaging device. Image data from the imaging device can comprise any type of information captured by the imaging device (e.g., the presence or absence of micro-objects, droplets of medium, accumulation of label, such as fluorescent label, etc.). Using the information captured by the imaging device, the imaging module 164 can further calculate the position of objects (e.g., micro-objects, droplets of medium) and/or the rate of motion of such objects within the microfluidic device 100.

The tilting module 166 can control the tilting motions of tilting device 190. Alternatively, or in addition, the tilting module 166 can control the tilting rate and timing to optimize transfer of micro-objects to the one or more sequestration pens via gravitational forces. The tilting module 166 is communicatively coupled with the imaging module 164 to receive data describing the motion of micro-objects and/or droplets of medium in the microfluidic circuit 120. Using this data, the tilting module 166 may adjust the tilt of the microfluidic circuit 120 in order to adjust the rate at which micro-objects and/or droplets of medium move in the microfluidic circuit 120. The tilting module 166 may also use this data to iteratively adjust the position of a micro-object and/or droplet of medium in the microfluidic circuit 120.

In the example shown in FIG. 1A, the microfluidic circuit 120 is illustrated as comprising a microfluidic channel 122 and sequestration pens 124, 126, 128, 130. Each pen comprises an opening to channel 122, but otherwise is enclosed such that the pens can substantially isolate micro-objects inside the pen from fluidic medium 180 and/or micro-objects in the flow path 106 of channel 122 or in other pens. The walls of the sequestration pen extend from the inner surface 109 of the base to the inside surface of the cover 110 to provide enclosure. The opening of the pen to the microfluidic channel 122 is oriented at an angle to the flow 106 of fluidic medium 180 such that flow 106 is not directed into the pens. The flow may be tangential or orthogonal to the plane of the opening of the pen. In some instances, pens 124, 126, 128, 130 are configured to physically corral one or more micro-objects within the microfluidic circuit 120. Sequestration pens in accordance with the present disclosure can comprise various shapes, surfaces and features that are optimized for use with DEP, OET, OEW, fluid flow, and/or gravitational forces, as will be discussed and shown in detail below.

The microfluidic circuit 120 may comprise any number of microfluidic sequestration pens. Although five sequestration pens are shown, microfluidic circuit 120 may have fewer or more sequestration pens. As shown, microfluidic sequestration pens 124, 126, 128, and 130 of microfluidic circuit 120 each comprise differing features and shapes which may provide one or more benefits useful in producing clonal cell populations, such as isolating a one genetically modified cell from other genetically modified cells. Growth, analysis, and optionally generation of a genetically modified cell (e.g., by contacting a cell with a genome editing biomolecule under conditions conducive to the formation of a genetically modified cell) may all be performed on an individual basis and, in some embodiments, may be performed on an individual time scale. In some embodiments, the microfluidic circuit 120 comprises a plurality of identical microfluidic sequestration pens.

In some embodiments, the microfluidic circuit 120 comprises a plurality of microfluidic sequestration pens, wherein two or more of the sequestration pens comprise differing structures and/or features which provide differing benefits for generating and analyzing clonal populations of genetically modified cells. One non-limiting example may include expanding a single cell into a clonal colony of cells in one type of pen, while extracting nucleic acid from one or more cells of the clonal colony in another type of pen. In another embodiment, at least one of the sequestration pens can be configured to have electrical contacts suitable for electroporation of cells. Microfluidic devices useful for producing clonal populations of genetically modified cells may include any of the sequestration pens 124, 126, 128, and 130 or variations thereof, and/or may include pens configured like those shown in FIGS. 2B, 2C, 2D,2E and 2F, as discussed below.

In the embodiment illustrated in FIG. 1A, a single channel 122 and flow path 106 is shown. However, other embodiments may contain multiple channels 122, each configured to comprise a flow path 106. The microfluidic circuit 120 further comprises an inlet valve or port 107 in fluid communication with the flow path 106 and fluidic medium 180, whereby fluidic medium 180 can access channel 122 via the inlet port 107. In some instances, the flow path 106 comprises a single path. In some instances, the single path is arranged in a zigzag pattern whereby the flow path 106 travels across the microfluidic device 100 two or more times in alternating directions.

In some instances, microfluidic circuit 120 comprises a plurality of parallel channels 122 and flow paths 106, wherein the fluidic medium 180 within each flow path 106 flows in the same direction. In some instances, the fluidic medium within each flow path 106 flows in at least one of a forward or reverse direction. In some instances, a plurality of sequestration pens is configured (e.g., relative to a channel 122) such that the sequestration pens can be loaded with target micro-objects in parallel.

In some embodiments, microfluidic circuit 120 further comprises one or more micro-object traps 132. The traps 132 are generally formed in a wall forming the boundary of a channel 122, and may be positioned opposite an opening of one or more of the microfluidic sequestration pens 124, 126, 128, 130. In some embodiments, the traps 132 are configured to receive or capture a single micro-object from the flow path 106. In some embodiments, the traps 132 are configured to receive or capture a plurality of micro-objects from the flow path 106. In some instances, the traps 132 comprise a volume approximately equal to the volume of a single target micro-object.

The traps 132 may further comprise an opening which is configured to assist the flow of targeted micro-objects into the traps 132. In some instances, the traps 132 comprise an opening having a height and width that is approximately equal to the dimensions of a single target micro-object, whereby larger micro-objects are prevented from entering into the micro-object trap. The traps 132 may further comprise other features configured to assist in retention of targeted micro-objects within the trap 132. In some instances, the trap 132 is aligned with and situated on the opposite side of a channel 122 relative to the opening of a microfluidic sequestration pen, such that upon tilting the microfluidic device 100 about an axis parallel to the microfluidic channel 122, the trapped micro-object exits the trap 132 at a trajectory that causes the micro-object to fall into the opening of the sequestration pen. In some instances, the trap 132 comprises a side passage 134 that is smaller than the target micro-object in order to facilitate flow through the trap 132 and thereby increase the likelihood of capturing a micro-object in the trap 132.

In some embodiments, dielectrophoretic (DEP) forces are applied across the fluidic medium 180 (e.g., in the flow path and/or in the sequestration pens) via one or more electrodes (not shown) to manipulate, transport, separate and sort micro-objects located therein. For example, in some embodiments, DEP forces are applied to one or more portions of microfluidic circuit 120 in order to transfer a single micro-object from the flow path 106 into a desired microfluidic sequestration pen. In some embodiments, DEP forces are used to prevent a micro-object within a sequestration pen (e.g., sequestration pen 124, 126, 128, or 130) from being displaced therefrom. Further, in some embodiments, DEP forces are used to selectively remove a micro-object from a sequestration pen that was previously collected in accordance with the embodiments of the current disclosure. In some embodiments, the DEP forces comprise optoelectronic tweezer (OET) forces.

In other embodiments, optoelectrowetting (OEW) forces are applied to one or more positions in the support structure 104 (and/or the cover 110) of the microfluidic device 100 (e.g., positions helping to define the flow path and/or the sequestration pens) via one or more electrodes (not shown) to manipulate, transport, separate and sort droplets located in the microfluidic circuit 120. For example, in some embodiments, OEW forces are applied to one or more positions in the support structure 104 (and/or the cover 110) in order to transfer a single droplet from the flow path 106 into a desired microfluidic sequestration pen. In some embodiments, OEW forces are used to prevent a droplet within a sequestration pen (e.g., sequestration pen 124, 126, 128, or 130) from being displaced therefrom. Further, in some embodiments, OEW forces are used to selectively remove a droplet from a sequestration pen that was previously collected in accordance with the embodiments of the current disclosure.

In some embodiments, DEP and/or OEW forces are combined with other forces, such as flow and/or gravitational force, so as to manipulate, transport, separate and sort micro-objects and/or droplets within the microfluidic circuit 120. For example, the enclosure 102 can be tilted (e.g., by tilting device 190) to position the flow path 106 and micro-objects located therein above the microfluidic sequestration pens, and the force of gravity can transport the micro-objects and/or droplets into the pens. In some embodiments, the DEP and/or OEW forces can be applied prior to the other forces. In other embodiments, the DEP and/or OEW forces can be applied after the other forces. In still other instances, the DEP and/or OEW forces can be applied at the same time as the other forces or in an alternating manner with the other forces.

Figure 1B:
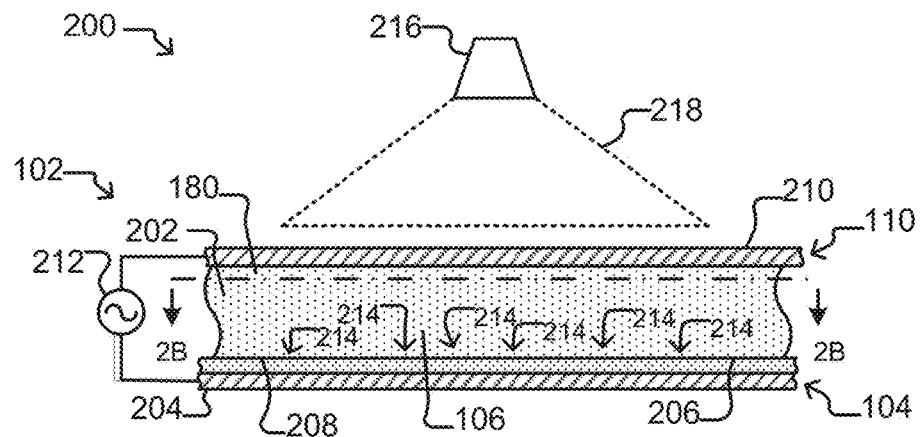
FIGS. 1B and 1C illustrate a microfluidic device according to some embodiments of the disclosure.

FIGS. 1B, 1C, and 2A-2H illustrates various embodiments of microfluidic devices that can be used in the practice of the embodiments of the present disclosure. FIG. 1B depicts an embodiment in which the microfluidic device 200 is configured as an optically-actuated electrokinetic device. A variety of optically-actuated electrokinetic devices are known in the art, including devices having an optoelectronic tweezer (OET) configuration and devices having an optoelectrowetting (OEW) configuration. Examples of suitable OET configurations are illustrated in the following U.S. patent documents, each of which is incorporated herein by reference in its entirety: U.S. Pat. No. RE 44,711 (Wu et al.) (originally issued as U.S. Pat. No. 7,612,355); and U.S. Pat. No. 7,956,339 (Ohta et al.). Examples of OEW configurations are illustrated in U.S. Pat. No. 6,958,132 (Chiou et al.) and U.S. Patent Application Publication No. 2012/0024708 (Chiou et al.), both of which are incorporated by reference herein in their entirety. Yet another example of an optically-actuated electrokinetic device includes a combined OET/OEW configuration, examples of which are shown in U.S. Patent Publication Nos. 20150306598 (Khandros et al.) and 20150306599 (Khandros et al.) and their corresponding PCT Publications WO2015/164846 and WO2015/164847, all of which are incorporated herein by reference in their entirety.

Examples of microfluidic devices having pens in which biological micro-objects (e.g., cells, such as mammalian cells, including immunological cells and stem cells), can be placed, cultured, and/or monitored have been described, for example, in US 2014/0116881 (application Ser. No. 14/060,117, filed Oct. 22, 2013), US 2015/0151298 (application Ser. No. 14/520,568, filed Oct. 22, 2014), and US 2015/0165436 (application Ser. No. 14/521,447, filed Oct. 22, 2014), each of which is incorporated herein by reference in its entirety. U.S. application Ser. Nos. 14/520,568 and 14/521,447 also describe exemplary methods of analyzing secretions of cells cultured in a microfluidic device. Each of the foregoing applications further describes microfluidic devices configured to produce dielectrophoretic (DEP) forces, such as optoelectronic tweezers (OET) or configured to provide opto-electro wetting (OEW). For example, the optoelectronic tweezers device illustrated in FIG. 2 of US 2014/0116881 is an example of a device that can be utilized in embodiments of the present disclosure to select and move an individual biological micro-object or a group of biological micro-objects.

Microfluidic device motive configurations. As described above, the control and monitoring equipment of the system can comprise a motive module for selecting and moving objects, such as micro-objects or droplets, in the microfluidic circuit of a microfluidic device. The microfluidic device can have a variety of motive configurations, depending upon the type of object being moved and other considerations. For example, a dielectrophoresis (DEP) configuration can be utilized to select and move micro-objects in the microfluidic circuit. Thus, the support structure 104 and/or cover 110 of the microfluidic device 100 can comprise a DEP configuration for selectively inducing DEP forces on micro-objects in a fluidic medium 180 in the microfluidic circuit 120 and thereby select, capture, and/or move individual micro-objects or groups of micro-objects. Alternatively, the support structure 104 and/or cover 110 of the microfluidic device 100 can comprise an electrowetting (EW) configuration for selectively inducing EW forces on droplets in a fluidic medium 180 in the microfluidic circuit 120 and thereby select, capture, and/or move individual droplets or groups of droplets.

Figure 1C:
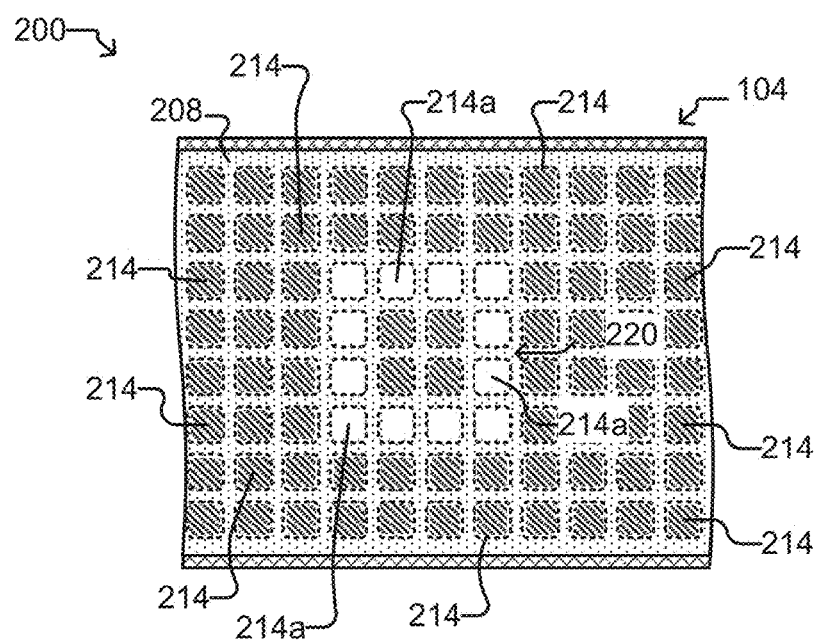

One example of a microfluidic device 200 comprising a DEP configuration is illustrated in FIGS. 1B and 1C. While for purposes of simplicity FIGS. 1B and 1C show a side cross-sectional view and a top cross-sectional view, respectively, of a portion of an enclosure 102 of the microfluidic device 200 having a region/chamber 202, it should be understood that the region/chamber 202 may be part of a fluidic circuit element having a more detailed structure, such as a growth chamber, a sequestration pen, a flow region, or a flow channel. Furthermore, the microfluidic device 200 may include other fluidic circuit elements. For example, the microfluidic device 200 can include a plurality of growth chambers or sequestration pens and/or one or more flow regions or flow channels, such as those described herein with respect to microfluidic device 100. A DEP configuration may be incorporated into any such fluidic circuit elements of the microfluidic device 200, or select portions thereof. It should be further appreciated that any of the above or below described microfluidic device components and system components may be incorporated in and/or used in combination with the microfluidic device 200. For example, system 150 including control and monitoring equipment 152, described above, may be used with microfluidic device 200, including one or more of the media module 160, motive module 162, imaging module 164, tilting module 166, and other modules 168.

As seen in FIG. 1B, the microfluidic device 200 includes a support structure 104 having a bottom electrode 204 and an electrode activation substrate 206 overlying the bottom electrode 204, and a cover 110 having a top electrode 210, with the top electrode 210 spaced apart from the bottom electrode 204. The top electrode 210 and the electrode activation substrate 206 define opposing surfaces of the region/chamber 202. A medium 180 contained in the region/chamber 202 thus provides a resistive connection between the top electrode 210 and the electrode activation substrate 206. A power source 212 configured to be connected to the bottom electrode 204 and the top electrode 210 and create a biasing voltage between the electrodes, as required for the generation of DEP forces in the region/chamber 202, is also shown. The power source 212 can be, for example, an alternating current (AC) power source.

In certain embodiments, the microfluidic device 200 illustrated in FIGS. 1B and 1C can have an optically-actuated DEP configuration. Accordingly, changing patterns of light 218 from the light source 216, which may be controlled by the motive module 162, can selectively activate and deactivate changing patterns of DEP electrodes at regions 214 of the inner surface 208 of the electrode activation substrate 206. (Hereinafter the regions 214 of a microfluidic device having a DEP configuration are referred to as "DEP electrode regions.") As illustrated in FIG. 1C, a light pattern 218 directed onto the inner surface 208 of the electrode activation substrate 206 can illuminate select DEP electrode regions 214a (shown in white) in a pattern, such as a square. The non-illuminated DEP electrode regions 214 (cross-hatched) are hereinafter referred to as "dark" DEP electrode regions 214. The relative electrical impedance through the DEP electrode activation substrate 206 (i.e., from the bottom electrode 204 up to the inner surface 208 of the electrode activation substrate 206 which interfaces with the medium 180 in the flow region 106) is greater than the relative electrical impedance through the medium 180 in the region/chamber 202 (i.e., from the inner surface 208 of the electrode activation substrate 206 to the top electrode 210 of the cover 110) at each dark DEP electrode region 214. An illuminated DEP electrode region 214a, however, exhibits a reduced relative impedance through the electrode activation substrate 206 that is less than the relative impedance through the medium 180 in the region/chamber 202 at each illuminated DEP electrode region 214a.

With the power source 212 activated, the foregoing DEP configuration creates an electric field gradient in the fluidic medium 180 between illuminated DEP electrode regions 214a and adjacent dark DEP electrode regions 214, which in turn creates local DEP forces that attract or repel nearby micro-objects (not shown) in the fluidic medium 180. DEP electrodes that attract or repel micro-objects in the fluidic medium 180 can thus be selectively activated and deactivated at many different such DEP electrode regions 214 at the inner surface 208 of the region/chamber 202 by changing light patterns 218 projected from a light source 216 into the microfluidic device 200. Whether the DEP forces attract or repel nearby micro-objects can depend on such parameters as the frequency of the power source 212 and the dielectric properties of the medium 180 and/or micro-objects (not shown).

The square pattern 220 of illuminated DEP electrode regions 214a illustrated in FIG. 1C is an example only. Any pattern of the DEP electrode regions 214 can be illuminated (and thereby activated) by the pattern of light 218 projected into the microfluidic device 200, and the pattern of illuminated/activated DEP electrode regions 214 can be repeatedly changed by changing or moving the light pattern 218.

In some embodiments, the electrode activation substrate 206 can comprise or consist of a photoconductive material. In such embodiments, the inner surface 208 of the electrode activation substrate 206 can be featureless. For example, the electrode activation substrate 206 can comprise or consist of a layer of hydrogenated amorphous silicon (a-Si:H). The a-Si:H can comprise, for example, about 8% to 40% hydrogen (calculated as 100*the number of hydrogen atoms/the total number of hydrogen and silicon atoms). The layer of a-Si:H can have a thickness of about 500 nm to about 2.0 µm. In such embodiments, the DEP electrode regions 214 can be created anywhere and in any pattern on the inner surface 208 of the electrode activation substrate 206, in accordance with the light pattern 218. The number and pattern of the DEP electrode regions 214 thus need not be fixed, but can correspond to the light pattern 218. Examples of microfluidic devices having a DEP configuration comprising a photoconductive layer such as discussed above have been described, for example, in U.S. Pat. No. RE 44,711 (Wu et al.) (originally issued as U.S. Pat. No. 7,612,355), the entire contents of which are incorporated herein by reference.

In other embodiments, the electrode activation substrate 206 can comprise a substrate comprising a plurality of doped layers, electrically insulating layers (or regions), and electrically conductive layers that form semiconductor integrated circuits, such as is known in semiconductor fields. For example, the electrode activation substrate 206 can comprise a plurality of phototransistors, including, for example, lateral bipolar phototransistors, each phototransistor corresponding to a DEP electrode region 214. Alternatively, the electrode activation substrate 206 can comprise electrodes (e.g., conductive metal electrodes) controlled by phototransistor switches, with each such electrode corresponding to a DEP electrode region 214. The electrode activation substrate 206 can include a pattern of such phototransistors or phototransistor-controlled electrodes. The pattern, for example, can be an array of substantially square phototransistors or phototransistor-controlled electrodes arranged in rows and columns, such as shown in FIG. 2B. Alternatively, the pattern can be an array of substantially hexagonal phototransistors or phototransistor-controlled electrodes that form a hexagonal lattice. Regardless of the pattern, electric circuit elements can form electrical connections between the DEP electrode regions 214 at the inner surface 208 of the electrode activation substrate 206 and the bottom electrode 210, and those electrical connections (i.e., phototransistors or electrodes) can be selectively activated and deactivated by the light pattern 218. When not activated, each electrical connection can have high impedance such that the relative impedance through the electrode activation substrate 206 (i.e., from the bottom electrode 204 to the inner surface 208 of the electrode activation substrate 206 which interfaces with the medium 180 in the region/chamber 202) is greater than the relative impedance through the medium 180 (i.e., from the inner surface 208 of the electrode activation substrate 206 to the top electrode 210 of the cover 110) at the corresponding DEP electrode region 214. When activated by light in the light pattern 218, however, the relative impedance through the electrode activation substrate 206 is less than the relative impedance through the medium 180 at each illuminated DEP electrode region 214, thereby activating the DEP electrode at the corresponding DEP electrode region 214 as discussed above. DEP electrodes that attract or repel micro-objects (not shown) in the medium 180 can thus be selectively activated and deactivated at many different DEP electrode regions 214 at the inner surface 208 of the electrode activation substrate 206 in the region/chamber 202 in a manner determined by the light pattern 218.

Examples of microfluidic devices having electrode activation substrates that comprise phototransistors have been described, for example, in U.S. Pat. No. 7,956,339 (Ohta et al.) (see, e.g., device 300 illustrated in FIGS. 21 and 22, and descriptions thereof), and U.S. Patent Publication No. 2016/0184821 (Hobbs et al.) (see, e.g., devices 200, 502, 504, 600, and 700 illustrated throughout the drawings, and descriptions thereof), the entire contents of each of which are incorporated herein by reference. Examples of microfluidic devices having electrode activation substrates that comprise electrodes controlled by phototransistor switches have been described, for example, in U.S. Patent Publication No. 2014/0124370 (Short et al.) (see, e.g., devices 200, 400, 500, 600, and 900 illustrated throughout the drawings, and descriptions thereof), the entire contents of which are incorporated herein by reference.

In some embodiments of a DEP configured microfluidic device, the top electrode 210 is part of a first wall (or cover 110) of the enclosure 102, and the electrode activation substrate 206 and bottom electrode 204 are part of a second wall (or support structure 104) of the enclosure 102. The region/chamber 202 can be between the first wall and the second wall. In other embodiments, the electrode 210 is part of the second wall (or support structure 104) and one or both of the electrode activation substrate 206 and/or the electrode 210 are part of the first wall (or cover 110). Moreover, the light source 216 can alternatively be used to illuminate the enclosure 102 from below.

With the microfluidic device 200 of FIGS. 1B-1C having a DEP configuration, the motive module 162 can select a micro-object (not shown) in the medium 180 in the region/chamber 202 by projecting a light pattern 218 into the microfluidic device 200 to activate a first set of one or more DEP electrodes at DEP electrode regions 214a of the inner surface 208 of the electrode activation substrate 206 in a pattern (e.g., square pattern 220) that surrounds and captures the micro-object. The motive module 162 can then move the in situ-generated captured micro-object by moving the light pattern 218 relative to the microfluidic device 200 to activate a second set of one or more DEP electrodes at DEP electrode regions 214. Alternatively, the microfluidic device 200 can be moved relative to the light pattern 218.

In other embodiments, the microfluidic device 200 can have a DEP configuration that does not rely upon light activation of DEP electrodes at the inner surface 208 of the electrode activation substrate 206. For example, the electrode activation substrate 206 can comprise selectively addressable and energizable electrodes positioned opposite to a surface including at least one electrode (e.g., cover 110). Switches (e.g., transistor switches in a semiconductor substrate) may be selectively opened and closed to activate or inactivate DEP electrodes at DEP electrode regions 214, thereby creating a net DEP force on a micro-object (not shown) in region/chamber 202 in the vicinity of the activated DEP electrodes. Depending on such characteristics as the frequency of the power source 212 and the dielectric properties of the medium (not shown) and/or micro-objects in the region/chamber 202, the DEP force can attract or repel a nearby micro-object. By selectively activating and deactivating a set of DEP electrodes (e.g., at a set of DEP electrodes regions 214 that forms a square pattern 220), one or more micro-objects in region/chamber 202 can be trapped and moved within the region/chamber 202. The motive module 162 in FIG. 1A can control such switches and thus activate and deactivate individual ones of the DEP electrodes to select, trap, and move particular micro-objects (not shown) around the region/chamber 202. Microfluidic devices having a DEP configuration that includes selectively addressable and energizable electrodes are known in the art and have been described, for example, in U.S. Pat. No. 6,294,063 (Becker et al.) and U.S. Pat. No. 6,942,776 (Medoro), the entire contents of which are incorporated herein by reference.

As yet another example, the microfluidic device 200 can have an electrowetting (EW) configuration, which can be in place of the DEP configuration or can be located in a portion of the microfluidic device 200 that is separate from the portion which has the DEP configuration. The EW configuration can be an opto-electrowetting configuration or an electrowetting on dielectric (EWOD) configuration, both of which are known in the art. In some EW configurations, the support structure 104 has an electrode activation substrate 206 sandwiched between a dielectric layer (not shown) and the bottom electrode 204. The dielectric layer can comprise a hydrophobic material and/or can be coated with a hydrophobic material, as described below. For microfluidic devices 200 that have an EW configuration, the inner surface 208 of the support structure 104 is the inner surface of the dielectric layer or its hydrophobic coating.

The dielectric layer (not shown) can comprise one or more oxide layers, and can have a thickness of about 50 nm to about 250 nm (e.g., about 125 nm to about 175 nm). In certain embodiments, the dielectric layer may comprise a layer of oxide, such as a metal oxide (e.g., aluminum oxide or hafnium oxide). In certain embodiments, the dielectric layer can comprise a dielectric material other than a metal oxide, such as silicon oxide or a nitride. Regardless of the exact composition and thickness, the dielectric layer can have an impedance of about 10 kOhms to about 50 kOhms.

In some embodiments, the surface of the dielectric layer that faces inward toward region/chamber 202 is coated with a hydrophobic material. The hydrophobic material can comprise, for example, fluorinated carbon molecules. Examples of fluorinated carbon molecules include perfluoro-polymers such as polytetrafluoroethylene (e.g., TEFLON®) or poly (2,3-difluoromethylenyl-perfluorotetrahydrofuran) (e.g., CYTOP™). Molecules that make up the hydrophobic material can be covalently bonded to the surface of the dielectric layer. For example, molecules of the hydrophobic material can be covalently bound to the surface of the dielectric layer by means of a linker such as a siloxane group, a phosphonic acid group, or a thiol group. Thus, in some embodiments, the hydrophobic material can comprise alkyl-terminated siloxane, alkyl-termination phosphonic acid, or alkyl-terminated thiol. The alkyl group can be long-chain hydrocarbons (e.g., having a chain of at least 10 carbons, or at least 16, 18, 20, 22, or more carbons). Alternatively, fluorinated (or perfluorinated) carbon chains can be used in place of the alkyl groups. Thus, for example, the hydrophobic material can comprise fluoroalkyl-terminated siloxane, fluoroalkyl-terminated phosphonic acid, or fluoroalkyl-terminated thiol. In some embodiments, the hydrophobic coating has a thickness of about 10 nm to about 50 nm. In other embodiments, the hydrophobic coating has a thickness of less than 10 nm (e.g., less than 5 nm, or about 1.5 to 3.0 nm).

In some embodiments, the cover 110 of a microfluidic device 200 having an electrowetting configuration is coated with a hydrophobic material (not shown) as well. The hydrophobic material can be the same hydrophobic material used to coat the dielectric layer of the support structure 104, and the hydrophobic coating can have a thickness that is substantially the same as the thickness of the hydrophobic coating on the dielectric layer of the support structure 104. Moreover, the cover 110 can comprise an electrode activation substrate 206 sandwiched between a dielectric layer and the top electrode 210, in the manner of the support structure 104. The electrode activation substrate 206 and the dielectric layer of the cover 110 can have the same composition and/or dimensions as the electrode activation substrate 206 and the dielectric layer of the support structure 104. Thus, the microfluidic device 200 can have two electrowetting surfaces.

In some embodiments, the electrode activation substrate 206 can comprise a photoconductive material, such as described above. Accordingly, in certain embodiments, the electrode activation substrate 206 can comprise or consist of a layer of hydrogenated amorphous silicon (a-Si:H). The a-Si:H can comprise, for example, about 8% to 40% hydrogen (calculated as 100 * the number of hydrogen atoms/the total number of hydrogen and silicon atoms). The layer of a-Si:H can have a thickness of about 500 nm to about 2.0 µm. Alternatively, the electrode activation substrate 206 can comprise electrodes (e.g., conductive metal electrodes) controlled by phototransistor switches, as described above. Microfluidic devices having an opto-electrowetting configuration are known in the art and/or can be constructed with electrode activation substrates known in the art. For example, U.S. Pat. No. 6,958,132 (Chiou et al.), the entire contents of which are incorporated herein by reference, discloses opto-electrowetting configurations having a photoconductive material such as a-Si:H, while U.S. Patent Publication No. 2014/0124370 (Short et al.), referenced above, discloses electrode activation substrates having electrodes controlled by phototransistor switches.

The microfluidic device 200 thus can have an opto-electrowetting configuration, and light patterns 218 can be used to activate photoconductive EW regions or photoresponsive EW electrodes in the electrode activation substrate 206. Such activated EW regions or EW electrodes of the electrode activation substrate 206 can generate an electrowetting force at the inner surface 208 of the support structure 104 (i.e., the inner surface of the overlaying dielectric layer or its hydrophobic coating). By changing the light patterns 218 (or moving microfluidic device 200 relative to the light source 216) incident on the electrode activation substrate 206, droplets (e.g., containing an aqueous medium, solution, or solvent) contacting the inner surface 208 of the support structure 104 can be moved through an immiscible fluid (e.g., an oil medium) present in the region/chamber 202.

In other embodiments, microfluidic devices 200 can have an EWOD configuration, and the electrode activation substrate 206 can comprise selectively addressable and energizable electrodes that do not rely upon light for activation. The electrode activation substrate 206 thus can include a pattern of such electrowetting (EW) electrodes. The pattern, for example, can be an array of substantially square EW electrodes arranged in rows and columns, such as shown in FIG. 2B. Alternatively, the pattern can be an array of substantially hexagonal EW electrodes that form a hexagonal lattice. Regardless of the pattern, the EW electrodes can be selectively activated (or deactivated) by electrical switches (e.g., transistor switches in a semiconductor substrate). By selectively activating and deactivating EW electrodes in the electrode activation substrate 206, droplets (not shown) contacting the inner surface 208 of the overlaying dielectric layer or its hydrophobic coating can be moved within the region/chamber 202. The motive module 162 in FIG. 1A can control such switches and thus activate and deactivate individual EW electrodes to select and move particular droplets around region/chamber 202. Microfluidic devices having a EWOD configuration with selectively addressable and energizable electrodes are known in the art and have been described, for example, in U.S. Pat. No. 8,685,344 (Sundarsan et al.), the entire contents of which are incorporated herein by reference.

Regardless of the configuration of the microfluidic device 200, a power source 212 can be used to provide a potential (e.g., an AC voltage potential) that powers the electrical circuits of the microfluidic device 200. The power source 212 can be the same as, or a component of, the power source 192 referenced in FIG. 1. Power source 212 can be configured to provide an AC voltage and/or current to the top electrode 210 and the bottom electrode 204. For an AC voltage, the power source 212 can provide a frequency range and an average or peak power (e.g., voltage or current) range sufficient to generate net DEP forces (or electrowetting forces) strong enough to trap and move individual micro-objects (not shown) in the region/chamber 202, as discussed above, and/or to change the wetting properties of the inner surface 208 of the support structure 104 (i.e., the dielectric layer and/or the hydrophobic coating on the dielectric layer) in the region/chamber 202, as also discussed above. Such frequency ranges and average or peak power ranges are known in the art. See, e.g., U.S. Pat. No. 6,958,132 (Chiou et al.), U.S. Pat. No. RE44,711 (Wu et al.) (originally issued as U.S. Pat. No. 7,612,355), and US Patent Application Publication Nos. US2014/0124370 (Short et al.), US2015/0306598 (Khandros et al.), and US2015/0306599 (Khandros et al.).

Sequestration pens. Non-limiting examples of generic sequestration pens 224, 226, and 228 are shown within the microfluidic device 230 depicted in FIGS. 2A-2C. Each sequestration pen 224, 226, and 228 can comprise an isolation structure 232 defining an isolation region 240 and a connection region 236 fluidically connecting the isolation region 240 to a channel 122. The connection region 236 can comprise a proximal opening 234 to the microfluidic channel 122 and a distal opening 238 to the isolation region 240. The connection region 236 can be configured so that the maximum penetration depth of a flow of a fluidic medium (not shown) flowing from the microfluidic channel 122 into the sequestration pen 224, 226, 228 does not extend into the isolation region 240. Thus, due to the connection region 236, a micro-object (not shown) or other material (not shown) disposed in an isolation region 240 of a sequestration pen 224, 226, 228 can thus be isolated from, and not substantially affected by, a flow of medium 180 in the microfluidic channel 122.

Figure 2A:
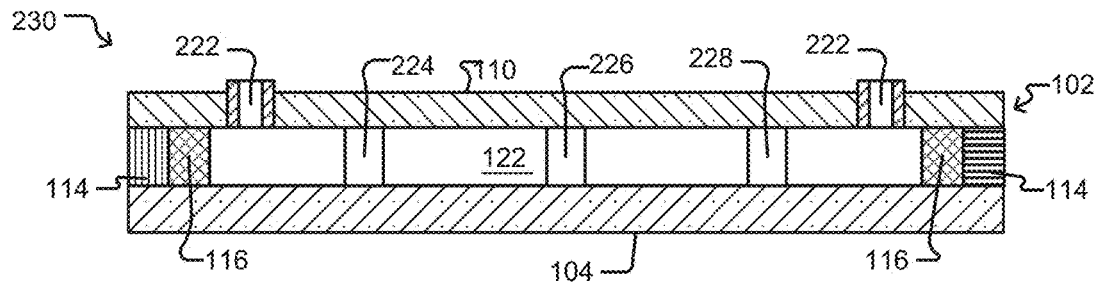
FIGS. 2A and 2B illustrate isolation pens according to some embodiments of the disclosure.
Figure 2B:
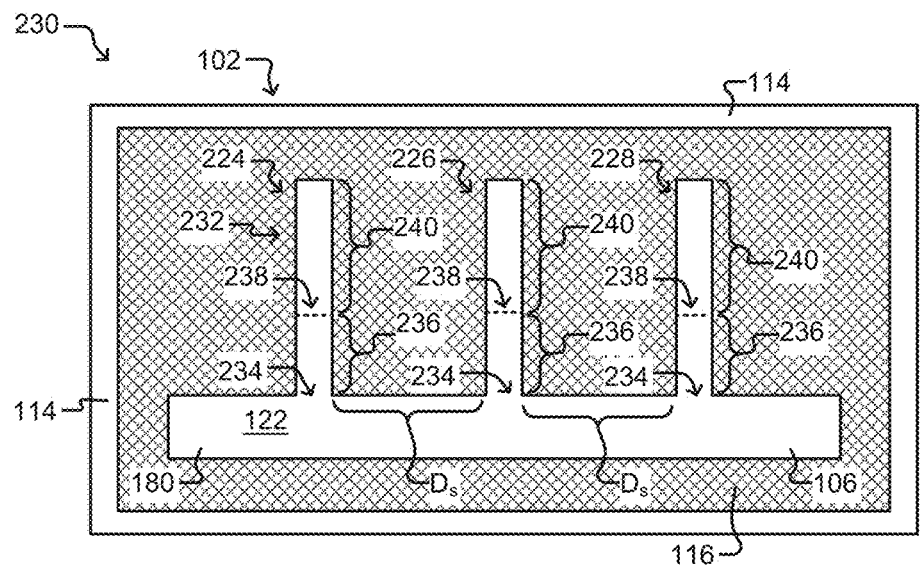
Figure 2C:
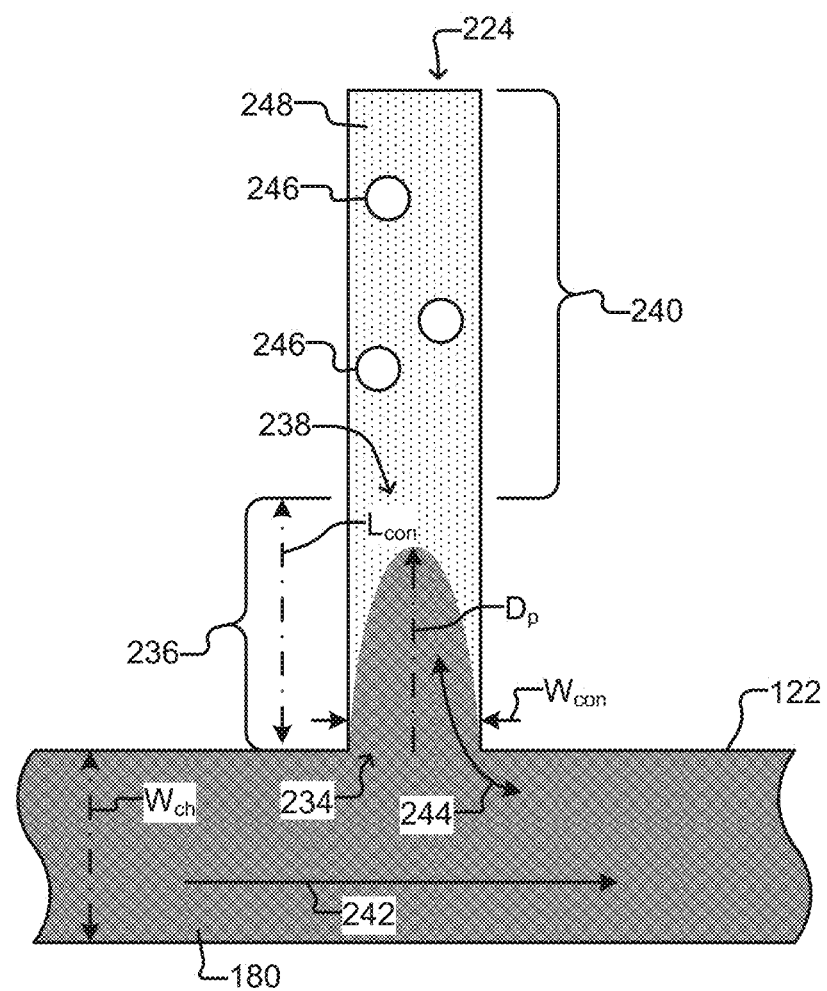
FIG. 2C illustrates a detailed sequestration pen according to some embodiments of the disclosure.

The sequestration pens 224, 226, and 228 of FIGS. 2A-2C each have a single opening which opens directly to the microfluidic channel 122. The opening of the sequestration pen opens laterally from the microfluidic channel 122. The electrode activation substrate 206 underlays both the microfluidic channel 122 and the sequestration pens 224, 226, and 228. The upper surface of the electrode activation substrate 206 within the enclosure of a sequestration pen, forming the floor of the sequestration pen, is disposed at the same level or substantially the same level of the upper surface the of electrode activation substrate 206 within the microfluidic channel 122 (or flow region if a channel is not present), forming the floor of the flow channel (or flow region, respectively) of the microfluidic device. The electrode activation substrate 206 may be featureless or may have an irregular or patterned surface that varies from its highest elevation to its lowest depression by less than about 3 microns, 2.5 microns, 2 microns, 1.5 microns, 1 micron, 0.9 microns, 0.5 microns, 0.4 microns, 0.2 microns, 0.1 microns or less. The variation of elevation in the upper surface of the substrate across both the microfluidic channel 122 (or flow region) and sequestration pens may be less than about 3%, 2%, 1%. 0.9%, 0.8%, 0.5%, 0.3% or 0.1% of the height of the walls of the sequestration pen or walls of the microfluidic device. While described in detail for the microfluidic device 200, this also applies to any of the microfluidic devices 100, 230, 250, 280, 290, 320, 400, 450, 500, 700 described herein.

The microfluidic channel 122 can thus be an example of a swept region, and the isolation regions 240 of the sequestration pens 224, 226, 228 can be examples of unswept regions. As noted, the microfluidic channel 122 and sequestration pens 224, 226, 228 can be configured to contain one or more fluidic media 180. In the example shown in FIGS. 2A-2B, the ports 222 are connected to the microfluidic channel 122 and allow a fluidic medium 180 to be introduced into or removed from the microfluidic device 230. Prior to introduction of the fluidic medium 180, the microfluidic device may be primed with a gas such as carbon dioxide gas. Once the microfluidic device 230 contains the fluidic medium 180, the flow 242 of fluidic medium 180 in the microfluidic channel 122 can be selectively generated and stopped. For example, as shown, the ports 222 can be disposed at different locations (e.g., opposite ends) of the microfluidic channel 122, and a flow 242 of medium can be created from one port 222 functioning as an inlet to another port 222 functioning as an outlet.

FIG. 2C illustrates a detailed view of an example of a sequestration pen 224 according to the present disclosure. Examples of micro-objects 246 are also shown.

As is known, a flow 242 of fluidic medium 180 in a microfluidic channel 122 past a proximal opening 234 of sequestration pen 224 can cause a secondary flow 244 of the medium 180 into and/or out of the sequestration pen 224. To isolate micro-objects 246 in the isolation region 240 of a sequestration pen 224 from the secondary flow 244, the length $L_{con}$ of the connection region 236 of the sequestration pen 224 (i.e., from the proximal opening 234 to the distal opening 238) should be greater than the penetration depth $D_p$ of the secondary flow 244 into the connection region 236. The penetration depth $D_p$ of the secondary flow 244 depends upon the velocity of the fluidic medium 180 flowing in the microfluidic channel 122 and various parameters relating to the configuration of the microfluidic channel 122 and the proximal opening 234 of the connection region 236 to the microfluidic channel 122. For a given microfluidic device, the configurations of the microfluidic channel 122 and the opening 234 will be fixed, whereas the rate of flow 242 of fluidic medium 180 in the microfluidic channel 122 will be variable. Accordingly, for each sequestration pen 224, a maximal velocity $V_{max}$ for the flow 242 of fluidic medium 180 in channel 122 can be identified that ensures that the penetration depth $D_p$ of the secondary flow 244 does not exceed the length $L_{con}$ of the connection region 236. As long as the rate of the flow 242 of fluidic medium 180 in the microfluidic channel 122 does not exceed the maximum velocity $V_{max}$, the resulting secondary flow 244 can be limited to the microfluidic channel 122 and the connection region 236 and kept out of the isolation region 240. The flow 242 of medium 180 in the microfluidic channel 122 will thus not draw micro-objects 246 out of the isolation region 240. Rather, micro-objects 246 located in the isolation region 240 will stay in the isolation region 240 regardless of the flow 242 of fluidic medium 180 in the microfluidic channel 122.

Moreover, as long as the rate of flow 242 of medium 180 in the microfluidic channel 122 does not exceed $V_{max}$, the flow 242 of fluidic medium 180 in the microfluidic channel 122 will not move miscellaneous particles (e.g., microparticles and/or nanoparticles) from the microfluidic channel 122 into the isolation region 240 of a sequestration pen 224. Having the length $L_{con}$ of the connection region 236 be greater than the maximum penetration depth $D_p$ of the secondary flow 244 can thus prevent contamination of one sequestration pen 224 with miscellaneous particles from the microfluidic channel 122 or another sequestration pen (e.g., sequestration pens 226, 228 in FIG. 2D).

Because the microfluidic channel 122 and the connection regions 236 of the sequestration pens 224, 226, 228 can be affected by the flow 242 of medium 180 in the microfluidic channel 122, the microfluidic channel 122 and connection regions 236 can be deemed swept (or flow) regions of the microfluidic device 230. The isolation regions 240 of the sequestration pens 224, 226, 228, on the other hand, can be deemed unswept (or non-flow) regions. For example, components (not shown) in a first fluidic medium 180 in the microfluidic channel 122 can mix with a second fluidic medium 248 in the isolation region 240 substantially only by diffusion of components of the first medium 180 from the microfluidic channel 122 through the connection region 236 and into the second fluidic medium 248 in the isolation region 240. Similarly, components (not shown) of the second medium 248 in the isolation region 240 can mix with the first medium 180 in the microfluidic channel 122 substantially only by diffusion of components of the second medium 248 from the isolation region 240 through the connection region 236 and into the first medium 180 in the microfluidic channel 122. In some embodiments, the extent of fluidic medium exchange between the isolation region of a sequestration pen and the flow region by diffusion is greater than about 90%, 91%, 92%, 93%, 94% 95%, 96%, 97%, 98%, or greater than about 99% of fluidic exchange. The first medium 180 can be the same medium or a different medium than the second medium 248. Moreover, the first medium 180 and the second medium 248 can start out being the same, then become different (e.g., through conditioning of the second medium 248 by one or more cells in the isolation region 240, or by changing the medium 180 flowing through the microfluidic channel 122).

The maximum penetration depth $D_p$ of the secondary flow 244 caused by the flow 242 of fluidic medium 180 in the microfluidic channel 122 can depend on a number of parameters, as mentioned above. Examples of such parameters include: the shape of the microfluidic channel 122 (e.g., the microfluidic channel can direct medium into the connection region 236, divert medium away from the connection region 236, or direct medium in a direction substantially perpendicular to the proximal opening 234 of the connection region 236 to the microfluidic channel 122); a width $W_{ch}$ (or cross-sectional area) of the microfluidic channel 122 at the proximal opening 234; and a width $W_{con}$ (or cross-sectional area) of the connection region 236 at the proximal opening 234; the velocity V of the flow 242 of fluidic medium 180 in the microfluidic channel 122; the viscosity of the first medium 180 and/or the second medium 248, or the like.

In some embodiments, the dimensions of the microfluidic channel 122 and sequestration pens 224, 226, 228 can be oriented as follows with respect to the vector of the flow 242 of fluidic medium 180 in the microfluidic channel 122: the microfluidic channel width $W_{ch}$ (or cross-sectional area of the microfluidic channel 122) can be substantially perpendicular to the flow 242 of medium 180; the width $W_{con}$ (or cross-sectional area) of the connection region 236 at opening 234 can be substantially parallel to the flow 242 of medium 180 in the microfluidic channel 122; and/or the length $L_{con}$ of the connection region can be substantially perpendicular to the flow 242 of medium 180 in the microfluidic channel 122. The foregoing are examples only, and the relative position of the microfluidic channel 122 and sequestration pens 224, 226, 228 can be in other orientations with respect to each other.

As illustrated in FIG. 2C, the width $W_{con}$ of the connection region 236 can be uniform from the proximal opening 234 to the distal opening 238. The width $W_{con}$ of the connection region 236 at the distal opening 238 can thus be in any of the ranges identified herein for the width $W_{con}$ of the connection region 236 at the proximal opening 234. Alternatively, the width $W_{con}$ of the connection region 236 at the distal opening 238 can be larger than the width $W_{con}$ of the connection region 236 at the proximal opening 234.

As illustrated in FIG. 2C, the width of the isolation region 240 at the distal opening 238 can be substantially the same as the width $W_{con}$ of the connection region 236 at the proximal opening 234. The width of the isolation region 240 at the distal opening 238 can thus be in any of the ranges identified herein for the width $W_{con}$ of the connection region 236 at the proximal opening 234. Alternatively, the width of the isolation region 240 at the distal opening 238 can be larger or smaller than the width $W_{con}$ of the connection region 236 at the proximal opening 234. Moreover, the distal opening 238 may be smaller than the proximal opening 234 and the width $W_{con}$ of the connection region 236 may be narrowed between the proximal opening 234 and distal opening 238. For example, the connection region 236 may be narrowed between the proximal opening and the distal opening, using a variety of different geometries (e.g. chamfering the connection region, beveling the connection region). Further, any part or subpart of the connection region 236 may be narrowed (e.g. a portion of the connection region adjacent to the proximal opening 234).

Figure 2D:
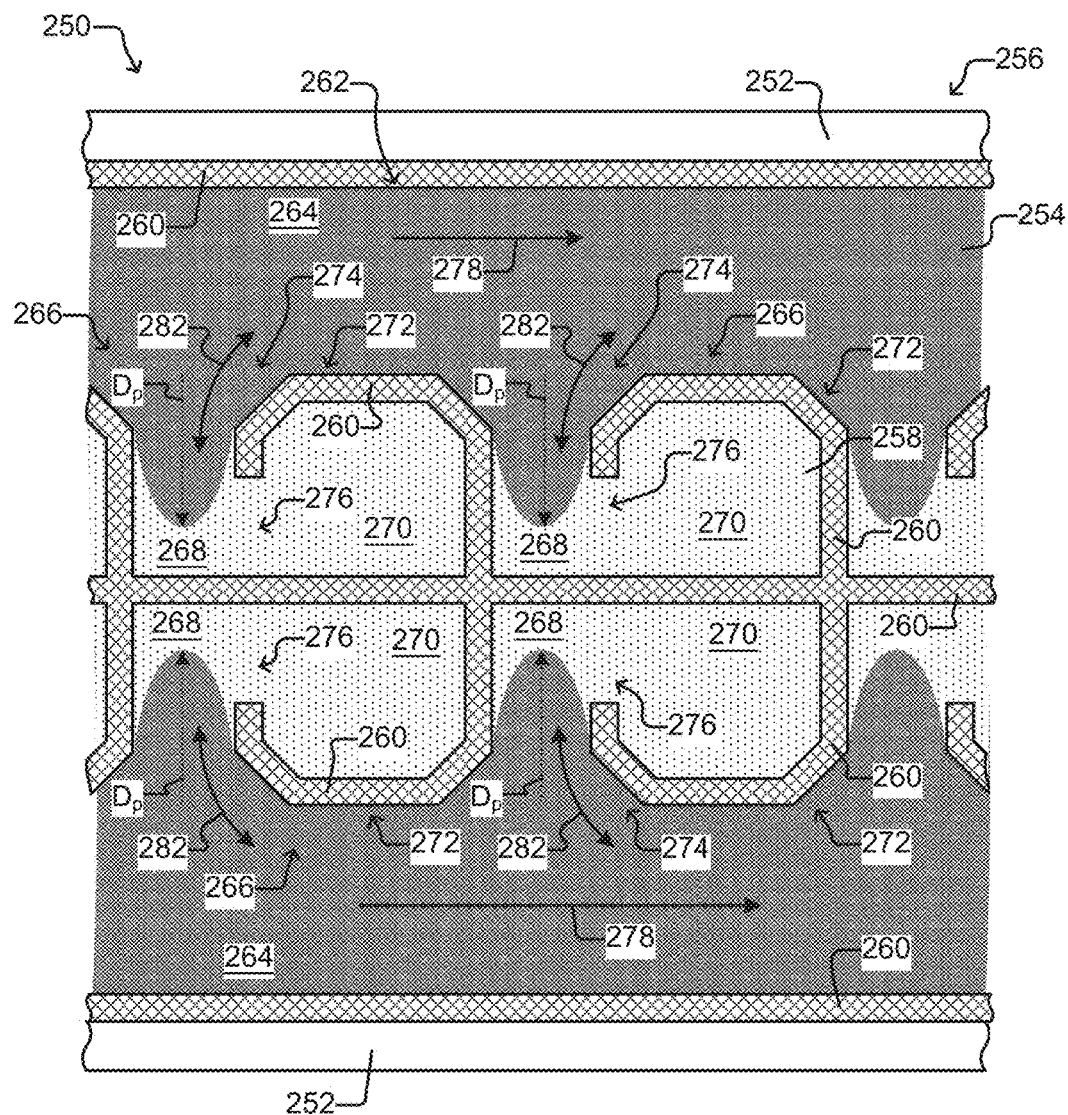
FIGS. 2D-F illustrate sequestration pens according to some other embodiments of the disclosure.
Figure 2E:
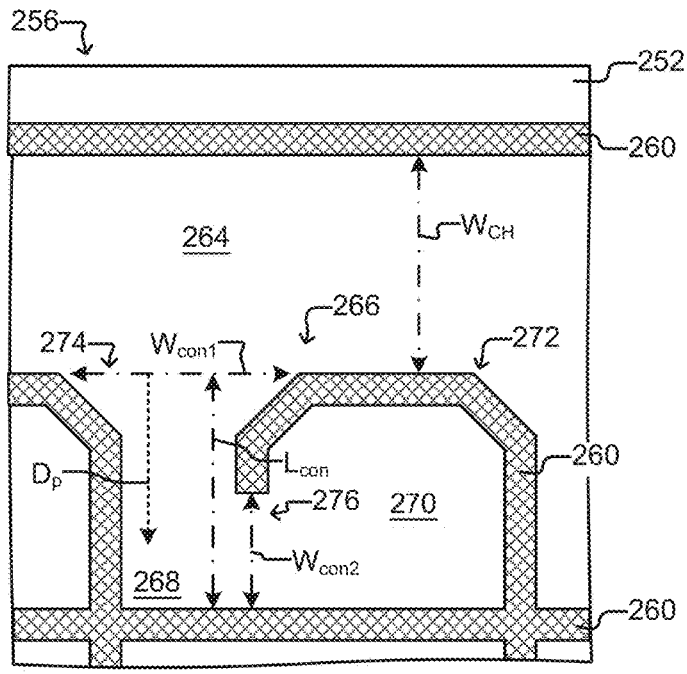
Figure 2F:
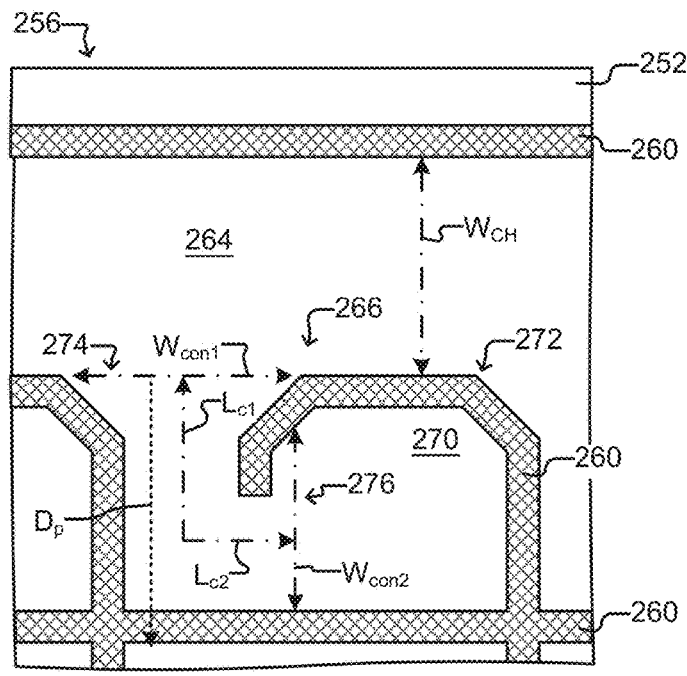

FIGS. 2D-2F depict another exemplary embodiment of a microfluidic device 250 containing a microfluidic circuit 262 and flow channels 264, which are variations of the respective microfluidic device 100, circuit 132 and channel 134 of FIG. 1A. The microfluidic device 250 also has a plurality of sequestration pens 266 that are additional variations of the above-described sequestration pens 124, 126, 128, 130, 224, 226 or 228. In particular, it should be appreciated that the sequestration pens 266 of device 250 shown in FIGS. 2D-2F can replace any of the above-described sequestration pens 124, 126, 128, 130, 224, 226 or 228 in devices 100, 200, 230, 280, 290, 300. Likewise, the microfluidic device 250 is another variant of the microfluidic device 100, and may also have the same or a different DEP configuration as the above-described microfluidic device 100, 200, 230, 280, 290, 300, as well as any of the other microfluidic system components described herein.

The microfluidic device 250 of FIGS. 2D-2Fcomprises a support structure (not visible in FIGS. 2D-2F, but can be the same or generally similar to the support structure 104 of device 100 depicted in FIG. 1A), a microfluidic circuit structure 256, and a cover (not visible in FIGS. 2D-2F, but can be the same or generally similar to the cover 122 of device 100 depicted in FIG. 1A). The microfluidic circuit structure 256 includes a frame 252 and microfluidic circuit material 260, which can be the same as or generally similar to the frame 114 and microfluidic circuit material 116 of device 100 shown in FIG. 1A. As shown in FIG. 2D, the microfluidic circuit 262 defined by the microfluidic circuit material 260 can comprise multiple channels 264 (two are shown but there can be more) to which multiple sequestration pens 266 are fluidically connected.

Each sequestration pen 266 can comprise an isolation structure 272, an isolation region 270 within the isolation structure 272, and a connection region 268. From a proximal opening 274 at the microfluidic channel 264 to a distal opening 276 at the isolation structure 272, the connection region 268 fluidically connects the microfluidic channel 264 to the isolation region 270. Generally, in accordance with the above discussion of FIGS. 2B and 2C, a flow 278 of a first fluidic medium 254 in a channel 264 can create secondary flows 282 of the first medium 254 from the microfluidic channel 264 into and/or out of the respective connection regions 268 of the sequestration pens 266.

As illustrated in FIG. 2E, the connection region 268 of each sequestration pen 266 generally includes the area extending between the proximal opening 274 to a channel 264 and the distal opening 276 to an isolation structure 272. The length $L_{con}$ of the connection region 268 can be greater than the maximum penetration depth $D_p$ of secondary flow 282, in which case the secondary flow 282 will extend into the connection region 268 without being redirected toward the isolation region 270 (as shown in FIG. 2D). Alternatively, at illustrated in FIG. 2F, the connection region 268 can have a length $L_{con}$ that is less than the maximum penetration depth $D_p$, in which case the secondary flow 282 will extend through the connection region 268 and be redirected toward the isolation region 270. In this latter situation, the sum of lengths $L_{c1}$ and $L_{c2}$ of connection region 268 is greater than the maximum penetration depth $D_p$, so that secondary flow 282 will not extend into isolation region 270. Whether length $L_{con}$ of connection region 268 is greater than the penetration depth $D_p$, or the sum of lengths $L_{c1}$ and $L_{c2}$ of connection region 268 is greater than the penetration depth $D_p$, a flow 278 of a first medium 254 in channel 264 that does not exceed a maximum velocity $V_{max}$ will produce a secondary flow having a penetration depth $D_p$, and micro-objects (not shown but can be the same or generally similar to the micro-objects 246 shown in FIG. 2C) in the isolation region 270 of a sequestration pen 266 will not be drawn out of the isolation region 270 by a flow 278 of first medium 254 in channel 264. Nor will the flow 278 in channel 264 draw miscellaneous materials (not shown) from channel 264 into the isolation region 270 of a sequestration pen 266. As such, diffusion is the only mechanism by which components in a first medium 254 in the microfluidic channel 264 can move from the microfluidic channel 264 into a second medium 258 in an isolation region 270 of a sequestration pen 266. Likewise, diffusion is the only mechanism by which components in a second medium 258 in an isolation region 270 of a sequestration pen 266 can move from the isolation region 270 to a first medium 254 in the microfluidic channel 264. The first medium 254 can be the same medium as the second medium 258, or the first medium 254 can be a different medium than the second medium 258. Alternatively, the first medium 254 and the second medium 258 can start out being the same, then become different, e.g., through conditioning of the second medium by one or more cells in the isolation region 270, or by changing the medium flowing through the microfluidic channel 264.

As illustrated in FIG. 2E, the width $W_{ch}$ of the microfluidic channels 264 (i.e., taken transverse to the direction of a fluid medium flow through the microfluidic channel indicated by arrows 278 in FIG. 2D) in the microfluidic channel 264 can be substantially perpendicular to a width $W_{con1}$ of the proximal opening 274 and thus substantially parallel to a width $W_{con2}$ of the distal opening 276. The width $W_{con1}$ of the proximal opening 274 and the width $W_{con2}$ of the distal opening 276, however, need not be substantially perpendicular to each other. For example, an angle between an axis (not shown) on which the width $W_{con1}$ of the proximal opening 274 is oriented and another axis on which the width $W_{con2}$ of the distal opening 276 is oriented can be other than perpendicular and thus other than 90°. Examples of alternatively oriented angles include angles in any of the following ranges: from about 30° to about 90°, from about 45° to about 90°, from about 60° to about 90°, or the like.

In various embodiments of sequestration pens (e.g. 124, 126, 128, 130, 224, 226, 228, or 266), the isolation region (e.g. 240 or 270) is configured to contain a plurality of micro-objects. In other embodiments, the isolation region can be configured to contain only one, two, three, four, five, or a similar relatively small number of micro-objects. Accordingly, the volume of an isolation region can be, for example, at least $1 \times 10^6$, $2 \times 10^6$, $4 \times 10^6$, $6 \times 10^6$ cubic microns, or more.

In various embodiments of sequestration pens, the width $W_{ch}$ of the microfluidic channel (e.g., 122) at a proximal opening (e.g. 234) can be within any of the following ranges: about 50-1000 microns, 50-500 microns, 50-400 microns, 50-300 microns, 50-250 microns, 50-200 microns, 50-150 microns, 50-100 microns, 70-500 microns, 70-400 microns, 70-300 microns, 70-250 microns, 70-200 microns, 70-150 microns, 90-400 microns, 90-300 microns, 90-250 microns, 90-200 microns, 90-150 microns, 100-300 microns, 100-250 microns, 100-200 microns, 100-150 microns, and 100-120 microns. In some other embodiments, the width $W_{ch}$ of the microfluidic channel (e.g., 122) at a proximal opening (e.g. 234) can be in a range of about 200-800 microns, 200-700 microns, or 200-600 microns. The foregoing are examples only, and the width $W_{ch}$ of the microfluidic channel 122 can be in other ranges (e.g., a range defined by any of the endpoints listed above). Moreover, the $W_{ch}$ of the microfluidic channel 122 can be selected to be in any of these ranges in regions of the microfluidic channel other than at a proximal opening of a sequestration pen.

In some embodiments, a sequestration pen has a height of about 30 to about 200 microns, or about 50 to about 150 microns. In some embodiments, the sequestration pen has a cross-sectional area of about $1 \times 10^4$-$3 \times 10^6$ square microns, $2 \times 10^4$-$2 \times 10^6$ square microns, $4 \times 10^4$-$1 \times 10^6$ square microns, $2 \times 10^4$-$5 \times 10^5$ square microns, $2 \times 10^4$-$1 \times 10^5$ square microns or about $2 \times 10^5$-$2 \times 10^6$ square microns.

In various embodiments of sequestration pens, the height $H_{ch}$ of the microfluidic channel (e.g.,122) at a proximal opening (e.g., 234) can be within any of the following ranges: 20-100 microns, 20-90 microns, 20-80 microns, 20-70 microns, 20-60 microns, 20-50 microns, 30-100 microns, 30-90 microns, 30-80 microns, 30-70 microns, 30-60 microns, 30-50 microns, 40-100 microns, 40-90 microns, 40-80 microns, 40-70 microns, 40-60 microns, or 40-50 microns. The foregoing are examples only, and the height $H_{ch}$ of the microfluidic channel (e.g., 122) can be in other ranges (e.g., a range defined by any of the endpoints listed above). The height $H_{ch}$ of the microfluidic channel 122 can be selected to be in any of these ranges in regions of the microfluidic channel other than at a proximal opening of an sequestration pen.

In various embodiments of sequestration pens a cross-sectional area of the microfluidic channel (e.g., 122) at a proximal opening (e.g., 234) can be within any of the following ranges: 500-50,000 square microns, 500-40,000 square microns, 500-30,000 square microns, 500-25,000 square microns, 500-20,000 square microns, 500-15,000 square microns, 500-10,000 square microns, 500-7,500 square microns, 500-5,000 square microns, 1,000-25,000 square microns, 1,000-20,000 square microns, 1,000-15,000 square microns, 1,000-10,000 square microns, 1,000-7,500 square microns, 1,000-5,000 square microns, 2,000-20,000 square microns, 2,000-15,000 square microns, 2,000-10,000 square microns, 2,000-7,500 square microns, 2,000-6,000 square microns, 3,000-20,000 square microns, 3,000-15,000 square microns, 3,000-10,000 square microns, 3,000-7,500 square microns, or 3,000 to 6,000 square microns. The foregoing are examples only, and the cross-sectional area of the microfluidic channel (e.g., 122) at a proximal opening (e.g., 234) can be in other ranges (e.g., a range defined by any of the endpoints listed above).

In various embodiments of sequestration pens, the length $L_{con}$ of the connection region (e.g., 236) can be in any of the following ranges: about 1-600 microns, 5-550 microns, 10-500 microns, 15-400 microns, 20-300 microns, 20-500 microns, 40-400 microns, 60-300 microns, 80-200 microns, or about 100-150 microns. The foregoing are examples only, and length $L_{con}$ of a connection region (e.g., 236) can be in a different range than the foregoing examples (e.g., a range defined by any of the endpoints listed above).

In various embodiments of sequestration pens the width $W_{con}$ of a connection region (e.g., 236) at a proximal opening (e.g., 234) can be in any of the following ranges: 20-500 microns, 20-400 microns, 20-300 microns, 20-200 microns, 20-150 microns, 20-100 microns, 20-80 microns, 20-60 microns, 30-400 microns, 30-300 microns, 30-200 microns, 30-150 microns, 30-100 microns, 30-80 microns, 30-60 microns, 40-300 microns, 40-200 microns, 40-150 microns, 40-100 microns, 40-80 microns, 40-60 microns, 50-250 microns, 50-200 microns, 50-150 microns, 50-100 microns, 50-80 microns, 60-200 microns, 60-150 microns, 60-100 microns, 60-80 microns, 70-150 microns, 70-100 microns, and 80-100 microns. The foregoing are examples only, and the width $W_{con}$ of a connection region (e.g., 236) at a proximal opening (e.g., 234) can be different than the foregoing examples (e.g., a range defined by any of the endpoints listed above).

In various embodiments of sequestration pens, the width $W_{con}$ of a connection region (e.g., 236) at a proximal opening (e.g., 234) can be at least as large as the largest dimension of a micro-object (e.g., a biological cell, such as a mammalian cell, an immunological cell, a stem cell, or the like) that the sequestration pen is intended for. For example, the width $W_{con}$ of a connection region 236 at a proximal opening 234 of a sequestration pen that a mammalian cell will be placed into can be in any of the following ranges: about 20 to about 100 microns, about 30 to about 90 microns, about 40 to about 80 microns, about 50 to about 70 microns, or about 60 microns. The foregoing are examples only, and the width $W_{con}$ of a connection region (e.g., 236) at a proximal opening (e.g., 234) can be different than the foregoing examples (e.g., within a range defined by any of the endpoints listed above).

In various embodiments of sequestration pens, a ratio of the length $L_{con}$ of a connection region (e.g., 236) to a width $W_{con}$ of the connection region (e.g., 236) at the proximal opening 234 can be greater than or equal to any of the following ratios: 0.5, 1.0, 1.5, 2.0, 2.5, 3.0, 3.5, 4.0, 4.5, 5.0, 6.0, 7.0, 8.0, 9.0, 10.0, or more. The foregoing are examples only, and the ratio of the length $L_{con}$ of a connection region 236 to a width $W_{con}$ of the connection region 236 at the proximal opening 234 can be different than the foregoing examples.

In various embodiments of microfluidic devices 100, 200, 23, 250, 280, 290, 320, 400, 450, 500, 700, $V_{max}$ can be set around 0.2, 0.3, 0.4, 0.5, 0.6, 0.7, 0.8, 0.9, 1.0, 1.1, 1.2, 1.3, 1.4, 1.5, 2.0, 2.5, 3.0, 3.5, 4.0, 4.5, 5.0, 5.5, 6.0, 6.7, 7.0, 7.5, 8.0, 8.5, 9.0, 10 microliters/sec, or more. The foregoing are examples only, and $V_{max}$ can be different than the foregoing examples (e.g., within a range defined by any of the endpoints listed above).

In various embodiments of microfluidic devices having sequestration pens, the volume of an isolation region (e.g., 240) of a sequestration pen can be, for example, at least $1\times10^5$, $2\times10^5$, $3\times10^5$, $4\times10^5$, $5\times10^5$, $6\times10^5$, $7\times10^5$, $8\times10^5$, $9\times10^5$, $1.0\times10^6$, $1.1\times10^6$, $1.2\times10^6$, $1.3\times10^6$, $1.4\times10^6$, $1.5\times10^7$, $1.6\times10^7$, $1.7\times10^7$, $1.8\times10^7$, $1.9\times10^7$, $2.0\times10^7$ cubic microns, or more. In some embodiments, the volume of an isolation region of a sequestration pen can be within a range defined by any two of the foregoing endpoints (e.g., between about $3\times10^5$ and about $1\times10^6$ cubic microns, between about $8\times10^5$ and about $1.5\times10^6$ cubic microns, or between about $1.3\times10^6$ and $2.0\times10^6$ cubic microns). In various embodiments, the volume of a sequestration pen may be about $3\times10^5$, $4\times10^5$, $5\times10^5$, $6\times10^5$, $7\times10^5$, $8\times10^5$, $9\times10^5$, $1\times10^6$, $1.1\times10^6$, $1.2\times10^6$, $1.3\times10^6$, $1.4\times10^6$, $1.5\times10^6$, $1.6\times10^6$, $1.7\times10^6$, $1.8\times10^6$, $1.9\times10^6$, $2.0\times10^6$, $2.5\times10^6$, $3.0\times10^6$, $3.5\times10^7$, $4.0\times10^7$, $4.5\times10^7$, or about $5.0\times10^7$ cubic microns, or more. In some embodiments, the volume of a sequestration pen can be within a range defined by any two of the foregoing endpoints (e.g., between about $5\times10^5$ and about $1\times10^6$ cubic microns, between about $1\times10^6$ and about $1.5\times10^6$ cubic microns, or between about $1.5\times10^6$ and $2.0\times10^6$ cubic microns). In some embodiments, the volume of a sequestration pen may be about 250 picoliters to about 5 nanoliters, about 500 picoliters to about 1 nanoliter, about 1 nanoliter to about 1.5 nanoliters, about 1.5 nanoliters to about 2.0 nanoliters, about 2.0 nanoliters to about 2.5 nanoliters, about 2.5 nanoliters to about 3.0 nanoliters, about 3.0 nanoliters to about 3.5 nanoliters, or any range defined by two of the foregoing endpoints.

In various embodiment, the microfluidic device has sequestration pens configured as in any of the embodiments discussed herein where the microfluidic device has about 5 to about 10 sequestration pens, about 10 to about 50 sequestration pens, about 100 to about 500 sequestration pens; about 200 to about 1000 sequestration pens, about 500 to about 1500 sequestration pens, about 1000 to about 2000 sequestration pens, or about 1000 to about 3500 sequestration pens. The sequestration pens need not all be the same size and may include a variety of configurations (e.g., different widths, different features within the sequestration pen.

Figure 2G:
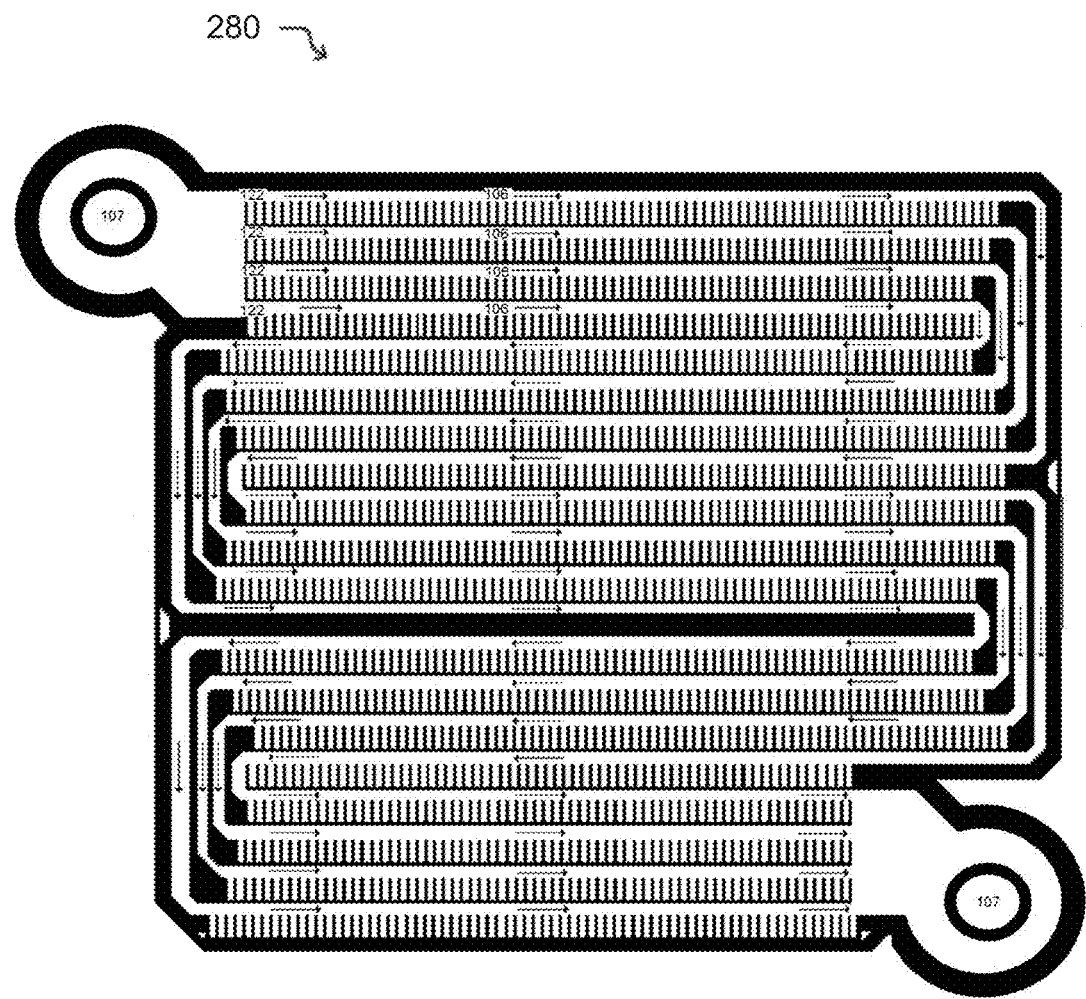
FIG. 2G illustrates a microfluidic device according to an embodiment of the disclosure.

FIG. 2G illustrates a microfluidic device 280 according to one embodiment. The microfluidic device 280 is illustrated in FIG. 2G is a stylized diagram of a microfluidic device 100. In practice the microfluidic device 280 and its constituent circuit elements (e.g. channels 122 and sequestration pens 128) would have the dimensions discussed herein. The microfluidic circuit 120 illustrated in FIG. 2G has two ports 107, four distinct channels 122 and four distinct flow paths 106. The microfluidic device 280 further comprises a plurality of sequestration pens opening off of each channel 122. In the microfluidic device illustrated in FIG. 2G, the sequestration pens have a geometry similar to the pens illustrated in FIG. 2C and thus, have both connection regions and isolation regions. Accordingly, the microfluidic circuit 120 includes both swept regions (e.g. channels 122 and portions of the connection regions 236 within the maximum penetration depth $D_p$ of the secondary flow 244) and non-swept regions (e.g. isolation regions 240 and portions of the connection regions 236 not within the maximum penetration depth $D_p$ of the secondary flow 244).

Figure 3A:
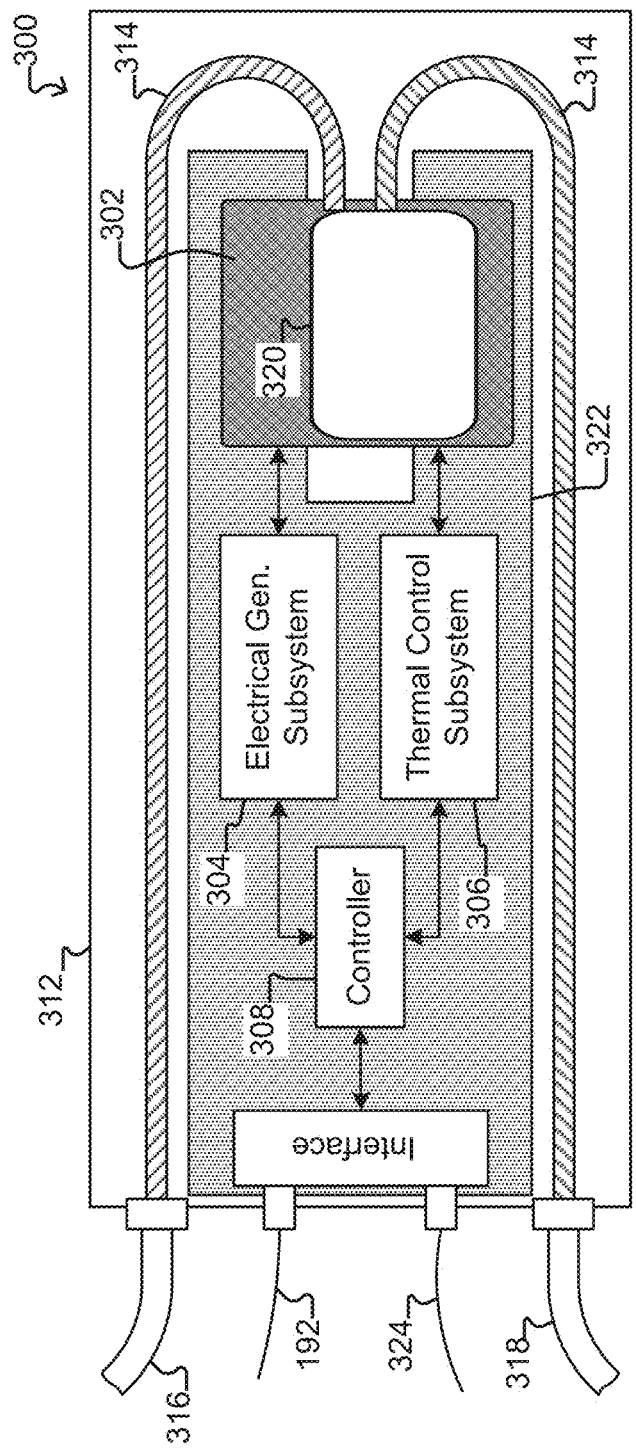
FIG. 3A illustrates a specific example of a system for use with a microfluidic device and associated control equipment according to some embodiments of the disclosure.
Figure 3B:
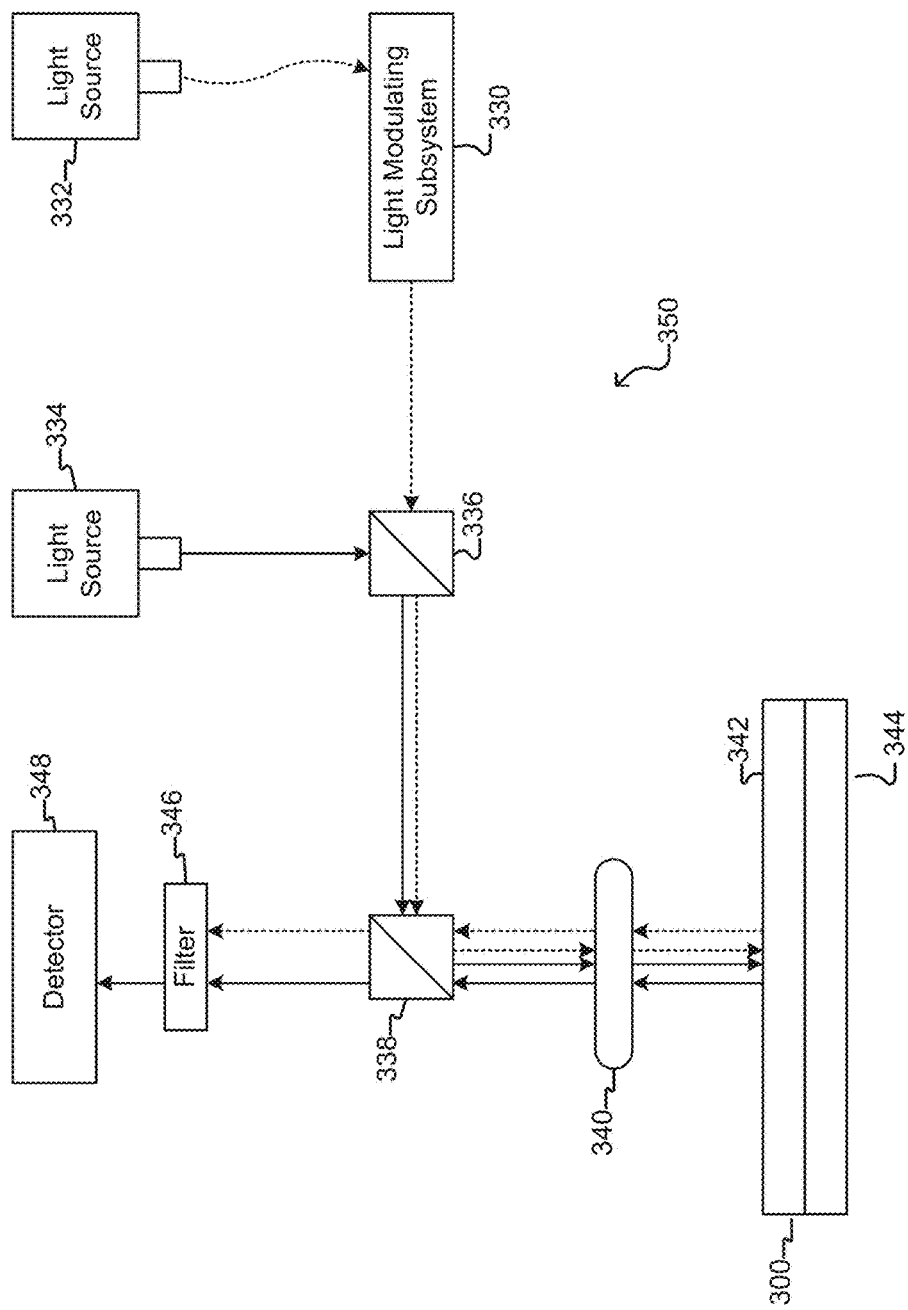
FIG. 3B illustrates an imaging device according to some embodiments of the disclosure.

FIGS. 3A through 3B shows various embodiments of system 150 which can be used to operate and observe microfluidic devices (e.g. 100, 200, 230, 250, 280, 290, 300) according to the present disclosure. As illustrated in FIG. 3A, the system 150 can include a structure ("nest") 300 configured to hold a microfluidic device 100 (not shown), or any other microfluidic device described herein. The nest 300 can include a socket 302 capable of interfacing with the microfluidic device 320 (e.g., an optically-actuated electrokinetic device 100) and providing electrical connections from power source 192 to microfluidic device 320. The nest 300 can further include an integrated electrical signal generation subsystem 304. The electrical signal generation subsystem 304 can be configured to supply a biasing voltage to socket 302 such that the biasing voltage is applied across a pair of electrodes in the microfluidic device 320 when it is being held by socket 302. Thus, the electrical signal generation subsystem 304 can be part of power source 192. The ability to apply a biasing voltage to microfluidic device 320 does not mean that a biasing voltage will be applied at all times when the microfluidic device 320 is held by the socket 302. Rather, in most cases, the biasing voltage will be applied intermittently, e.g., only as needed to facilitate the generation of electrokinetic forces, such as dielectrophoresis or electro-wetting, in the microfluidic device 320.

As illustrated in FIG. 3A, the nest 300 can include a printed circuit board assembly (PCBA) 322. The electrical signal generation subsystem 304 can be mounted on and electrically integrated into the PCBA 322. The exemplary support includes socket 302 mounted on PCBA 322, as well.

Typically, the electrical signal generation subsystem 304 will include a waveform generator (not shown). The electrical signal generation subsystem 304 can further include an oscilloscope (not shown) and/or a waveform amplification circuit (not shown) configured to amplify a waveform received from the waveform generator. The oscilloscope, if present, can be configured to measure the waveform supplied to the microfluidic device 320 held by the socket 302. In certain embodiments, the oscilloscope measures the waveform at a location proximal to the microfluidic device 320 (and distal to the waveform generator), thus ensuring greater accuracy in measuring the waveform actually applied to the device. Data obtained from the oscilloscope measurement can be, for example, provided as feedback to the waveform generator, and the waveform generator can be configured to adjust its output based on such feedback. An example of a suitable combined waveform generator and oscilloscope is the Red Pitaya™.

In certain embodiments, the nest 300 further comprises a controller 308, such as a microprocessor used to sense and/or control the electrical signal generation subsystem 304. Examples of suitable microprocessors include the Arduino™ microprocessors, such as the Arduino Nano™. The controller 308 may be used to perform functions and analysis or may communicate with an external master controller 154 (shown in FIG. 1A) to perform functions and analysis. In the embodiment illustrated in FIG. 3A the controller 308 communicates with a master controller 154 through an interface 310 (e.g., a plug or connector).

In some embodiments, the nest 300 can comprise an electrical signal generation subsystem 304 comprising a Red Pitaya™ waveform generator/oscilloscope unit ("Red Pitaya unit") and a waveform amplification circuit that amplifies the waveform generated by the Red Pitaya unit and passes the amplified voltage to the microfluidic device 100. In some embodiments, the Red Pitaya unit is configured to measure the amplified voltage at the microfluidic device 320 and then adjust its own output voltage as needed such that the measured voltage at the microfluidic device 320 is the desired value. In some embodiments, the waveform amplification circuit can have a +6.5V to −6.5V power supply generated by a pair of DC-DC converters mounted on the PCBA 322, resulting in a signal of up to 13 Vpp at the microfluidic device 100.

As illustrated in FIG. 3A, the support structure 300 (e.g., nest) can further include a thermal control subsystem 306. The thermal control subsystem 306 can be configured to regulate the temperature of microfluidic device 320 held by the support structure 300. For example, the thermal control subsystem 306 can include a Peltier thermoelectric device (not shown) and a cooling unit (not shown). The Peltier thermoelectric device can have a first surface configured to interface with at least one surface of the microfluidic device 320. The cooling unit can be, for example, a cooling block (not shown), such as a liquid-cooled aluminum block. A second surface of the Peltier thermoelectric device (e.g., a surface opposite the first surface) can be configured to interface with a surface of such a cooling block. The cooling block can be connected to a fluidic path 314 configured to circulate cooled fluid through the cooling block. In the embodiment illustrated in FIG. 3A, the support structure 300 comprises an inlet 316 and an outlet 318 to receive cooled fluid from an external reservoir (not shown), introduce the cooled fluid into the fluidic path 314 and through the cooling block, and then return the cooled fluid to the external reservoir. In some embodiments, the Peltier thermoelectric device, the cooling unit, and/or the fluidic path 314 can be mounted on a casing 312 of the support structure 300. In some embodiments, the thermal control subsystem 306 is configured to regulate the temperature of the Peltier thermoelectric device so as to achieve a target temperature for the microfluidic device 320. Temperature regulation of the Peltier thermoelectric device can be achieved, for example, by a thermoelectric power supply, such as a Pololu™ thermoelectric power supply (Pololu Robotics and Electronics Corp.). The thermal control subsystem 306 can include a feedback circuit, such as a temperature value provided by an analog circuit. Alternatively, the feedback circuit can be provided by a digital circuit.

In some embodiments, the nest 300 can include a thermal control subsystem 306 with a feedback circuit that is an analog voltage divider circuit (not shown) which includes a resistor (e.g., with resistance 1 kOhm+/−0.1%, temperature coefficient +/−0.02 ppm/C0) and a NTC thermistor (e.g., with nominal resistance 1 kOhm+/−0.01%). In some instances, the thermal control subsystem 306 measures the voltage from the feedback circuit and then uses the calculated temperature value as input to an on-board PID control loop algorithm. Output from the PID control loop algorithm can drive, for example, both a directional and a pulse-width-modulated signal pin on a Pololu™ motor drive (not shown) to actuate the thermoelectric power supply, thereby controlling the Peltier thermoelectric device.

The nest 300 can include a serial port 324 which allows the microprocessor of the controller 308 to communicate with an external master controller 154 via the interface 310 (not shown). In addition, the microprocessor of the controller 308 can communicate (e.g., via a Plink tool (not shown))

with the electrical signal generation subsystem 304 and thermal control subsystem 306. Thus, via the combination of the controller 308, the interface 310, and the serial port 324, the electrical signal generation subsystem 304 and the thermal control subsystem 306 can communicate with the external master controller 154. In this manner, the master controller 154 can, among other things, assist the electrical signal generation subsystem 304 by performing scaling calculations for output voltage adjustments. A Graphical User Interface (GUI) (not shown) provided via a display device 170 coupled to the external master controller 154, can be configured to plot temperature and waveform data obtained from the thermal control subsystem 306 and the electrical signal generation subsystem 304, respectively. Alternatively, or in addition, the GUI can allow for updates to the controller 308, the thermal control subsystem 306, and the electrical signal generation subsystem 304.

As discussed above, system 150 can include an imaging device. In some embodiments, the imaging device comprises a light modulating subsystem 330 (See FIG. 3B). The light modulating subsystem 330 can include a digital mirror device (DMD) or a microshutter array system (MSA), either of which can be configured to receive light from a light source 332 and transmits a subset of the received light into an optical train of microscope 350. Alternatively, the light modulating subsystem 330 can include a device that produces its own light (and thus dispenses with the need for a light source 332), such as an organic light emitting diode display (OLED), a liquid crystal on silicon (LCOS) device, a ferroelectric liquid crystal on silicon device (FLCOS), or a transmissive liquid crystal display (LCD). The light modulating subsystem 330 can be, for example, a projector. Thus, the light modulating subsystem 330 can be capable of emitting both structured and unstructured light. In certain embodiments, imaging module 164 and/or motive module 162 of system 150 can control the light modulating subsystem 330.

In certain embodiments, the imaging device further comprises a microscope 350. In such embodiments, the nest 300 and light modulating subsystem 330 can be individually configured to be mounted on the microscope 350. The microscope 350 can be, for example, a standard research-grade light microscope or fluorescence microscope. Thus, the nest 300 can be configured to be mounted on the stage 344 of the microscope 350 and/or the light modulating subsystem 330 can be configured to mount on a port of microscope 350. In other embodiments, the nest 300 and the light modulating subsystem 330 described herein can be integral components of microscope 350.

In certain embodiments, the microscope 350 can further include one or more detectors 348. In some embodiments, the detector 348 is controlled by the imaging module 164. The detector 348 can include an eye piece, a charge-coupled device (CCD), a camera (e.g., a digital camera), or any combination thereof. If at least two detectors 348 are present, one detector can be, for example, a fast-frame-rate camera while the other detector can be a high sensitivity camera. Furthermore, the microscope 350 can include an optical train configured to receive reflected and/or emitted light from the microfluidic device 320 and focus at least a portion of the reflected and/or emitted light on the one or more detectors 348. The optical train of the microscope can also include different tube lenses (not shown) for the different detectors, such that the final magnification on each detector can be different.

In certain embodiments, the imaging device is configured to use at least two light sources. For example, a first light source 332 can be used to produce structured light (e.g., via the light modulating subsystem 330) and a second light source 334 can be used to provide unstructured light. The first light source 332 can produce structured light for optically-actuated electrokinesis and/or fluorescent excitation, and the second light source 334 can be used to provide bright field illumination. In these embodiments, the motive module 164 can be used to control the first light source 332 and the imaging module 164 can be used to control the second light source 334. The optical train of the microscope 350 can be configured to (1) receive structured light from the light modulating subsystem 330 and focus the structured light on at least a first region in a microfluidic device, such as an optically-actuated electrokinetic device, when the device is being held by the nest 300, and (2) receive reflected and/or emitted light from the microfluidic device and focus at least a portion of such reflected and/or emitted light onto detector 348. The optical train can be further configured to receive unstructured light from a second light source and focus the unstructured light on at least a second region of the microfluidic device, when the device is held by the nest 300. In certain embodiments, the first and second regions of the microfluidic device can be overlapping regions. For example, the first region can be a subset of the second region. In other embodiments, the second light source 334 may additionally or alternatively include a laser, which may have any suitable wavelength of light. The representation of the optical system shown in FIG. 3B is a schematic representation only, and the optical system may include additional filters, notch filters, lenses and the like. When the second light source 334 includes one or more light source(s) for brightfield and/or fluorescent excitation, as well as laser illumination the physical arrangement of the light source(s) may vary from that shown in FIG. 3B, and the laser illumination may be introduced at any suitable physical location within the optical system. The schematic locations of light source 334 and light source 332/light modulating subsystem 330 may be interchanged as well.

In FIG. 3B, the first light source 332 is shown supplying light to a light modulating subsystem 330, which provides structured light to the optical train of the microscope 350 of system 355 (not shown). The second light source 334 is shown providing unstructured light to the optical train via a beam splitter 336. Structured light from the light modulating subsystem 330 and unstructured light from the second light source 334 travel from the beam splitter 336 through the optical train together to reach a second beam splitter (or dichroic filter 338, depending on the light provided by the light modulating subsystem 330), where the light gets reflected down through the objective 336 to the sample plane 342. Reflected and/or emitted light from the sample plane 342 then travels back up through the objective 340, through the beam splitter and/or dichroic filter 338, and to a dichroic filter 346. Only a fraction of the light reaching dichroic filter 346 passes through and reaches the detector 348.

In some embodiments, the second light source 334 emits blue light. With an appropriate dichroic filter 346, blue light reflected from the sample plane 342 is able to pass through dichroic filter 346 and reach the detector 348. In contrast, structured light coming from the light modulating subsystem 330 gets reflected from the sample plane 342, but does not pass through the dichroic filter 346. In this example, the dichroic filter 346 is filtering out visible light having a wavelength longer than 495 nm. Such filtering out of the light from the light modulating subsystem 330 would only be complete (as shown) if the light emitted from the light modulating subsystem did not include any wavelengths shorter than 495 nm. In practice, if the light coming from the light modulating subsystem 330 includes wavelengths shorter than 495 nm (e.g., blue wavelengths), then some of the light from the light modulating subsystem would pass through filter 346 to reach the detector 348. In such an embodiment, the filter 346 acts to change the balance between the amount of light that reaches the detector 348 from the first light source 332 and the second light source 334. This can be beneficial if the first light source 332 is significantly stronger than the second light source 334. In other embodiments, the second light source 334 can emit red light, and the dichroic filter 346 can filter out visible light other than red light (e.g., visible light having a wavelength shorter than 650 nm).

Coating solutions and coating agents. Without intending to be limited by theory, maintenance of a biological micro-object (e.g., a biological cell) within a microfluidic device (e.g., a DEP-configured and/or EW-configured microfluidic device) may be facilitated (i.e., the biological micro-object exhibits increased viability, greater expansion and/or greater portability within the microfluidic device) when at least one or more inner surfaces of the microfluidic device have been conditioned or coated so as to present a layer of organic and/or hydrophilic molecules that provides the primary interface between the microfluidic device and biological micro-object(s) maintained therein. In some embodiments, one or more of the inner surfaces of the microfluidic device (e.g. the inner surface of the electrode activation substrate of a DEP-configured microfluidic device, the cover of the microfluidic device, and/or the surfaces of the circuit material) may be treated with or modified by a coating solution and/or coating agent to generate the desired layer of organic and/or hydrophilic molecules.

The coating may be applied before or after introduction of biological micro-object(s), or may be introduced concurrently with the biological micro-object(s). In some embodiments, the biological micro-object(s) may be imported into the microfluidic device in a fluidic medium that includes one or more coating agents. In other embodiments, the inner surface(s) of the microfluidic device (e.g., a DEP-configured microfluidic device) are treated or "primed" with a coating solution comprising a coating agent prior to introduction of the biological micro-object(s) into the microfluidic device.

In some embodiments, at least one surface of the microfluidic device includes a coating material that provides a layer of organic and/or hydrophilic molecules suitable for maintenance and/or expansion of biological micro-object(s) (e.g. provides a conditioned surface as described below). In some embodiments, substantially all the inner surfaces of the microfluidic device include the coating material. The coated inner surface(s) may include the surface of a flow region (e.g., channel), chamber, or sequestration pen, or a combination thereof. In some embodiments, each of a plurality of sequestration pens has at least one inner surface coated with coating materials. In other embodiments, each of a plurality of flow regions or channels has at least one inner surface coated with coating materials. In some embodiments, at least one inner surface of each of a plurality of sequestration pens and each of a plurality of channels is coated with coating materials.

Coating agent/Solution. Any convenient coating agent/coating solution can be used, including but not limited to: serum or serum factors, bovine serum albumin (BSA), polymers, detergents, enzymes, and any combination thereof Polymer-based coating materials. The at least one inner surface may include a coating material that comprises a polymer. The polymer may be covalently or non-covalently bound (or may be non-specifically adhered) to the at least one surface. The polymer may have a variety of structural motifs, such as found in block polymers (and copolymers), star polymers (star copolymers), and graft or comb polymers (graft copolymers), all of which may be suitable for the methods disclosed herein.

The polymer may include a polymer including alkylene ether moieties. A wide variety of alkylene ether containing polymers may be suitable for use in the microfluidic devices described herein. One non-limiting exemplary class of alkylene ether containing polymers are amphiphilic nonionic block copolymers which include blocks of polyethylene oxide (PEO) and polypropylene oxide (PPO) subunits in differing ratios and locations within the polymer chain. Pluronic® polymers (BASF) are block copolymers of this type and are known in the art to be suitable for use when in contact with living cells. The polymers may range in average molecular mass $M_w$ from about 2000 Da to about 20 KDa. In some embodiments, the PEO-PPO block copolymer can have a hydrophilic-lipophilic balance (HLB) greater than about 10 (e.g. 12-18). Specific Pluronic® polymers useful for yielding a coated surface include Pluronic® L44, L64, P85, and F127 (including F127NF). Another class of alkylene ether containing polymers is polyethylene glycol (PEG $M_w$<100,000 Da) or alternatively polyethylene oxide (PEO, $M_w$>100,000). In some embodiments, a PEG may have an $M_w$ of about 1000 Da, 5000 Da, 10,000 Da or 20,000 Da.

In other embodiments, the coating material may include a polymer containing carboxylic acid moieties. The carboxylic acid subunit may be an alkyl, alkenyl or aromatic moiety containing subunit. One non-limiting example is polylactic acid (PLA). In other embodiments, the coating material may include a polymer containing phosphate moieties, either at a terminus of the polymer backbone or pendant from the backbone of the polymer. In yet other embodiments, the coating material may include a polymer containing sulfonic acid moieties. The sulfonic acid subunit may be an alkyl, alkenyl or aromatic moiety containing subunit. One non-limiting example is polystyrene sulfonic acid (PSSA) or polyanethole sulfonic acid. In further embodiments, the coating material may include a polymer including amine moieties. The polyamino polymer may include a natural polyamine polymer or a synthetic polyamine polymer. Examples of natural polyamines include spermine, spermidine, and putrescine.

In other embodiments, the coating material may include a polymer containing saccharide moieties. In a non-limiting example, polysaccharides such as xanthan gum or dextran may be suitable to form a material which may reduce or prevent cell sticking in the microfluidic device. For example, a dextran polymer having a size about 3 kDa may be used to provide a coating material for a surface within a microfluidic device.

In other embodiments, the coating material may include a polymer containing nucleotide moieties, i.e. a nucleic acid, which may have ribonucleotide moieties or deoxyribonucleotide moieties, providing a polyelectrolyte surface. The nucleic acid may contain only natural nucleotide moieties or may contain unnatural nucleotide moieties which comprise nucleobase, ribose or phosphate moiety analogs such as 7-deazaadenine, pentose, methyl phosphonate or phosphorothioate moieties without limitation.

In yet other embodiments, the coating material may include a polymer containing amino acid moieties. The polymer containing amino acid moieties may include a natural amino acid containing polymer or an unnatural amino acid containing polymer, either of which may include a peptide, a polypeptide or a protein. In one non-limiting example, the protein may be bovine serum albumin (BSA) and/or serum (or a combination of multiple different sera) comprising albumin and/or one or more other similar proteins as coating agents. The serum can be from any convenient source, including but not limited to fetal calf serum, sheep serum, goat serum, horse serum, and the like. In certain embodiments, BSA in a coating solution is present in a range of form about 1 mg/mL to about 100 mg/mL, including 5 mg/mL, 10 mg/mL, 20 mg/mL, 30 mg/mL, 40 mg/mL, 50 mg/mL, 60 mg/mL, 70 mg/mL, 80 mg/mL, 90 mg/mL, or more, or anywhere in between. In certain embodiments, serum in a coating solution may be present in a range of from about 20% (v/v) to about 50% v/v, including 25%, 30%, 35%, 40%, 45%, or more or anywhere in between. In some embodiments, BSA may be present as a coating agent in a coating solution at: 5 mg/mL, whereas in other embodiments, BSA may be present as a coating agent in a coating solution at 70 mg/mL. In certain embodiments, serum is present as a coating agent in a coating solution at 30%. In some embodiments, an extracellular matrix (ECM) protein may be provided within the coating material for optimized cell adhesion to foster cell growth. A cell matrix protein, which may be included in a coating material, can include, but is not limited to, a collagen, an elastin, an RGD-containing peptide (e.g. a fibronectin), or a laminin. In yet other embodiments, growth factors, cytokines, hormones or other cell signaling species may be provided within the coating material of the microfluidic device.

In some embodiments, the coating material may include a polymer containing more than one of alkylene oxide moieties, carboxylic acid moieties, sulfonic acid moieties, phosphate moieties, saccharide moieties, nucleotide moieties, or amino acid moieties. In other embodiments, the polymer-conditioned surface may include a mixture of more than one polymer each having alkylene oxide moieties, carboxylic acid moieties, sulfonic acid moieties, phosphate moieties, saccharide moieties, nucleotide moieties, and/or amino acid moieties, which may be independently or simultaneously incorporated into the coating material.

Covalently linked coating materials. In some embodiments, the at least one inner surface includes covalently linked molecules that provide a layer of organic and/or hydrophilic molecules suitable for maintenance/expansion of biological micro-object(s) within the microfluidic device, providing a conditioned surface for such cells.

The covalently linked molecules include a linking group, wherein the linking group is covalently linked to one or more surfaces of the microfluidic device, as described below. The linking group is also covalently linked to a moiety configured to provide a layer of organic and/or hydrophilic molecules suitable for maintenance/expansion of biological micro-object(s).

In some embodiments, the covalently linked moiety configured to provide a layer of organic and/or hydrophilic molecules suitable for maintenance/expansion of biological micro-object(s) may include alkyl or fluoroalkyl (which includes perfluoroalkyl) moieties; mono- or polysaccharides (which may include but is not limited to dextran); alcohols (including but not limited to propargyl alcohol); polyalcohols, including but not limited to polyvinyl alcohol; alkylene ethers, including but not limited to polyethylene glycol; polyelectrolytes (including but not limited to polyacrylic acid or polyvinyl phosphonic acid); amino groups (including derivatives thereof, such as, but not limited to alkylated amines, hydroxyalkylated amino group, guanidinium, and heterocylic groups containing an unaromatized nitrogen ring atom, such as, but not limited to morpholinyl or piperazinyl); carboxylic acids including but not limited to propiolic acid (which may provide a carboxylate anionic surface); phosphonic acids, including but not limited to ethynyl phosphonic acid (which may provide a phosphonate anionic surface); sulfonate anions; carboxybetaines; sulfobetaines; sulfamic acids; or amino acids.

In various embodiments, the covalently linked moiety configured to provide a layer of organic and/or hydrophilic molecules suitable for maintenance/expansion of biological micro-objects(s) in the microfluidic device may include non-polymeric moieties such as an alkyl moiety, a substituted alkyl moiety, such as a fluoroalkyl moiety (including but not limited to a perfluoroalkyl moiety), amino acid moiety, alcohol moiety, amino moiety, carboxylic acid moiety, phosphonic acid moiety, sulfonic acid moiety, sulfamic acid moiety, or saccharide moiety. Alternatively, the covalently linked moiety may include polymeric moieties, which may be any of the moieties described above.

In some embodiments, the covalently linked alkyl moiety may comprise carbon atoms forming a linear chain (e.g., a linear chain of at least 10 carbons, or at least 14, 16, 18, 20, 22, or more carbons) and may be an unbranched alkyl moiety. In some embodiments, the alkyl group may include a substituted alkyl group (e.g., some of the carbons in the alkyl group can be fluorinated or perfluorinated). In some embodiments, the alkyl group may include a first segment, which may include a perfluoroalkyl group, joined to a second segment, which may include a non-substituted alkyl group, where the first and second segments may be joined directly or indirectly (e.g., by means of an ether linkage). The first segment of the alkyl group may be located distal to the linking group, and the second segment of the alkyl group may be located proximal to the linking group.

In other embodiments, the covalently linked moiety may include at least one amino acid, which may include more than one type of amino acid. Thus, the covalently linked moiety may include a peptide or a protein. In some embodiments, the covalently linked moiety may include an amino acid which may provide a zwitterionic surface to support cell growth, viability, portability, or any combination thereof.

In other embodiments, the covalently linked moiety may include at least one alkylene oxide moiety, and may include any alkylene oxide polymer as described above. One useful class of alkylene ether containing polymers is polyethylene glycol (PEG $M_w$<100,000 Da) or alternatively polyethylene oxide (PEO, $M_w$>100,000). In some embodiments, a PEG may have an $M_w$ of about 1000 Da, 5000 Da, 10,000 Da or 20,000 Da.

The covalently linked moiety may include one or more saccharides. The covalently linked saccharides may be mono-, di-, or polysaccharides. The covalently linked saccharides may be modified to introduce a reactive pairing moiety which permits coupling or elaboration for attachment to the surface. Exemplary reactive pairing moieties may include aldehyde, alkyne or halo moieties. A polysaccharide may be modified in a random fashion, wherein each of the saccharide monomers may be modified or only a portion of the saccharide monomers within the polysaccharide are modified to provide a reactive pairing moiety that may be coupled directly or indirectly to a surface. One exemplar may include a dextran polysaccharide, which may be coupled indirectly to a surface via an unbranched linker.

The covalently linked moiety may include one or more amino groups. The amino group may be a substituted amine moiety, guanidine moiety, nitrogen-containing heterocyclic moiety or heteroaryl moiety. The amino containing moieties may have structures permitting pH modification of the environment within the microfluidic device, and optionally, within the sequestration pens and/or flow regions (e.g., channels).

The coating material providing a conditioned surface may comprise only one kind of covalently linked moiety or may include more than one different kind of covalently linked moiety. For example, the fluoroalkyl conditioned surfaces (including perfluoroalkyl) may have a plurality of covalently linked moieties which are all the same, e.g., having the same linking group and covalent attachment to the surface, the same overall length, and the same number of fluoromethylene units comprising the fluoroalkyl moiety. Alternatively, the coating material may have more than one kind of covalently linked moiety attached to the surface. For example, the coating material may include molecules having covalently linked alkyl or fluoroalkyl moieties having a specified number of methylene or fluoromethylene units and may further include a further set of molecules having charged moieties covalently attached to an alkyl or fluoroalkyl chain having a greater number of methylene or fluoromethylene units, which may provide capacity to present bulkier moieties at the coated surface. In this instance, the first set of molecules having different, less sterically demanding termini and fewer backbone atoms can help to functionalize the entire substrate surface and thereby prevent undesired adhesion or contact with the silicon/silicon oxide, hafnium oxide or alumina making up the substrate itself. In another example, the covalently linked moieties may provide a zwitterionic surface presenting alternating charges in a random fashion on the surface.

Conditioned surface properties. Aside from the composition of the conditioned surface, other factors such as physical thickness of the coating material can impact DEP force. Various factors can alter the physical thickness of the coating material, such as the manner in which the coating material is deposited or reacted with the substrate (e.g. vapor deposition, liquid phase deposition, spin coating, flooding, and electrostatic coating). In some embodiments, the conditioned surface has a thickness of less than 10 nm (e.g., in the range of about 1 nm to about 10 nm, about 1 nm to about 7 nm, about 1nm to about 5 nm, or any individual value therebetween). In other embodiments, the conditioned surface formed by the covalently linked moieties may have a thickness of about 10 nm to about 50 nm. In some embodiments, the covalently linked moieties of the conditioned surface may form a monolayer when covalently linked to the surface of the microfluidic device (e.g., a DEP configured substrate surface) and may have a thickness of less than 10 nm (e.g., less than 5 nm, or about 1.5 to 3.0 nm). Typically, the conditioned surface does not require a perfectly formed monolayer to be suitably functional for operation within a DEP-configured microfluidic device.

The conditioned surface may also have properties that are beneficial in use with biological molecules. For example, a conditioned surface that contains fluorinated (or perfluorinated) carbon chains may reduce the amount of surface fouling. Surface fouling, as used herein, refers to the amount of indiscriminate material deposition on the surface of the microfluidic device, which may include permanent or semi-permanent deposition of biomaterials such as protein and its degradation products, nucleic acids and respective degradation products and the like.

Unitary or Multi-part conditioned surface. The covalently linked coating material may be formed by reaction of a molecule which already contains the moiety configured to provide a layer of organic and/or hydrophilic molecules suitable for maintenance/expansion of biological micro-object(s) in the microfluidic device, as is described below. Alternatively, the covalently linked coating material may be formed in a two-part sequence by coupling the moiety configured to provide a layer of organic and/or hydrophilic molecules suitable for maintenance/expansion of biological micro-object(s) to a surface modifying ligand that itself has been covalently linked to the surface.

Methods of preparing a covalently linked coating material. In some embodiments, a coating material that is covalently linked to the surface of a microfluidic device (e.g., including at least one surface of the sequestration pens and/or flow regions) has a structure of Formula 1 or Formula 2. When the coating material is introduced to the surface in one step, it has a structure of Formula 1, while when the coating material is introduced in a multiple step process, it has a structure of Formula 2.

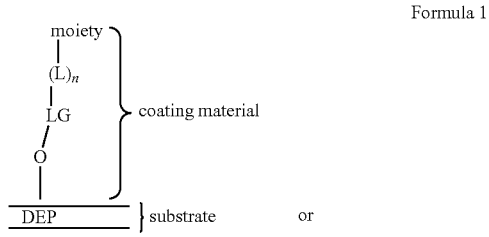

Formula 1

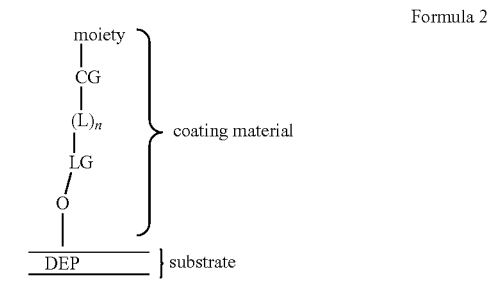

Formula 2

The coating material may be linked covalently to oxides of the surface of a DEP-configured or EW-configured substrate. The DEP- or EW-configured substrate may comprise silicon, silicon oxide, alumina, or hafnium oxide. Oxides may be present as part of the native chemical structure of the substrate or may be introduced as discussed below.

The coating material may be attached to the oxides via a linking group ("LG"), which may be a siloxy or phosphonate ester group formed from the reaction of a siloxane or phosphonic acid group with the oxides. The moiety configured to provide a layer of organic and/or hydrophilic molecules suitable for maintenance/expansion of biological micro-objects(s) in the microfluidic device can be any of the moieties described herein. The linking group LG may be directly or indirectly connected to the moiety configured to provide a layer of organic and/or hydrophilic molecules suitable for maintenance/expansion of biological micro-objects(s) in the microfluidic device. When the linking group LG is directly connected to the moiety, optional linker ("L") is not present and n is 0. When the linking group LG is indirectly connected to the moiety, linker L is present and n is 1. The linker L may have a linear portion where a backbone of the linear portion may include 1 to 200 non-hydrogen atoms selected from any combination of silicon, carbon, nitrogen, oxygen, sulfur and phosphorus atoms, subject to chemical bonding limitations as is known in the art. It may be interrupted with any combination of one or more moieties chosen from ether, amino, carbonyl, amido, or phosphonate groups, arylene, heteroarylene, or heterocyclic groups. In some embodiments, the backbone of the linker L may include 10 to 20 atoms. In other embodiments, the backbone of the linker L may include about 5 atoms to about 200 atoms; about 10 atoms to about 80 atoms; about 10 atoms to about 50 atoms; or about 10 atoms to about 40 atoms. In some embodiments, the backbone atoms are all carbon atoms.

In some embodiments, the moiety configured to provide a layer of organic and/or hydrophilic molecules suitable for maintenance/expansion of biological micro-object(s) may be added to the surface of the substrate in a multi-step process, and has a structure of Formula 2, as shown above. The moiety may be any of the moieties described above.

In some embodiments, the coupling group CG represents the resultant group from reaction of a reactive moiety $R_x$ and a reactive pairing moiety $R_{px}$ (i.e., a moiety configured to react with the reactive moiety $R_x$). For example, one typical coupling group CG may include a carboxamidyl group, which is the result of the reaction of an amino group with a derivative of a carboxylic acid, such as an activated ester, an acid chloride or the like. Other CG may include a triazolylene group, a carboxamidyl, thioamidyl, an oxime, a mercaptyl, a disulfide, an ether, or alkenyl group, or any other suitable group that may be formed upon reaction of a reactive moiety with its respective reactive pairing moiety. The coupling group CG may be located at the second end (i.e., the end proximal to the moiety configured to provide a layer of organic and/or hydrophilic molecules suitable for maintenance/expansion of biological micro-objects(s) in the microfluidic device) of linker L, which may include any combination of elements as described above. In some other embodiments, the coupling group CG may interrupt the backbone of the linker L. When the coupling group CG is triazolylene, it may be the product resulting from a Click coupling reaction and may be further substituted (e.g., a dibenzocylcooctenyl fused triazolylene group).

In some embodiments, the coating material (or surface modifying ligand) is deposited on the inner surfaces of the microfluidic device using chemical vapor deposition. The vapor deposition process can be optionally improved, for example, by pre-cleaning the cover 110, the microfluidic circuit material 116, and/or the substrate (e.g., the inner surface 208 of the electrode activation substrate 206 of a DEP-configured substrate, or a dielectric layer of the support structure 104 of an EW-configured substrate), by exposure to a solvent bath, sonication or a combination thereof. Alternatively, or in addition, such pre-cleaning can include treating the cover 110, the microfluidic circuit material 116, and/or the substrate in an oxygen plasma cleaner, which can remove various impurities, while at the same time introducing an oxidized surface (e.g. oxides at the surface, which may be covalently modified as described herein). Alternatively, liquid-phase treatments, such as a mixture of hydrochloric acid and hydrogen peroxide or a mixture of sulfuric acid and hydrogen peroxide (e.g., piranha solution, which may have a ratio of sulfuric acid to hydrogen peroxide in a range from about 3:1 to about 7:1) may be used in place of an oxygen plasma cleaner.

In some embodiments, vapor deposition is used to coat the inner surfaces of the microfluidic device 200 after the microfluidic device 200 has been assembled to form an enclosure 102 defining a microfluidic circuit 120. Without intending to be limited by theory, depositing such a coating material on a fully-assembled microfluidic circuit 120 may be beneficial in preventing delamination caused by a weakened bond between the microfluidic circuit material 116 and the electrode activation substrate 206 dielectric layer and/or the cover 110. In embodiments where a two-step process is employed the surface modifying ligand may be introduced via vapor deposition as described above, with subsequent introduction of the moiety configured provide a layer of organic and/or hydrophilic molecules suitable for maintenance/expansion of biological micro-object(s). The subsequent reaction may be performed by exposing the surface modified microfluidic device to a suitable coupling reagent in solution.

Figure 2H:
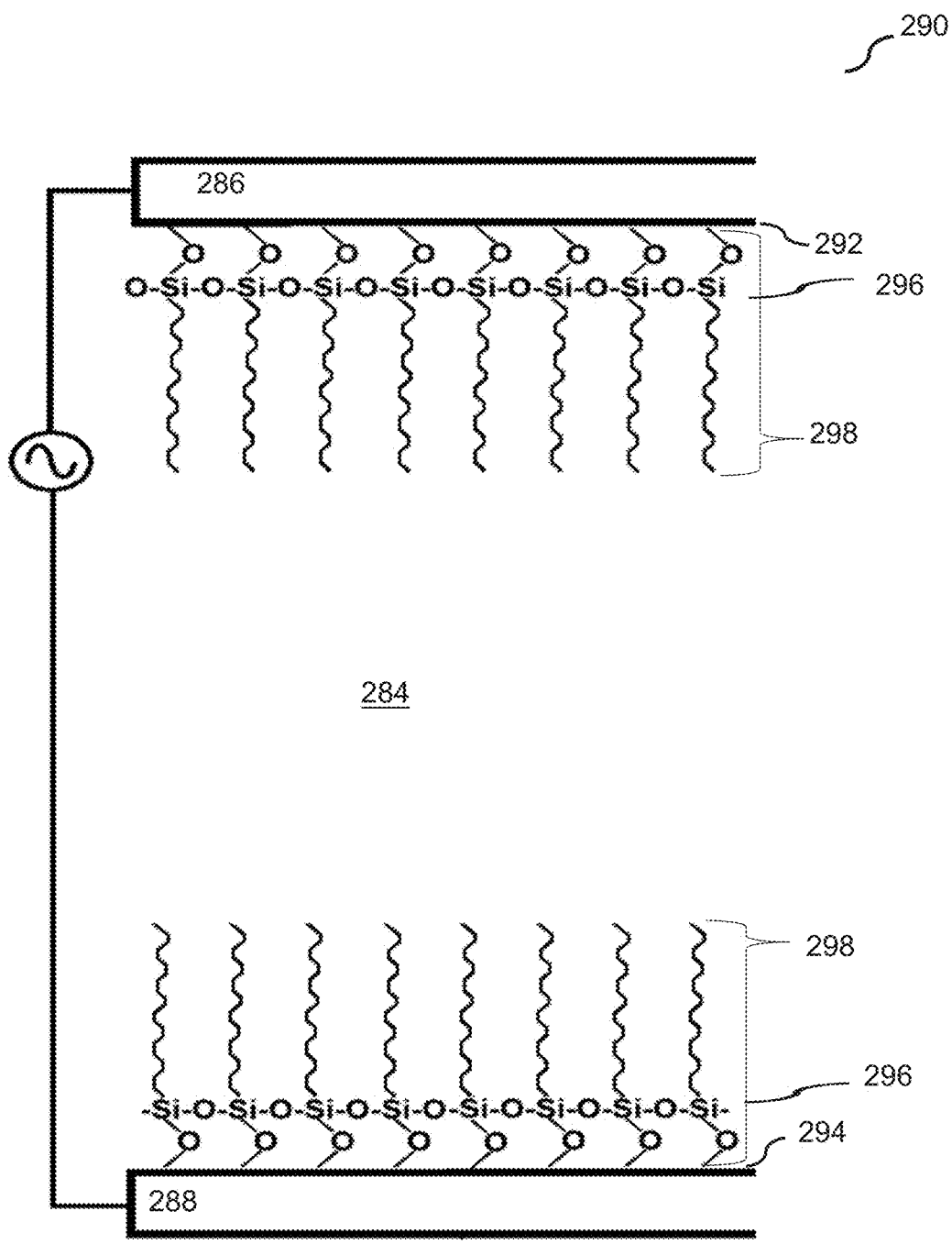
FIG. 2H illustrates a conditioned surface of a microfluidic device according to an embodiment of the disclosure.

FIG. 2H depicts a cross-sectional view of a microfluidic device 290 having an exemplary covalently linked coating material providing a conditioned surface. As illustrated, the coating materials 298 (shown schematically) can comprise a monolayer of densely-packed molecules covalently bound to both the inner surface 294 of a base 286, which may be a DEP substrate, and the inner surface 292 of a cover 288 of the microfluidic device 290. The coating material 298 can be disposed on substantially all inner surfaces 294, 292 proximal to, and facing inwards towards, the enclosure 284 of the microfluidic device 290, including, in some embodiments and as discussed above, the surfaces of microfluidic circuit material (not shown) used to define circuit elements and/or structures within the microfluidic device 290. In alternate embodiments, the coating material 298 can be disposed on only one or some of the inner surfaces of the microfluidic device 290.

In the embodiment shown in FIG. 2H, the coating material 298 can include a monolayer of organosiloxane molecules, each molecule covalently bonded to the inner surfaces 292, 294 of the microfluidic device 290 via a siloxy linker 296. Any of the above-discussed coating materials 298 can be used (e.g. an alkyl-terminated , a fluoroalkyl terminated moiety, a PEG- terminated moiety, a dextran terminated moiety, or a terminal moiety containing positive or negative charges for the organosiloxy moieties), where the terminal moiety is disposed at its enclosure-facing terminus (i.e. the portion of the monolayer of the coating material 298 that is not bound to the inner surfaces 292, 294 and is proximal to the enclosure 284).

In other embodiments, the coating material 298 used to coat the inner surface(s) 292, 294 of the microfluidic device 290 can include anionic, cationic, or zwitterionic moieties, or any combination thereof. Without intending to be limited by theory, by presenting cationic moieties, anionic moieties, and/or zwitterionic moieties at the inner surfaces of the enclosure 284 of the microfluidic circuit 120, the coating material 298 can form strong hydrogen bonds with water molecules such that the resulting water of hydration acts as a layer (or "shield") that separates the biological micro-objects from interactions with non-biological molecules (e.g., the silicon and/or silicon oxide of the substrate). In addition, in embodiments in which the coating material 298 is used in conjunction with coating agents, the anions, cations, and/or zwitterions of the coating material 298 can form ionic bonds with the charged portions of non-covalent coating agents (e.g. proteins in solution) that are present in a medium 180 (e.g. a coating solution) in the enclosure 284.

In still other embodiments, the coating material may comprise or be chemically modified to present a hydrophilic coating agent at its enclosure-facing terminus. In some embodiments, the coating material may include an alkylene ether containing polymer, such as PEG. In some embodiments, the coating material may include a polysaccharide, such as dextran. Like the charged moieties discussed above (e.g., anionic, cationic, and zwitterionic moieties), the hydrophilic coating agent can form strong hydrogen bonds with water molecules such that the resulting water of hydration acts as a layer (or "shield") that separates the biological micro-objects from interactions with non-biological molecules (e.g., the silicon and/or silicon oxide of the substrate).

Further details of appropriate coating treatments and modifications may be found at U.S. Patent Publication No. US2016/0312165, which is incorporated by reference in its entirety.

Additional system components for maintenance of viability of cells within the sequestration pens of the microfluidic device. In order to promote growth and/or expansion of cell populations, environmental conditions conducive to maintaining functional cells may be provided by additional components of the system. For example, such additional components can provide nutrients, cell growth signaling species, pH modulation, gas exchange, temperature control, and removal of waste products from cells. These types of additional components have been described, for example, in U.S. Patent Publication No. US2016/0312165.

Methods, systems, and devices for selecting and/or generating genome-edited cells. The disclosed methods, systems and devices are suitable for selecting and expanding genome-edited cells to create clonal cell populations which can be screened for a desired genotype (e.g., a targeted genome edit, optionally in combination with no off-target modifications to the genome). The disclosed methods, systems and devices are also suitable for performing targeted genome editing or non-targeted genome editing, either of which may include transfection, in cells while they are located within a microfluidic device.

Figure 4:
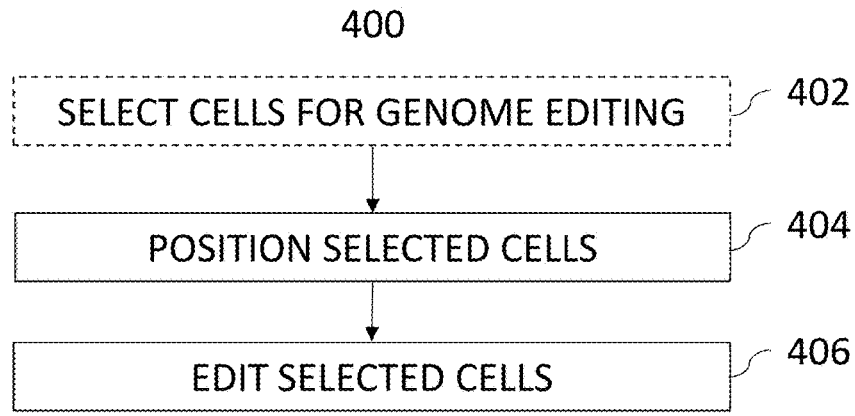
FIG. 4 illustrates steps in a method for genome editing of cells according to some embodiments of the disclosure.

FIG. 4 illustrates steps in an exemplary method of editing the genome of a cell (or cells) within a microfluidic device. The microfluidic device can include a substrate having a dielectrophoresis (DEP) configuration and/or an electro-wetting (EW) configuration. For example, the substrate can have a DEP configuration and, optionally, an EW configuration. The DEP configuration and/or the EW configuration can be optically actuated, at least in part. Thus, for example, the DEP-configured substrate of the microfluidic device, or a portion thereof, can include an optoelectronic tweezer (OET) configuration. Likewise, the EW-configured substrate of the microfluidic device, or a portion thereof, can include an opto-electrowetting (OEW) configuration. Steps that require the positioning of one or more micro-objects (e.g., cells, beads, etc.) can be performed using dielectrophoretic force (e.g. OET force), and/or steps that require the movement of droplets (e.g., which may contain micro-objects) can be performed using electro-wetting force (e.g. OEW force), depending on the embodiment and the configuration of the microfluidic device used. As discussed below, some of the steps in the method may be performed outside of the microfluidic device.

The method of FIG. 4 optionally starts with step 402, the selection of cells for genome editing. Cells can be selected based on a number of different criteria and/or characteristics, including but not limited to: morphology, size, motility (e.g. chemotaxis), production of a protein of interest, reaction to a specific antibody, presence of one or more cell surface markers, ability to differentiate, and/or rate of proliferation. The selection can be, or can include, a negative selection that removes unwanted cells from a starting population of mixed cell types.

Assays to identify various cellular criteria and/or characteristics of cells of interest may be performed within the microfluidic device. Production of a protein of interest may be assayed, for example, as described in U.S. Pat. No. 8,921,055 and U.S. Patent Application Publication Nos. 2015/0151298 and 2016/0160259, the entirety of each of which is incorporated herein by reference. Cell size, morphology, and/or proliferation may be quantified using cell detection algorithms, such as described in U.S. Patent Application Publication No. 2016/0171686, the entirety of which is incorporated herein by reference. In some embodiments, where the cell(s) are selected for transfection based on one or more time-dependent characteristics, such as rate of proliferation, rate of production of an analyte of interest (e.g., a protein) which may or may not be responsive to a stimulus, or motility rate, it may be necessary to maintain the cell(s) within the microfluidic device (e.g., within one or more sequestration pens) for a period of time and/or contact the cell(s) with one or more reagents. In some embodiments, one or more of the cellular criteria and/or characteristics may be monitored in an automated manner.

In some embodiments, it may be necessary to expand the cell(s) within the microfluidic device in order to assay for a cellular criteria and/or characteristic of interest. Likewise, for some assays, such as measurement of an analyte of interest, it may be helpful to expand a cell into a clonal population of cells in order to increase assay signal (e.g., increase the amount of secreted protein to an amount sufficient to quantify). Whether the cell(s) is/are expanded or not, the assay signal can be measured relative to an absolute value or an on-chip control. As used herein, "expanding a cell" refers to the maintenance of a cell in a suitable culture medium for a period of time sufficient for the cell to mitotically divide and produce at least two daughter cells, each of which is viable. Cell culture media suitable for use within a microfluidic device have been described, for example, in U.S. Patent Application Publication No. 2016/0312165, the entire contents of which are incorporated herein by reference.

In some embodiments, the cell(s) may be selected based on one or more characteristics related to previously-performed treatments, such as a previous transfection and/or genome edit, including the successful integration of exogenous DNA into a specific site within the genome of the cell(s) (referred to herein as a "target site") and/or successful deletion of endogenous DNA from a target site within the genome of the cell(s). In some embodiments, the cells selected for genome editing may be homogeneous (i.e., having essentially the same or similar cellular characteristics). In other embodiments, the cells selected for transfection may be heterogeneous (i.e., exhibiting different cellular characteristics).

Depending on the embodiment, the cell(s) may be selected for genome editing based on more than one cellular criteria and/or characteristic. Thus, in some embodiments, two or more selection steps can be performed, each of which may be performed independent of the other(s), within the microfluidic device or prior to loading the cells into the microfluidic device. For example, cells may undergo a first selection using flow-cytometry (or another technique that can be performed outside of the micro-fluidic device, such as positive or negative sorting using magnetic beads), after which the cells can be introduced into the microfluidic device and undergo a second selection based on size, morphology, cell surface marker(s), or the like. The second selection can include using a force, such as a DEP or OET force, to move selected cells away from unselected cells, or vice versa.

In some embodiments, it may be necessary to expand selected cells in order to have a population of cells suitable for genome editing, which can include transfection and various subsequent steps. As discussed below, some methods of transfection (such as electroporation) increase the porosity of cells and thus may damage cells or otherwise impact their viability. In embodiments that use such methods of transfection, it may be necessary to transfect a large number of selected cells in order to obtain a sufficient number of viable transfected cells.

In step 404 of the method of FIG. 4, cells, which may be unselected (if step 402 is skipped), are positioned for transfection. As used herein, the term "transfection" refers to the movement of a nucleic acid construct, which may be part of a genome editing biomolecule, a donor template, or the like, into the interior of a cell. Thus, step 404 can include moving selected cells to a region of the microfluidic device configured for transfection (i.e., a "transfection region" or an "editing region"). In some embodiments, in which the cells are selected for transfection within the microfluidic device (either partially or completely), the selected cells can be moved from a region of the microfluidic device in which the cells are selected (i.e., a "selection region") to the editing region of the microfluidic device. The selection region, for example, could be a microfluidic channel, and the editing region could be a chamber configured for cellular transfection. Alternatively, the selection region can be a chamber in the microfluidic device and the editing region can be a separate chamber in the microfluidic device. In other embodiments, step 404 can include loading already selected cells into the microfluidic device and then moving the cells into the editing region. For example, if the cells are selected for transfection outside of the microfluidic device, the selected cells can be loaded into the microfluidic device and transported directly to the editing region (e.g., via a flow path, such as a microfluidic channel). In still other embodiments, step 404 can include loading the cells (whether selected or not) directly into an editing region of the microfluidic device. Depending on the embodiment and the configuration of the microfluidic device, the cells may be moved using fluid flow, gravity, centrifugal force, DEP force (e.g., OET force), EW force (e.g., OEW force), or any combination thereof, as discussed elsewhere herein.

The editing region can vary according to the embodiment and the type of microfluidic device used. In some embodiments, the editing region comprises a series of chambers, each of which may be configured for genetic modification of a limited number of cells. For example, the editing region may comprise a plurality of sequestration pens, with each sequestration pen configured to promote cellular transfection (as discussed further below). The plurality of sequestration pens may open off of any one of one or more microfluidic channels in the microfluidic device, such as a common microfluidic channel. In other embodiments, the editing region is a large chamber or similar holding region within the microfluidic device, wherein the chamber/holding region is configured to promote cellular transfection (as discussed further below). In still other embodiments, the editing region is located in a first microfluidic device which is specialized for cellular transfection, and the first microfluidic device is connected (e.g., by tubing or some other type of conduit) to a second microfluidic device which is suitable for maintaining, culturing, and/or expanding transfected cells and/or assaying transfected cells for the presence of a desired genetic alteration. As discussed below, depending on the type of transfection performed, the editing region may contain physical features or structures that facilitate transfection of the cells with a genome editing biomolecule.

In some embodiments, particularly embodiments in which the cells are selected either partially or completely within the microfluidic device, step 404 can include separating cells that are not selected for genome editing ("unselected cells") from the selected cells. For example, selected cells may be moved from a selection region to the editing region, while unselected cells are left behind in the selection region. Alternatively, both selected and unselected cells can be moved into the editing region, and then the unselected cells can be moved out of the editing region. Regardless, the unselected cells may be discarded. For example, the unselected cells can be moved to a region of the microfluidic device designated for excess or unwanted cells. Alternatively, the unselected cells can be flushed from the microfluidic device and, optionally, discarded. For example, the microfluidic device can include a selection region that comprises a microfluidic channel and, following movement of the selected cells to the editing region, unselected cells can be flushed out of the channel (and the microfluidic device) with a flow of medium.

In step 406 of the method of FIG. 4, selected cells are edited. Editing may be accomplished in a variety of ways. In various embodiments, editing comprises contacting one or more cells with a genome editing biomolecule, optionally in combination with a donor template. The term "genome editing biomolecule", as used herein, refers to a molecule, complex, or macromolecular assembly which, upon entry into a cell, is capable of facilitating a stable alteration to the genome of the cell. As used herein, a "stable" alteration is one that is retained by daughter cells produced via division of the edited cell (i.e., the cell altered as a result of being contacted by the genome editing biomolecule). A stable alteration can be maintained for at least one, two, three, four, five, six, seven, eight, nine, ten, eleven, twelve, fifteen, twenty, twenty-five, or more cell divisions. In some embodiments, a stable alteration to the genome of a cell includes an insertion and/or deletion of nucleic acid in the nuclear or mitochondrial DNA of the cell. In some embodiments, a stable alteration to the genome of a cell includes an epigenetic change that alters the expression or activity of the nuclear or mitochondrial DNA of the cell in a stable manner. The genome editing biomolecule can be non-covalently associated with, or otherwise mixed with, one or more biological or organic molecules and/or one or more inorganic molecules or ions.

A genome editing biomolecule can comprise, consist of, or consist essentially of a nucleic acid molecule. The nucleic acid molecule can be single-stranded (e.g., single-stranded RNA, DNA, or a combination thereof) or double-stranded (e.g., double-stranded RNA, DNA, or a hybrid thereof). The genome editing biomolecule can comprise one or more expression cassettes, any one of which may comprise the nucleic acid molecule. Alternatively, the genome editing biomolecule can comprise a viral vector which may comprise the nucleic acid molecule. The viral vector can be a vector derived from a lentivirus (e.g., an integrase-deficient lentiviral vector), an adenovirus, or the like.

The genome editing biomolecule can comprise a nuclease, such as an endonuclease, that facilitates alteration of the genome of a cell. For example, the nuclease can cleave DNA, creating a double-strand break which, when repaired by the cell, becomes modified to include an insertion of an exogenous nucleic acid sequence and/or a deletion of an endogenous nucleic acid sequence. The nuclease can function in a site-specific manner, thereby enabling targeted genome editing. As used herein, "targeted genome editing" refers to the introduction of exogenous nucleic acid at a pre-selected target site in the genome of a cell and/or the deletion of endogenous nucleic acid at the pre-selected target site in the genetic material of the cell. In some embodiments, the nuclease is encoded by the genome editing biomolecule. For example, the nuclease can be encoded by a nucleic acid molecule (or expression cassette) comprised by the genome editing biomolecule. Alternatively, the nuclease can be a protein. For example, the nuclease can be complexed with a nucleic acid molecule, and the complex can be comprised by the genome editing biomolecule. In some embodiments, the nuclease can be a nucleic acid-guided endonuclease, and the nucleic acid molecule can be a guide nucleic acid. The nucleic acid-guided endonuclease can be an RNA-guided endonuclease or a DNA-guided endonuclease. Cas9 (e.g., spCas9, stCas9, nmCas9, eSpCas9) and Cpf1 are non-limiting examples of RNA-guided endonucleases that may be used in the disclosed methods. Natronobacterium gregori Argonaute (NgAgo) is a non-limiting example of a DNA-guided endonuclease that may be used in the disclosed methods. In other embodiments, the nuclease can be a Zinc Finger Nuclease (ZNF) or a Transcription Activator-like Effector Nuclease (TALEN), either of which may be associated with FokI. Other nucleases and associated DNA-binding molecules suitable for use in the disclosed methods are known to those skilled in the art. See, for example, Richardson et al., Enhancing homology-directed genome editing by catalytically active and inactive CRISPR-Cas9 using asymmetric donor DNA, Nature Biotechnology 34:339-344 (2016); and Slaymaker et al., Rationally engineered Cas9 nucleases with improved specificity, Science, 351(6268):84-8.

In other embodiments, the genome editing biomolecule can comprise elements that facilitate the random integration of exogenous DNA into the genomes of cells (referred to herein as "non-targeted genome editing"). For example, the genome editing biomolecule can comprise a t nucleic acid molecule that includes repeat elements (e.g., inverted repeats) and, optionally, a transposase. The transposase can be encoded by the nucleic acid molecule, encoded by a separate nucleic acid molecule, or may be a protein, which may be complexed with the nucleic acid molecule.

In some embodiments, a genome editing biomolecule can be complexed or otherwise associated with one or more proteins, lipids, organic ions, inorganic ions, or any combination thereof. The complex/association can facilitate the entry of the genome editing biomolecule into a cell. For example, the proteins and/or lipids can be part of a viral capsid or a liposome. Alternatively, a protein comprised by the genome editing biomolecule can be fused to a cell-penetrating peptide. For example, the protein can be an endonuclease or transposase that is fused to a cell-penetrating peptide.

In addition to the foregoing, various genome editing biomolecules suitable for targeted and non-targeted genome editing are known in the art. See, for example, Nayerossadat et al., Viral and nonviral delivery systems for gene delivery, Adv. Biomed. Res. 1:27 (2012); and Zuris et al., Cationic lipid-mediated delivery of proteins enables efficient protein-based genome editing in vitro and in vivo, Nature Biotech 33:73-80 (2015).

The genome editing biomolecule can comprise a donor template nucleic acid, such as donor template DNA molecule. Alternatively, the genome editing biomolecule and the donor template can be distinct molecular or macromolecular entities. As used herein, a "donor template" or "targeting nucleic acid construct" is a nucleic acid molecule comprising a delivery sequence; a "delivery sequence" is a nucleic acid sequence which has been selected for introduction into the genome of a cell. For embodiments in which the genome editing biomolecule and the donor template are distinct entities, methods of editing the genome of a selected cell (or cells) can further comprise the step of contacting the one or more cells with the donor template. The donor template can be provided, for example, in combination with the genome editing biomolecule, such as in a mixture. Alternatively, the one or more cells can be contacted with the genome editing biomolecule and the donor template at different times (e.g., sequentially).

The delivery sequence of the donor template a nucleic acid sequence which comprises or encodes a functional biomolecule that complements a mutation or functional deficiency in the genome of the cell being modified ("selected cell" or "target cell"). For example, the delivery sequence can include at least a portion of a gene or associate regulatory sequence; the gene, portion thereof, or regulatory sequence can be a wild-type sequence or a functional variant thereof. The functional variant can be an allelic variant (e.g., a known or novel allelic variant), which may include one or more point mutations (e.g., alteration, insertion, or deletion of a single base) that do not substantially diminish the function of the variant relative to a wild-type sequence.

Alternatively, the delivery sequence of the donor template can be a nucleic acid sequence which is configured to generate a mutation or functional deficiency in the genome of the target cell. For example, the delivery sequence can include at least a portion of a gene or associate regulatory sequence that includes a non-wild type sequence having reduced function. The reduced-function, non-wild type sequence can include one or more deletions, one or more point mutations (e.g., alteration, insertion, or deletion of a single base), or any combination thereof; the reduction in function (assessed relative to a corresponding wild-type sequence) can be partial or complete.

As yet another alternative, the delivery sequence of the donor template can include a nucleic acid sequence that comprises or encodes a functional biomolecule that confers an atypical functional activity upon a modified cell. For example, the delivery sequence can: include a hyper-functional allele of a gene, or a portion thereof, capable of increasing the overall level of activity of the gene in the cell; include a regulatory sequence configured for introduction at an atypical site in the genome of the target cell (e.g., the regulatory sequence can be flanked by sequences from a target site in the genome of the target cell); encode a fusion protein (e.g., a T cell receptor fusion protein, such as a CAR-T protein or the like); include a sequence that is found in the genome of a species which is different than the species of the target cell (e.g., the delivery sequence can be from a first mammal, such as a human, and the cell being genetically modified can be from a second mammal, such as a mouse, rat, sheep, goat, cow, or the like); include a sequence that encodes a reporter molecule; and/or include a synthetic sequence that is foreign to the target cell. The reporter molecule can be a molecule which is detectable in cells which have been genetically modified. For example, the reporter molecule can be a fluorescent protein (e.g., GFP or the like) or an RNA sequence that mimics a fluorescent protein (e.g. a "spinach" RNA aptamer). Alternatively, the reporter molecule can be a cell surface marker (which may or may not have an additional activity beyond serving as a marker), a protein that provides resistance to a selective agent, such as an antibiotic, or an enzyme that produces a quantifiable signal, such as horseradish peroxidase.

The delivery sequence of the donor template can include a barcode sequence. The barcode sequence (or "tag sequence") can be a random sequence of nucleotides (e.g., 6, 7, 8, 9, 10, 11, 12, 13, 14, 15, or more nucleotides) that differs between different genome editing biomolecules (or donor templates). The barcode sequence, in some embodiments, can comprise a sequence not typically found in the genome of the target cell or at least not proximal to (e.g., within 1, 2, 3, 4, 5, 10, or more kb) the location of the target site in the genome of the target cell.

The donor template can further comprise one or more targeting nucleic acid sequences that flank the delivery sequence on one or both sides. As used herein, a "targeting nucleic acid sequence" is a sequence that is sufficiently homologous to a nucleic acid sequence that flanks a target site in the genome of a target cell so as to increase the likelihood and fidelity of homologous recombination between the donor template nucleic acid and the nucleic acid sequence of the target site.

In some embodiments, genomic editing of cells placed within an editing region of a microfluidic chip comprises subjecting the cells to one or more forces that increase cell permeability and/or cell porosity, thereby increasing transfection efficiency. Depending on the type of force used, the editing region of the microfluidic device may contain corresponding structures or elements that facilitate generation of the force and/or the formation of pores in the cell membranes of the cells.

In some embodiments, genomic editing of cells placed within an editing region of a microfluidic chip comprises electroporating the cells. Electroporation of T cells can be accomplished, for example, by applying a DEP force to the cells. The use of DEP force to electroporate cells has been described in the art, including, for example, in Valley et al., Parallel single-cell light-induced electroporation and dielectrophorectic manipulation, Lab on a Chip 9:1714-17102 (2009). Accordingly, the editing region of the microfluidic device can have a DEP configurations, which can be as disclosed elsewhere herein, including an OET configuration. The editing region of the microfluidic device can comprise a substrate that is different from the substrate in other regions of the microfluidic device. The substrate, in combination with a cover and/or microfluidic circuit material, can define the editing region.

The substrate of the editing region can include at least one electrode. The at least one electrode of the substrate can form a select portion of a substrate surface that faces inward toward the editing region. Alternatively, the at least one electrode of the substrate can form all, or substantially all, of the inward facing surface of the substrate within the editing region. Regardless, the at least one electrode can be a single discrete electrode. Alternatively, the at least one electrode can be a plurality of discrete electrodes. When a plurality of discrete electrodes is present, the electrodes can form an orderly array (such as an n×m array wherein n and m are each an integer having a value of 1 or greater, or any portion of such an n×m array). The electrodes of an orderly array can be individually addressable. One or more (e.g., each) of the at least one electrodes of the substrate can be made from a metal. The metal can be, for example, any metal used in semiconductor processing, including a non-oxidizing metal (e.g., Au, Pt, or the like), or an alloy thereof, and/or a stack of metal layers. Activation of the metal electrodes can be controlled via transistor switches, including phototransistor switches.

The substrate of the editing region can include at least one electrode and a photoconductive layer. The photoconductive layer of the substrate can form a select portion of a substrate surface that faces inward toward the editing region, or the photoconductive layer can form all (or substantially all) of the substrate surface that faces inward toward the editing region. The at least one electrode of the substrate can be electrically coupled to the photoconductive layer while remaining insulated from fluid present in the editing region. The photoconductive layer can comprise one or more phototransistors. Alternatively, the photoconductive layer can comprise, consist of, or consist essentially of a layer of hydrogenated amorphous silicon (a-Si:H).

Genomic editing of cells can include placing the cells in a buffer that is optimized for electroporation, such as a low-conductivity buffer. The low conductivity buffer can be present in the editing region, for example, and moving the cells into the editing region can constitute placing the cells in the buffer. The low-conductivity buffer can minimize damage to the cells caused by electroporation.

Genomic editing of cells placed within an editing region of a microfluidic chip can include constricting or deforming the cell membranes of the cells in order to increase cell permeability and/or porosity, thereby increasing transfection efficiency. To achieve such constriction or deformation, the editing region of the microfluidic device can include physical structures configured to constrict or deform target cells. For example, the editing region can have a microfluidic channel that includes one or more constrictions. As used herein, a "constriction" in a microfluidic channel is a portion of the channel having a width that is smaller than the average diameter of a target cell (which, in the case of T cells, can change depending on whether the T cells are activated or not). The entire channel may narrow to form the constriction, or the channel may include barriers (e.g., posts) that are separated by a distance smaller than the average diameter of the target cell. The constriction in the walls of the channel or the barriers can be formed, for example, through the patterning of microfluidic circuit material. Alternatively, hydrogel structures formed in situ can be used to create one or more constrictions within a microfluidic channel, either by effectively reducing the width of the channel or by providing barriers. The hydrogel structures can be generated in situ by directing structured light onto a photo-activatable polymer, as described elsewhere herein. For example, structured UV light directed through a light modulating subsystem can activate the polymerization of a photo-activatable polymer in specific locations within the editing region of the microfluidic device. As another example, a hydrogel structure may be "drawn" around a target cell located within the editing region, causing constriction of the target cell. In some embodiments, hydrogel structures within the editing region can also be used to: limit diffusion of media containing the genome editing biomolecule, thereby retaining the genome editing biomolecule in close proximity to the target cell to facilitate successful transfection; and/or to contain (or seal) target cells within the editing region of the microfluidic device.

In some embodiments, genomic editing of cells placed within an editing region of a microfluidic chip comprises impaling the cells on microstructures. This process is known in the art as "impalefection." In these embodiments, one or more inner surfaces 208 of the editing region of the microfluidic device may be patterned with microstructures, such as nanotubes. In some embodiments, the microstructures may be infused with media comprising the genome editing biomolecule, or the microstructures may be used to capture micro-objects such as beads comprising the genome editing biomolecule. In certain embodiments, DEP force may be used to push the cells onto the microstructures such that the microstructures impale the cells. In other embodiments, a flow of medium can be used to push the cells onto the microstructures such that the microstructures impale the cells. The flow of medium can be generated in any manner described herein or otherwise known in the art, including the pumping of medium through the microfluidic device and localized flow. The generation of localized flow within a microfluidic device has been described, for example, in U.S. Patent Application Publication No. 2016/0158757, the entire contents of which are incorporated herein by reference.

In some embodiments, genomic editing of cells placed within an editing region of a microfluidic chip comprises subjecting the cells to a high-intensity ultrasound frequency. The ultrasound frequency can be selected so as to induce pore formation (sonoporation), and can optionally be applied when the cells are in the presence of an agent that facilitates pore formation. Micro-bubbles that are subject to acoustic cavitation when exposed to ultrasound may be used as an agent that facilitates pore formation.

In some embodiments, genomic editing of cells placed within an editing region of a microfluidic chip comprises contacting the cells with magnetic nanoparticles that comprise the genome editing biomolecule (and, optionally, donor template). In such embodiments, the transfection area of the microfluidic device may include a magnet, which may be integrated into the support structure or into the substrate of the microfluidic device. Regardless, the magnet can be controllably applied so as to force contact between the cells and magnetic nanoparticles once the cells are properly positioned in the editing region.

Depending on the embodiment, the application of force to facilitate cell permeability and/or porosity, including pore formation, can be performed after, or at substantially the same time as, contacting the target cell(s) with the genome editing biomolecule (and, optionally, donor template). The genome editing biomolecule (and donor template, if necessary) may be introduced directly into the editing region by means of a flow of fluidic medium through the editing region, which may occur concurrent with the introduction of target cells into the editing region (e.g., the target cells and genome editing biomolecules can be part of a mixture that is flowed into the editing region). Alternatively, the genome editing biomolecule (and donor template, if necessary) may be introduced indirectly, such as by diffusion from a fluidic medium flowing past an opening to the editing region. In still other alternatives, the genome editing biomolecule can be associated with a surface of a transfection structure, such as a wall or barrier within the editing region, a microstructure, or a nanoparticle. Microstructure and nanoparticle transfection structures can be localized to the editing region either prior to moving the target cells into the editing region, at the same time as moving the target cells into the editing region (e.g., if the structure is present in the same medium as the cells), or after the target cells are moved into the editing region (e.g., if the structure can be moved into the editing region by means of a selective force, such as DEP). The fluidic medium within the editing region of the microfluidic device can comprise different molecules or compounds which facilitate cell permeability and/or cell porosity and the transfection of the cells.

A variety of the above methods for introducing genome editing biomolecules into cells may be used, but certain methods can provide advantages for minimizing cellular toxicity and/or editing particular cell types. For example, electroporation of mRNA encoding an endonuclease, optionally in combination with guide RNAs (gRNAs), can facilitate ex vivo gene editing of primary cells. Alternatively, direct delivery of purified endonuclease protein or an endonuclease-nucleic acid complex (e.g., Cas9 protein-gRNA complex) can achieve high levels of gene editing, with such delivery affected by electroporation or by fusion to cell-penetrating peptides (which obviates electroporation-mediated toxicity). Viral vectors offer additional means of delivering genome editing biomolecules with high efficiency while minimizing cytotoxicity. For example, a lentiviral vector may be used for highly efficient transduction of hematopoietic stem cells; and an integrase-deficient lentiviral vector may be beneficially employed for transient introduction of genome editing biomolecules into a target cell. Adenoviral vectors can also achieve high levels of transduction ex vivo in a wide variety of cell types, while expressing functional components of the genome editing biomolecule (e.g., endonuclease) only transiently. Both lentiviral and adenoviral vectors provide cargo capacity sufficient to carry multiple nucleases and/or gRNA expression cassettes, and thus can allow for multiplex editing of several target sites within a genome.

Figure 5:
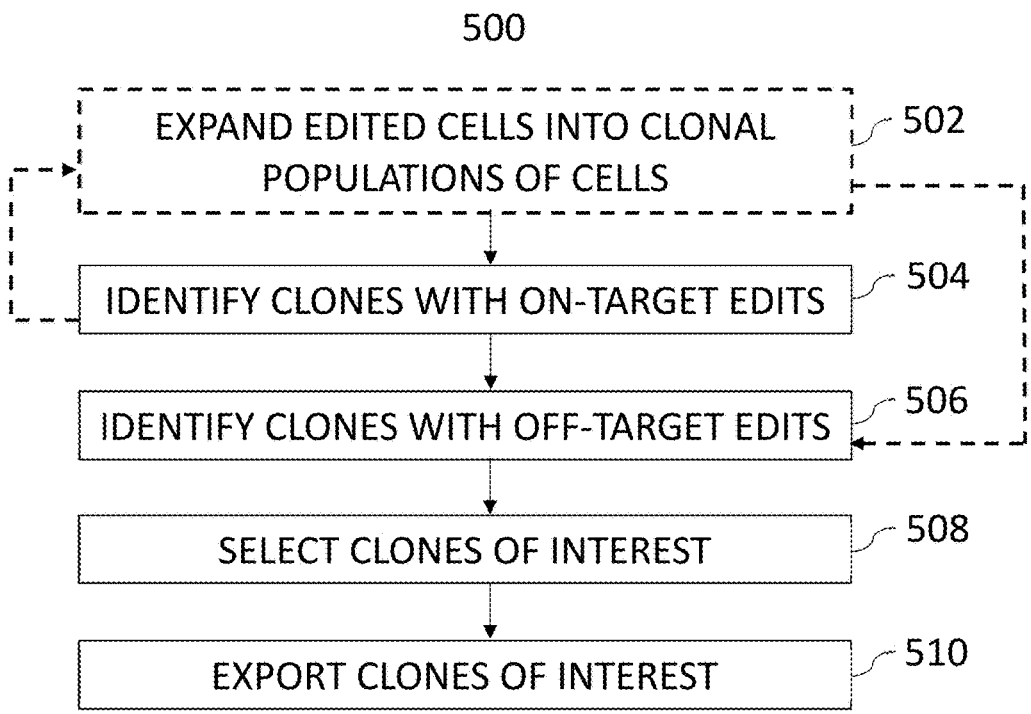
FIG. 5 illustrates steps in a method for identifying cells that have been successfully genome-edited according to some embodiments of the disclosure.

Once one or more target cells (e.g., a population of target cells) have been subjected to a genome editing process, it is typically necessary to ascertain whether any of the cells have been successfully edited. The identification of successfully edited cells can be facilitated using a microfluidic device as described herein, particularly microfluidic devices having sequestration pens configured for single cell isolation and expansion. FIG. 5 illustrates steps in an exemplary method 500 for selecting, analyzing, and identifying cells that have undergone a successful targeted (or non-targeted) genome editing event. At step 502 of method 500, cells that have been subjected to a genome editing process are optionally expanded into clonal populations. The expansion into clonal populations can include isolating single cells from the population of genome edited cells and expanding the single cells into distinct clonal populations. For example, individual cells can be isolated in corresponding sequestration pens in the microfluidic device and cultured under conditions conducive to the expansion of single cells into clonal colonies. The production of clonal cell populations derived from single cells facilitates genomic analysis, as discussed further below. Method 500 can be performed with genome edited cells that have been edited by any method known in the art or described herein, whether the editing process was performed within the microfluidic device or outside of the microfluidic device (i.e., prior to loading the population of genome edited cells into the microfluidic device).

In some embodiments, method 500 includes a step (not shown in FIG. 5) of performing an initial selection on the population of genome edited cells to enrich for cells that include a successful genome edit (e.g., a successful targeted edit). The first selection can be performed before, during, or after step 502.

The initial selection can be based upon a detectable marker that is not expressed (or is expressed at detectably lower levels) in pre-edited cells and/or cells that go through the editing process without being successfully edited. For example, the successful genome edit can introduced an exogenous nucleic acid sequence which encodes the detectable marker or a biomolecule, such as a protein, the generates the detectable marker. Alternatively, the successful genome edit can introduce an exogenous nucleic acid sequence which includes a non-coding, regulatory sequence that increases the expression of an endogenous nucleic acid sequence which encodes either the detectable marker or a biomolecule, such as a protein, that generates the detectable marker. The exogenous nucleic acid sequence can be part of a donor template, which may be part of a genome editing biomolecule, as discussed above. The detectable marker can be, for example, an epitope of a biomolecule, such as a protein or carbohydrate molecule that localizes to the cell surface. Alternatively, the marker can be a light-generating biomolecule, which may have an intracellular localization. Examples of light-generating biomolecules include, but are not limited to, green fluorescent protein (GFP) and derivatives thereof, bioluminescent proteins and derivatives thereof, enzymes the cleave a substrate that emits light upon cleavage, and the like. A "detectably lower level" can be 10%, 20%, 30%, 40%, 50%, 60%, 70%, 80%, 90% lower, or more relative to the level of the detectable marker in a cell that has undergone successful genome editing.

The initial selection of a subpopulation of genome edited cells can be performed prior to loading the genome edited cells into the microfluidic device. For example, genome edited cells that express a particular cell-surface epitope can be selected from a population of cells that have undergone gene editing by means of fluorescent activated cell sorting (FACS), magnetic bead-based binding, or any other sorting technology known in the art. The subpopulation of cells obtained from such selection (i.e., "off-chip" selection) can then be loaded into the microfluidic device for further processing, such as according to method 500 of FIG. 5 or the like. Alternatively, the detectable marker-based selection of a subpopulation of genome edited cells can be performed after loading the population of genome edited cells into the microfluidic device. For example, imaging can be used to detect cells that express a particular cell surface epitope, which may be labeled with an antibody or other specific binding agent having a fluorescent label. As another example, imaging can be used to detect cells that express a light-generating biomolecule. Regardless of the exact nature of the detectable marker (whether protein, carbohydrate, or light generating), cells identified as having the detectable marker can be selected and moved into corresponding sequestration pens. Thus, for example, the detection and selection of cells can be performed while the cells of the genome edited population are located within a flow region (e.g., a microfluidic channel) in the microfluidic device.

The amount of detectable marker (or "reporter molecule") can be quantified, and cells having a minimum threshold amount of the detectable marker can be selected for further processing (e.g., according to method 500). In some embodiments, it may be beneficial to expand one or more individual cells into clonal populations of cells, to determine whether the cells of the clonal population(s) exhibit an increased level of the detectable marker that is stable over time and/or after one or more cell divisions. For example, as discussed below, it may be beneficial to determine whether a single cell that produces GFP as a reporter molecule stably produces GFP as the single cell is expanded into a clonal population of cells. Similarly, in instances in which a genome edit results in a functional capability, as could be provided by a new signaling receptor or enzyme, it may be desirable to expand individual cells into corresponding populations of cells before assaying the functional capability.

In addition, for embodiments in which the cells are subjected to force during transfection with a genome editing biomolecule (and/or donor template), it may be useful to expand the transfected cells into clonal populations in order to determine whether transfection had any impact on cell viability. Similarly, in some embodiments, it may be beneficial to monitor cell expansion to determine whether the cells are proliferating at an expected rate. For example, because off-target genome editing could activate oncogenes or otherwise disrupt cell-cycle regulation, aberrant cell proliferation may be indicative of off-target genome editing.

As discussed above, genome-edited cells can contain targeted genome edits, which may be on-target or off-target, or non-targeted (i.e., random) genome edits. As used herein, an "on-target genome edit" (or "on-target genomic modification") refers to the successful integration of a nucleic acid sequence from a donor template into a target site in the genome of the cell and/or a deletion of endogenous DNA from the target site; an "off-target genome edit" (or "off-target genomic modification") refers to the integration of a nucleic acid sequence from a genome editing biomolecule or donor template at a site in the genome of the cell other than the target site, and/or the deletion of endogenous DNA at a site in the genome of the cell other than the target site. Whether on-target, off-target, or non-targeted, cells containing genome edits can be identified by characterization of their genomic sequence, or portions thereof. Thus, for example, at step 504 of method 500, cells that have been successfully modified to have on-target or non-targeted genome edits can be identified through characterization of their genomic sequence. Such characterization can include cell lysis, nucleic acid extraction, and further processing steps (e.g., fragmentation, tagging, and/or amplification). For example, amplification of extracted (and optionally fragmented and/or tagged) nucleic acid using primers specific to the first nucleic acid sequence and/or second nucleic acid sequence can allow detection of on-target genome edits. Alternatively, or in addition, the characterization genomic sequencing (e.g., DNA sequencing of select genomic regions, whole genome sequencing, RNA sequencing of select mRNA transcripts, whole transcriptome sequencing, and the like). Analysis of the results of such sequencing can be used to identify the first nucleic acid sequence and/or second nucleic acid sequence, and thereby allow detection of on-target genome edits.

In order to use techniques that require nucleic acid extraction, it is typically necessary to expand a single genome edited cell into a clonal population of cells, so that a subset of cells of the clonal population may be processed for genomic analysis while another subset of cells of the clonal population may be preserved for subsequent use (which can include export from the microfluidic device and growth off chip). Accordingly, in some embodiments, the characterization of the genomic sequence of a clonal population of genome edited cells comprises selecting one or more cells from the clonal population and performing genomic characterization on the one or more cells. Step 504 can be performed partially or completely outside of the microfluidic device (i.e., "off chip"). For example, characterizing the genome of genome-edited cells can include exporting one or more cells from a clonal population of cells and, following such export, performing cell lysis, nucleic acid extraction, and further processing and/or nucleic acid sequencing off chip. Alternatively, characterizing the genome of genome-edited cells can include moving one or more cells of a clonal population from within a sequestration pen to another chamber in the microfluidic device, performing cell lysis and nucleic acid extraction in the other chamber, and then exporting the extracted nucleic acid for further processing and/or sequencing off chip.

Depending on the embodiment, any method of identifying successful on-target (or non-targeted) genome edits may be combined with any other method, in any order. For example, in some embodiments, cells containing on-target (or non-targeted) genome edits may be identified by initially selecting individual cells based on the presence of one or more detectable markers (or reporter molecules), isolating and expanding each individual marker-positive cell into a clonal population, and then extracting DNA (and/or RNA) from one or more cells of the clonal population for further processing and/or genomic sequencing to confirm a successful on-target (or non-targeted) genome edit. In other embodiments, cells containing on-target (or non-targeted) genome edits may be identified by first isolating and expanding individual cells into clonal populations, then determining the presence of a marker (or reporter molecule) in each clonal population, and then extracting DNA (and/or RNA) from one or more cells of select (or all) clonal populations for further processing and/or sequencing to confirm a successful on-target (or non-targeted) genome edit. In other embodiments, cells that have on-target (or non-targeted) genome edits can be identified by first detecting a functional property of the on-target (or non-target) genome edit (e.g. a functional activity of a protein produced or deleted by the genome edit) in a single cell, isolating and expanding the single cell into a clonal population, and then extracting DNA (and/or RNA) from one or more cells of the clonal population for further processing and/or sequencing to confirm a successful on-target (or non-targeted) genome edit. In still other embodiments, cells that have on-target (or non-targeted) genome edits can be identified by first isolating and expanding single cells into clonal populations, then detecting a functional property of the on-target (or non-target) genome edit (e.g. a functional activity of a protein produced or deleted by the genome edit) in each clonal population, and then extracting DNA (and/or RNA) from one or more cells of select (or all) clonal populations for further processing and/or sequencing to confirm a successful on-target (or non-targeted) genome edit.

At step 506 of 500, cell populations identified as having successfully undergone genome editing can be analyzed to identify populations that harbor off-target genome edits. As with on-target genome edits, the presence of off-target genome edits (or defective non-targeted edits) may be assessed using a detectable marker (or reporter molecule) and/or by analyzing nucleic acid extracted from one or more cells of select (or all) clonal populations. The reporter molecule may, for example, be part of or encoded by a donor template (and, optionally, a genome editing biomolecule, as discussed above) which is configured such that the part that is or encodes the detectable marker/reporter molecule is lost upon successful editing but can be retained when the edit is off-target (or defective). Similar to step 504 of method 500, all or part of step 506 can be performed off chip. Moreover, all or part of step 506 may be performed in parallel with all or part of step 504. For example, nucleic acid may be extracted from one or more cells of a clonal population and "deep sequenced" to identify both on-target genome edits and off-target genome edits. Similarly, in embodiments where a detectable marker is used to identify off-target/defective genome edits, the step of detecting the off-target/defective marker can be performed before, during, or after cloning of individual cells to form cell populations, and before, during, or after the detection of markers associated with on-target/successful genome edits. In this latter regard, the Traffic Light Reporter system can be used, allowing for on-target genome edits and off-target genome edits to be identified simultaneously based on the production of different reporter molecules.

As will be evident to skilled persons, step 502 of method 500 may be repeated after step 504 and/or step 506, for the purpose of further expanding cells having successful on-target (or non-target) genomic edits. Such further expansion of single cells into sub-clonal populations, followed by the repetition of step 504 (and, optionally, step 506), can be performed to determine whether the on-target (or non-targeted) genome edits are stable over time. Any of steps 502, 504 and 506 may be repeated multiple times, in any order, or simultaneously; and the presence of a detectable marker (or reporter molecule) may be continually assessed while a single cell is expanded into a clonal population. Moreover, in any of the foregoing methods, a barcode sequence can be, upon insertion into the genome of a cell, used to identify daughter cells that are clonally derived from a successfully edited parent cell. The barcode sequence may be used, for example, in conjunction with a step comprising nucleic acid amplification (e.g., PCR) and/or nucleic acid sequencing to identify on-target and/or off-target genome edits.

At step 508 of method 500, clonal cell populations identified as comprising successful on-target (or non-targeted) genome edits are selected for export. At step 510 of method 500, one or more cells of the selected clonal populations are exported from the microfluidic device (e.g., for further culture, expansion, and/or processing).

The microfluidic device used in methods of ascertaining the success of genomic editing can be any of the microfluidic devices disclosed herein. In certain embodiments, the microfluidic device can have a substrate having a DEP configuration, which can include, consist of, or consist essentially of an OET configuration. In some embodiments, the microfluidic device can have a substrate having a EW configuration, which can include, consist of, or consist essentially of an OEW configuration. In some embodiments, the microfluidic device can have a substrate having a first section having a DEP configuration (which can include, consist of, or consist essentially of an OET configuration), and a second section having an EW configuration (which can include, consist of, or consist essentially of an OEW configuration). In accordance with the configuration of the microfluidic device, steps that require the selection and/or movement of individual cells (or groups of cells), whether for placement in sequestration pens, export, or the like, may be performed using DEP force, OET force, EW force, OEW force, fluid flow, localized flow, bubble-driven flow, or any combination thereof. Similarly, steps that require movement of media, whether for the purpose of providing nutrients and/or reagents to cells or for transporting cells or other microobjects, can be performed using EW force, OEW force, fluid flow, localized flow, bubble-driven flow, or any combination thereof. As a particular example, genome edited cells may be selected and moved into and out of a sequestration pen using DEP (and/or OET) force in a DEP (and/or OET)-configured portion of a microfluidic device, carried by fluid flow into an EW (and/or OEW)-configured portion of the microfluidic device, and then subjected to cell lysis and nucleic acid extraction and processing using EW (and/or OEW) force to manipulate droplets containing the cells, nucleic acids, and/or reagents.

Cells useful in the disclosed methods. Cells that may be expanded within a microfluidic device and, optionally, genetically modified therein, include, but are not limited to eukaryotic cells, including cells obtained or derived from a worm, insect, fish, reptile, amphibians, bird, mammal, or the like. Worm cells can be from any type of worm, including, for example, a free-living worm, such as in the *Caenorhabditis* genus (e.g., *C. elegans*), or a parasitic worm. Insect cells can be from any type insect, including a fruit fly, such as in the *Drosophila* genus (e.g., *D. melanogaster*), and a mosquito, such as in the genus *Anopheles* (e.g., *A. gambiae*) or the genus *Aedes* (e.g., *A. aegypti, A. albopictus, A. polynesiensis*). Fish cells can be from any type of fish, including fish that are studied, such as a fish of the genus *Danio* (e.g., *D. rerio*), or consumed, such as trout (e.g., *Oncorhynchus mykiss*, etc.), carp (e.g., *Ctenopharyngodon idella, Hypophthalmichthys molitrix, Cyprinus carpio*, etc.), salmon (e.g., *Salmo salar*, etc.), catfish (e.g., *Silurus asotus*, etc.), and the like. Reptile cells can be from any type of reptile, including lizards (e.g., geckos, chameleons, iguanas, etc.), crocodilians (e.g., alligators, crocodiles, etc.), snakes (e.g., rattlesnakes, cobras, constrictors, pythons, coral snakes, mambas, vipers, garden snakes, etc.), or cryptodira (e.g., fresh water turtles, sea turtles, tortoise, etc.). Amphibian cells can be from any type of amphibian, including frogs (e.g., *Xenopus laevis, Lithobates catesbeiamus, Rana catesbeiana*, etc.), or toads (e.g., *Bufonidae* family, etc.). Bird cells can be from any type of bird, including chickens (e.g., *Gallus gallus*), turkeys, pheasants, and the like. Mammalian cells can be from any type of mammal, domesticated or wild, including rodents, such as rats (e.g. *Rattus* genus), mice (e.g., *Mus* genus), guinea pig (e.g., *Cavia* genus), and the like, rabbits (e.g., *Oryctolagus, Sylvilagus*, or *Pentalagus*; genus), sheep (e.g., *Ovis* genus), goat (e.g., *Capra* genus), pig (e.g., *Sus* genus), cattle (e.g., *Bos* or *Bison* genus), horse (e.g., *Equus* genus), primates, including haplorrhine primates (e.g., monkeys) and strepsirrhines primates (e.g., lemurs, etc.), and apes, such as orangutans (e.g., genus *Pongo*), gorillas (e.g., genus *Gorilla*), chimpanzees (e.g., genus *Pan*), and humans (e.g., genus *Homo*).

Cells from multicellular organisms can be any of a variety of different cells types, including cells of the immune system and stem/progenitor cells. Cells of the immune system, particularly from the immune system of a mammal, can include: T lymphocytes; cells that express at least one protein selected from the group of CD3, CD4, CD8, T-bet, GATA-3, CD25, Foxp3, ROR-gammaT, CD38, and CD40; B lymphocytes; NK cells; cells that express at least one protein selected from CD56 and CD16; macrophages; and cells that express at least one protein chosen from F4/80, Siglec-3, gamma receptor, CD19, CD20, and CD21. Stem/progenitor cells can include totipotent cells, pluripotent cells, multipotent cells, and oligopotent cells. Depending on the specific genome editing desired and the particular use for the product genome edited cell, the selection of the cell type (and its level of differentiability) may be made.

Thus, in some embodiments, stem cells having totipotent, pluripotent or multipotent behavior may be selected. A totipotent stem cell is comparable to an early stage zygote, which may differentiate into any of the cell types required for embryonic development and implantation. For a human zygote, totipotency is generally lost at about the fifth day post-fertilization.

A pluripotent stem cell has the potential to differentiate into any of the three germ layers: endoderm (e.g., cells of the interior stomach lining, gastrointestinal tract, lungs, etc.), mesoderm (e.g., muscle, bone, blood, urogenital cells, and the like), or ectoderm (e.g., epidermal cells, cells of the nervous system, including neurons, etc.). This class includes embryonic stem cells (ESCs). This class also includes ES produced by somatic cell nuclear transfer (ntESC). These cells may be produced by withdrawal of the nucleus of a donor egg, with subsequent insertion of the nucleus of an adult cell (which may include but is not limited to a skin cell). Gene reprogramming and reactivation may be triggered by the process of transferal. The resulting cell is grown to blastocyst status and its inner cell mass is isolated to create ntESCs. These cells may be useful for therapeutic cloning, not reproductive cloning. Another related type of pluripotent cell is a parthenogenetic stem cell (pESC). Parthenotes may be used to create sources of pluripotent cells matched to a patient's immune system, or may be used as a source of stem cells for the donor or a sibling thereof. Methods of producing pESCs in a microfluidic device are described in U.S. Patent Application Publication No. 2016/0257918, titled "Generation and Selection of Embryos In-Vitro," and its contents are hereby incorporated by reference in their entirety.

Pluripotent stem cells also include induced pluripotent stem cells (iPSCs). Induced pluripotent stem cells (iPSCs) can be sourced from the patient's own somatic cells, often a dermal fibroblast. Pluripotency may be induced by introducing a selected set of genes which reprogram the specific somatic cell type back to an earlier undifferentiated state. Typical genes introduced include Sox2, Oct4 (also known as Pou5fl), cMyc, and Klf4. Alternatively, transcription factors related to these genes, miRNAs, and selected small molecules may be used to effect the reprogramming. LIN28, a mRNA binding protein, and/or Glis1 (a transcription factor) may be used, particularly to replace c-myc, reducing concerns about oncogenicity. Some examples of such small molecules that can facilitate the formation of iPSCs include a histone deactylase (HDAC) inhibitor and valproic acid. Cocktails of small molecules including 3-deazaoneplanocin A (DZNep) can also be used to chemically reprogram adult cells. Further, a combination of an ALK5 inhibitor SB431412 and a mitogen activated protein kinase inhibitor PD0325901 can be used, optionally including Thiazovivin. In some embodiments, a renal epithelial cell may be induced into pluripotency by only two factors, SOX2 and Oct4, providing iPSCs.

Pluripotent iPSCs can be selected from a mixed population of cells by identifying Fbx15, an ESC-specific gene, or Nanog. Using Nanog for selection of iPSCs can provide iPSCs having a stem cell status more similar to that of ESCs, compared to iPSCs selected using Fbx15. The NANOG protein is a transcriptional activator for the Rex1 promoter, to sustain expression, where Rex1 is also a marker for pluripotency activity. NANOG prevents differentiation through a network of various transcription factors and protein kinases. Other markers for pluripotency may include TRA-1-60 (a sialylated keratan sulfate proteoglycan which is a human stem cell-defining antigen), TRA-1-81 (also a human stem cell-defining antigen), SSEA4 (stage specific early embryonic glycolipid antigen), alkaline phosphatase, FGF4 (fibroblast growth factor 4), ESG1, DPPA2 (Developmental pluripotency gene2), DPPA4 (Developmental pluripotency gene 4), and TERT (telomerase reverse transcriptase).

However, some pluripotent stem cells, particularly iPSCs, can have limitations on the degree to which they can differentiate into one or more of the cells from the three types of germ layers (i.e., ectoderm, mesoderm, and endoderm), as well as some limit on self-renewal. In addition, some types of pluripotent stem cells can have a propensity to commit to differentiation which is altered from that of embryo-derived ESCs.

Other cell types often referred to as stem cells are multipotent, including cells such as hematopoietic cells. These cells typically may have the potential to differentiate into a variety of cells types, but not as wide a variety as pluripotent cells may have. A variety of cell types have been identified as having subsets of these populations which may be stem cells, including but not limited to adipose cells, myofibroblast cells, dermal fibroblast cells, bone marrow (hematopoietic), human umbilical cord tissue or blood cells, neural cells, blood cells, renal epithelial cells, and mesenchymal cells. Various of these cells may alternatively be referred to as progenitor cells as they are partially committed to differentiation to varying degrees depending on the specific type of progenitor/stem cell. One example is an osteochondro progenitor cell, which is differentiated from a mesenchymal cell (a multipotent stem cell), and can itself differentiate into chondrocytes or osteoblasts, but not all the classes of cells into which a mesenchymal cell may differentiate.

As another example, hematopoietic cells may give rise to varied blood cell types but may not differentiate into non-blood cell types. In another example, human umbilical cord tissue (HUCT) may yield mesenchymal stem cells, which may be advantageously used, demonstrating less "mature" behaviors than other multipotent stem cells or iPSCs, and may trigger less graft v host disease (rejection). A mesenchymal stem cell may differentiate into various connective tissues, potentially differentiating into muscle cells, osteoblasts, chondrocytes, and adipocytes. Another source of mesenchymal stem cells is found within the third molar of humans. Periodontal or gingival tissue may also provide stem cells of the mesenchymal group for tendon engineering.

In other embodiments, human umbilical cord blood stem cells may differentiate into neuronal cells. Renal epithelial stem cells are non-invasively collected from urine, and may be useful for renal repair.

Adipose stem cells are proposed to be readily available from cosmetic surgery procedures and can be identified using stem cell—associated gene markers, including Oct4, Rex1, Sox2, as well as CD34. Other markers that may be used to identify and isolate these differentiable cells may include high expression in subcutaneous derived ASC of CD10, and for vascular derived ASC, low expression of CD200. ASC provide mesenchymal stem cells.

Uses of genome-modified cells. Single gene disorders may be addressed using gene editing to ameliorate pathophysiology associated with the gene defect. The gene disorders may be selected from autosomal dominant, autosomal recessive, X-linked or Y-linked disorders.

Some exemplary autosomal dominant gene disorders may benefit from delivery of gene edited stem/progenitor cells, .including but not limited to Huntington's disease (huntingtin gene at 4p16.3); Marfan syndrome (a defect in fibrillin, associated with connective tissue disorders (FBN1 gene at 15q21.1)); familial hypercholestemia (one of the most common forms is a defect in the LDL receptor (LDLR gene at 19p13.1-13) or a defect in Apolipoprotein B (APOB gene at 2p24.1)); polycystic kidney disease (defects in polycystin (most common are defects in polycystin 1 (PKD1 gene at 16p13.3) or polycystin 2 (PKD2 gene at 4q22.1)); neurofibromatosis (NF-1 gene at 17q11.2); and retinoblastoma (RB1 gene at 13q14).

Some exemplary autosomal recessive gene disorders that may be treated by administration of gene edited stem/progenitor cells may include but are not limited to ADA-SCID (an adenine deaminase deficiency resulting in severe combined immunodeficiency (ADA gene at 20q13.12)), cystic fibrosis (a chloride ion channel defect (CFTR gene at 7q31.2)); sickle cell anemia (affecting beta globin gene, leading to vascular occlusive crises with permanent organ damage (HbS gene at 11p15.5)); Tay Sachs (hexosaminidase A deficiency (HEXA gene at 15q24.1)); alpha-1 antitrypsin deficiency (lung and liver damage due to excessive elastase activity (SERPINA1 gene at 14q32.1))and phenylketonuria (mutation in phenylalanine hydroxylase (PAH gene at 12q22-q24.2). For example, ADA SCID treatment may introduce gene edited hematopoietic cells into bone marrow to provide corrected amounts of adenosine deaminase to the immune system. Alternatively, iPSC may be edited and introduced for such purposes.

A number of disorders are present on the X chromosome and may benefit from treatment with genome-edited stem/progenitor cells. Examples include, but are not limited to hemophilia (clotting factor Factor VIII (F8 gene at Xq28); Duchenne muscular dystrophy (dystrophin gene at Xp21); and Rett syndrome (X-linked MECP2 gene at Xq28).

While single gene disorders may be more easily addressed with this method, it may also be possible to address multiloci diseases such as diabetes, asthma, or multiple sclerosis. When sufficiently large vectors such as lentiviral or AAV vectors contain multiple sets of targeted gene editing biomolecules, multiplex amendment of genomic information may be performed.

Storage Devices. Also provided are machine-readable storage devices for storing non-transitory machine-readable instructions for carrying out any of the methods disclosed herein. The machine-readable instructions can optionally provide for control of the imaging device used to obtain the images.

EXAMPLES

Example 1

Targeted Genome Editing with an ARF1/GFP Genome Editing Biomolecule

HeLa cells (1×10$^6$ cells) were transfected with 1 microgram of Cas9-encoding plasmid, a guide RNA targeting the endogenous ARF1 sequence:

ACTGGCTGTCCAATCAGCTCCGG (SEQ ID NO: 1); and a donor template DNA comprising a portion of ARF1 fused in-frame with an insertion encoding Green Fluorescence Protein (GFP):

(SEQ ID NO: 2)
CTGCACTCACTACGCCACAGGAACTGGTACATTCAGGCCACCTGCGCCAC

CAGCGGCGACGGGCTCTATGAAGGACTGGACTGGCTGTCCAATCAACTAC

GAAACCAGAAGGGATCGTCAGGTCGGGATCCAGGCTCAGGTTCTGGA

*GTGAGCAAGGGCGAGGAGCTGTTCACCGGGGTGGTGCCCATC*

*CTGGTCGAGCTGGACGGCGACGTAAACGGCCACAAG*

*TTCAGCGTGTCCGGCGAGGGCGAGGGCGATGCCACCT*

*ACGGCAAGCTGACCCTGAAGTTCATCTGCACCACCGGC*

*AAGCTGCCCGTGCCCTGGCCCACCCTCGTGACCACCCTGA*

*CCTACGGCGTGCAGTGCTTCAGCCGCTACCCCGACCA*

*CATGAAGCAGCACGACTTCTTCAAGTCCGCCATGCCCGAAG*

*GCTACGTCCAGGAGCGCACCATCTTCTTCAAGGACGAC*

*GGCAACTACAAGACCCGCGCCGAGGTGAAGTTCGAGGGCG*

*ACACCCTGGTGAACCGCATCGAGCTGAAGGGCATCGACTT*

*CAAGGAGGACGGCAACATCCTGGGGCACAAGCTG*

-continued

```
GAGTACAACTACAACAGCCACAACGTCTATATCATGGCCG

ACAAGCAGAAGAACGGCATCAAGGTGAACTTCAAGATCCG

CCACAACATCGAGGACGGCAGCGTGCAGCTCGCCG

ACCACTACCAGCAGAACACCCCCATCGGCGACGGCCCCGTGC

TGCTGCCCGACAACCACTACCTGAGCACCCAGTCCGC

CCTGAGCAAAGACCCCAACGAGAAGCGCGATCACA

TGGTCCTGCTGGAGTTCGTGACCGCCGCCGGGATCACTCTCG

GCATGGACGAGCTGTACAAG

TAGGCGGCCGCGACT.
```

The bold and italics portion encodes GFP. The GFP served as a knock-in reporter molecule. The transfection was performed with lipofectamin as the transfection agent.

Following transfection, the population of genome-edited cells were imported into an OptoSelect™ chip having an SSRL10 coating (Berkeley Lights, Emeryville, Calif.). The chip included microfluidic channels and an OET-configured substrate, with a plurality of NanoPen™ chambers (i.e., sequestration pens) opening off of each microfluidic channel and the OET-configured substrate having a surface defining the base of the channels and sequestration pens. Single cells from the population of genome-edited cells were selected and moved into corresponding sequestration pens, then incubated on chip with regular perfusion of fresh culture medium through the microfluidic channels of the chip.

Figure 6A:
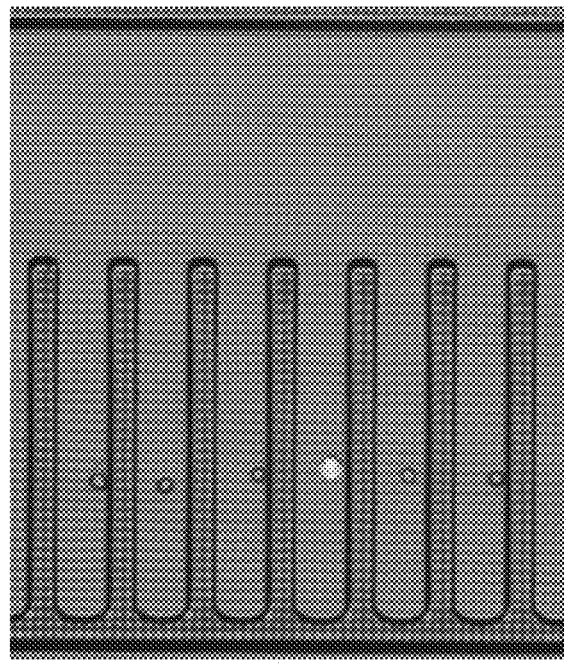
FIGS. 6A and 6B depict the selection of genome-edited cells according to a specific embodiment of the disclosure.
Figure 6B:
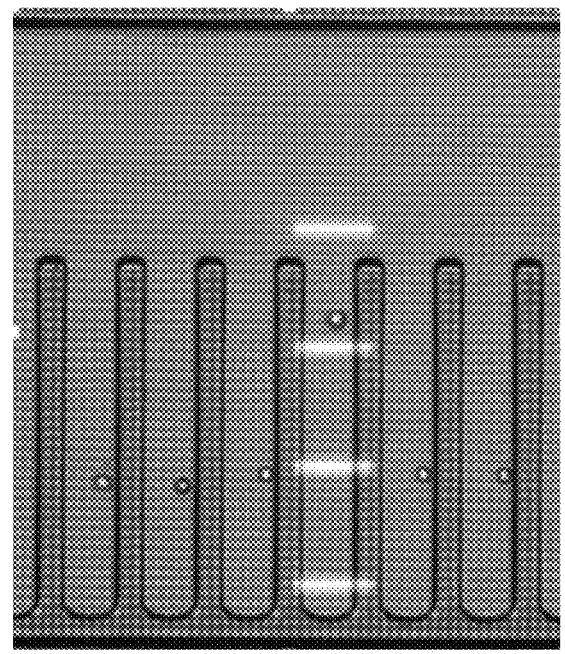

Cells containing on-target genome edits with ARF1-GFP were expected to harbor a golgi-localized fluorescent pattern, known to be in the perinuclear area of the cell. FIGS. 6A and 6B depict images of the transfected HeLa cells following importation into the chip, and selection and movement into sequestration pens. As shown in FIG. 6A, cells that were imported into the microfluidic chip were individually repositioned into a corresponding sequestration pen for expansion into clonal populations. In the image shown in FIG. 6A, the cell in the fourth pen from the left is emitting fluorescent light (appears white), indicating the presence of the GFP reporter molecule. The GFP indicates that the cell was successfully transfected with the genome editing biomolecule. FIG. 6B show patterns of light (shown as white light bars) used to activate the OET-configured substrate and thereby generate OET forces active upon the cell expressing GFP. Movement of the white light bars in the direction of the microfluidic channel results in the effective movement of the OET forces and export of the cell expressing GFP from the sequestration pen.

Figure 7A:
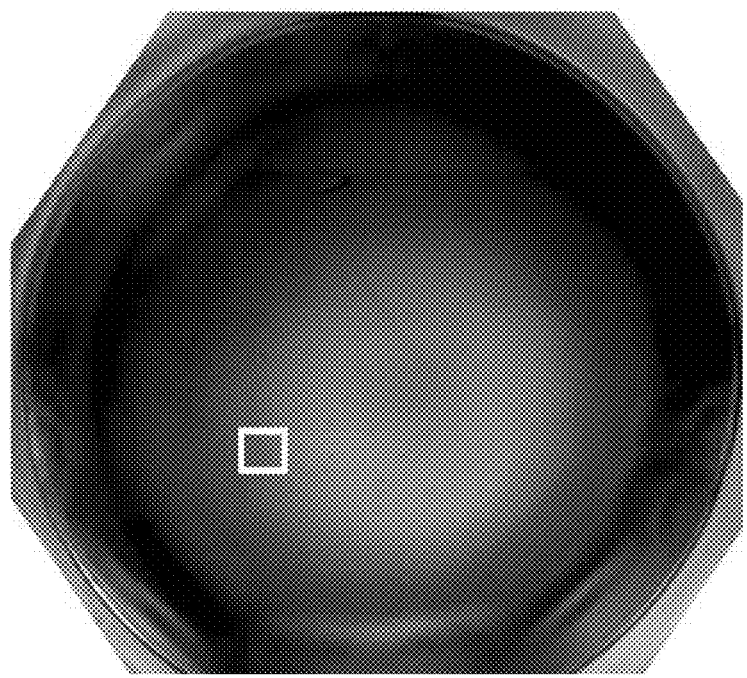
FIGS. 7A and 7B depict the expansion of genome-edited cells according to a specific embodiment of the disclosure.
Figure 7B:
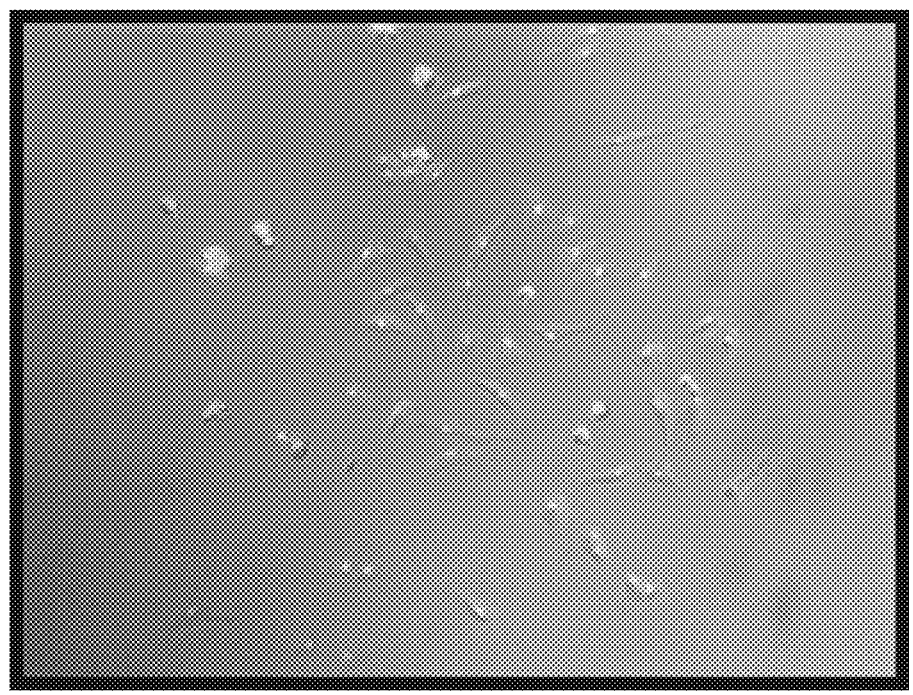

FIGS. 7A and 7B depict transfected HeLa cells deposited in the well of a 96-well plate following export from the microfluidic chip. FIG. 7A depicts the exported cells after two days of culture in the well plate. FIG. 7B depicts an enlarged view of the exported cells after six days of culture in the well plate. As depicted in FIG. 7B, the exported cells continue to produce GFP (shown in white), which is localized in the peri-nuclear area of the cells.

Figure 8:
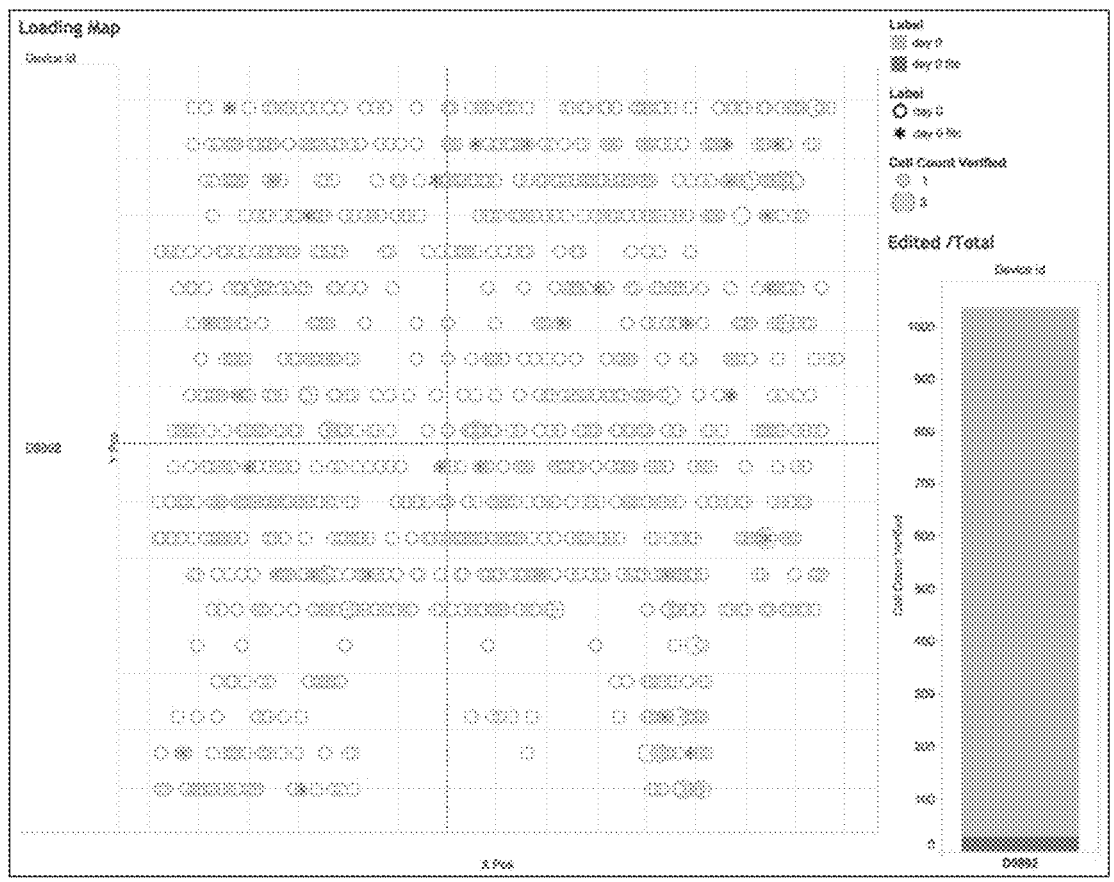
FIG. 8 depicts a plot showing the isolation of genome-edited cells in sequestration pens and the detection of a marker associated with genome editing according to a specific embodiment of the disclosure.

FIG. 8 depicts a plot of the microfluidic chip showing the relative location of sequestration pens in the chip, the number of cells in each pen, and whether a fluorescent signal arising from GFP was produced by the cells in each pen. Each row in the plot corresponds to a row of sequestration pens. Pens containing cells that produce GFP (quantified using a filter for fluorescein isocyanate, or "FITC") are indicated with asterisks and colored in gray; pens with multiple cells are indicated using large circles. As depicted in the plot, a number of cells throughout the microfluidic device produced GFP.

Figure 9:
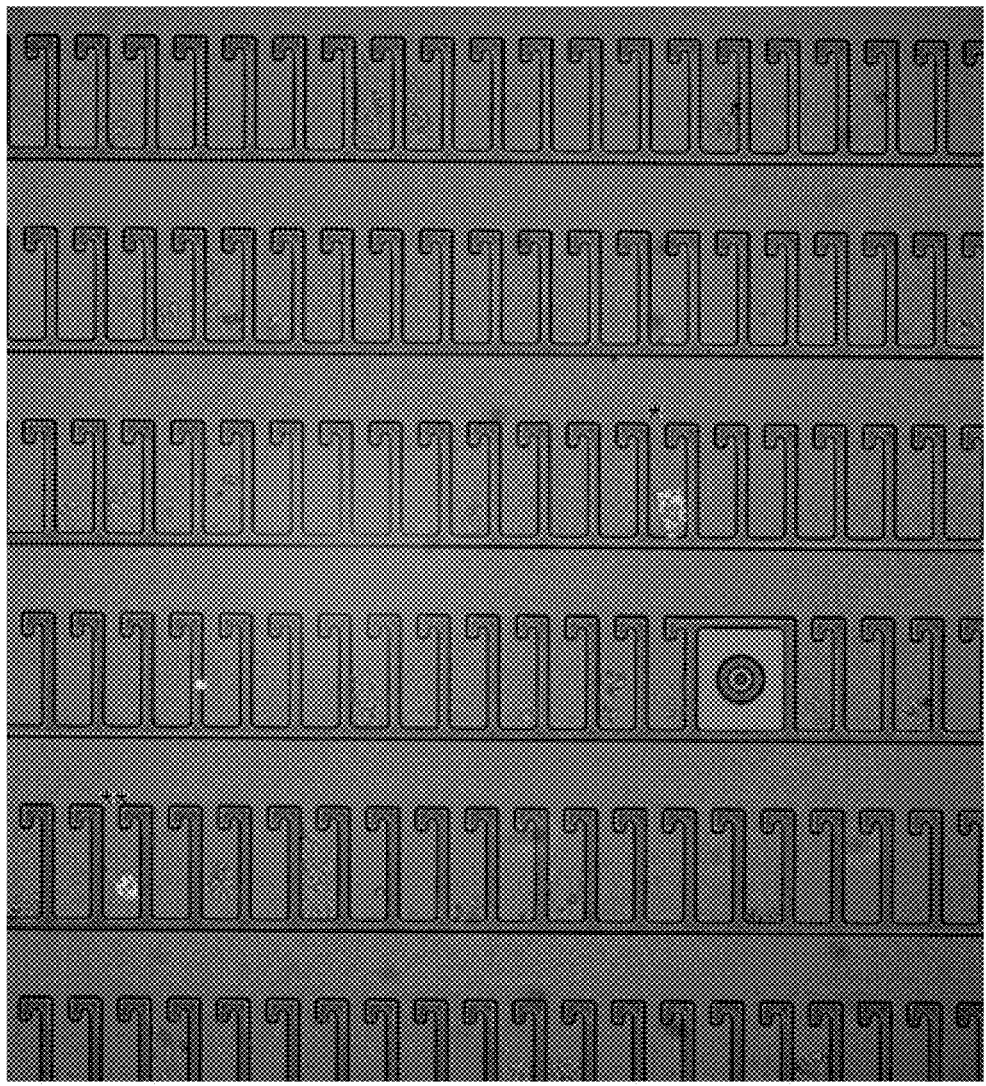
FIG. 9 depicts clonal populations of genome-edited cells according to a specific embodiment of the disclosure.
Figure 10:
FIG. 10 depicts clonal populations of genome-edited cells according to a specific embodiment of the disclosure.

FIGS. 9 and 10 depict images of the microfluidic chip at different time points. FIG. 9 shows a plurality of sequestration pens that were originally loaded with single cells which have expanded into clonal populations of cells following six days of culture on chip. Two of the sequestration pens (marked with single and double asterisks) comprise single cells producing GFP (shown in white) that have expanded into clonal populations; all of the cells in the clonal population of cells in the two sequestration pens produce green fluorescent protein, which is localized within the peri-nuclear (Golgi) area of the cells. FIG. 10 shows the same plurality of sequestration pens after nine days of culture on chip (i.e., three days later). As shown in FIG. 10, the two sequestration pens (marked with single and double asterisks) comprising cells producing GFP contain a larger number of cells than in FIG. 9 due to clonal expansion; again, all of the cells in the clonal populations express GFP.

Figure 11A:
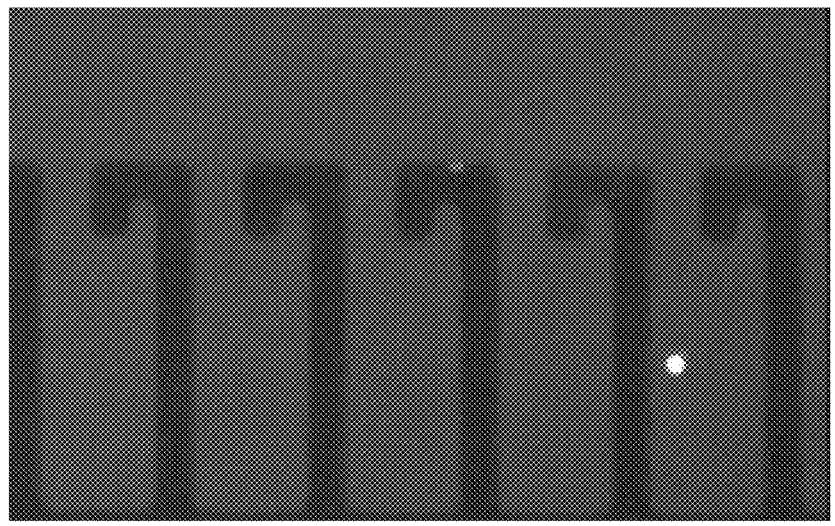
FIGS. 11A-11D depict the expansion of a single genome-edited cell into a clonal population of cells according to a specific embodiment of the disclosure.
Figure 11B:
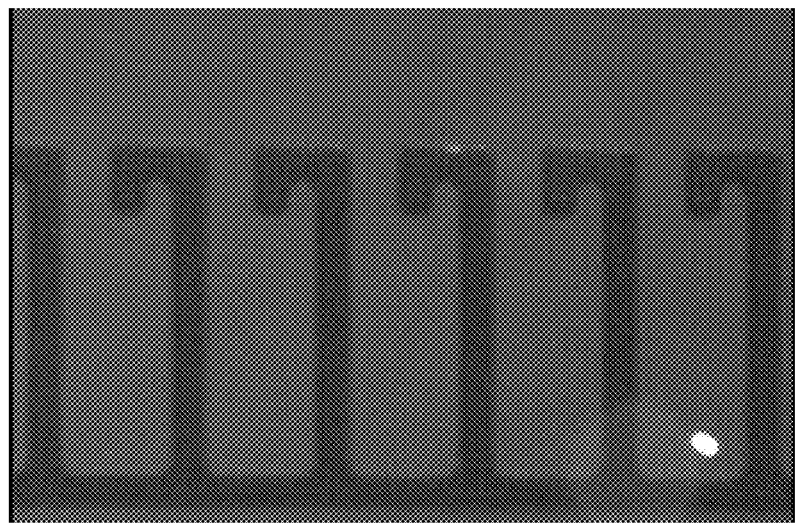
Figure 11C:
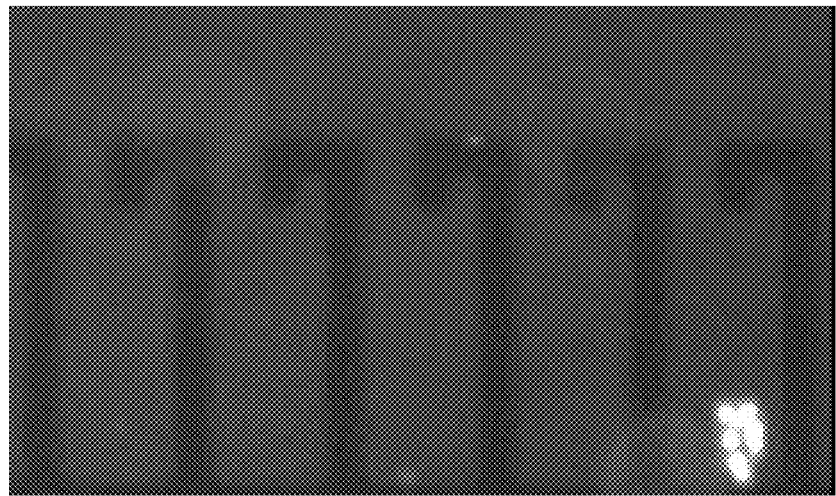
Figure 11D:
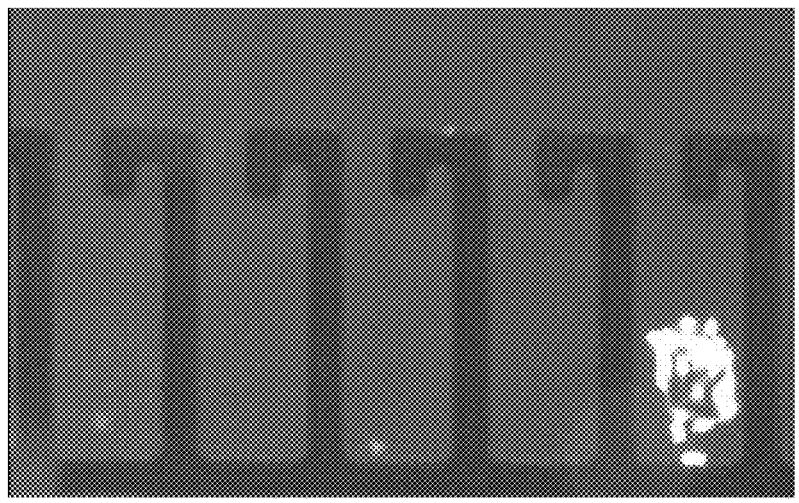

FIGS. 11A-11D provide an enlarged view of the sequestration pen marked with a single asterisk in FIGS. 9 and 10 at progressive time points. As shown in FIGS. 11A (zero hours of culture), 11B (one day of culture), 11C (three days of culture) and 11D (six days of culture), a single cell loaded into the sequestration pen on day zero stably produced GFP as it replicated into a clonal population of cells.

Figure 12:
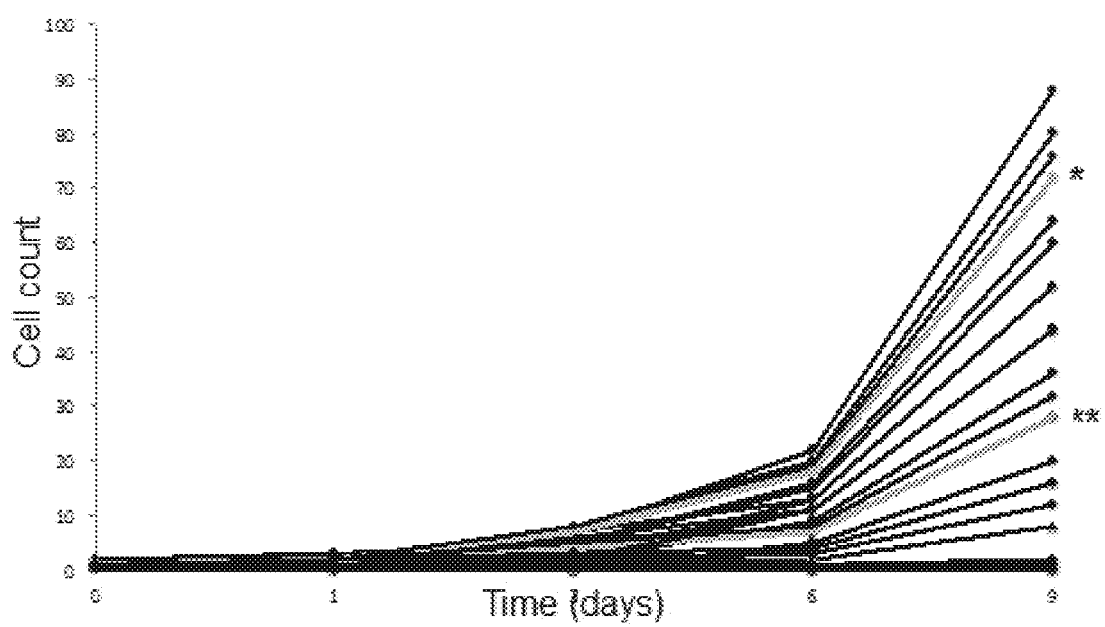
FIG. 12 depicts a graph of clonal expansion for a plurality of genome-edited cells over a nine-day period according to a specific embodiment of the disclosure.

FIG. 12 is a graph of the cell count from the sequestration pens depicted in FIGS. 9 and 10 over the nine-day culture period. Lines representing the two sequestration pens comprising cells that produce GFP are colored in gray and marked with single or double asterisks, as in FIGS. 9 and 10.

Following export, cells from selected clones were lysed and genomic DNA was extracted and amplified by means of PCR. The PCR-based amplification included a first PCR reaction, having a forward primer F1 and reverse primer R1, which was designed to amplify a region of ARF1 that lacks a GFP insert (FIG. 13, left panel, upper band).

```
F1:
                                          (SEQ ID NO: 3)
    ACCTCCCCAACGCCATGAATGCGG

R1:
                                          (SEQ ID NO: 4)
    TGCTAGGCGGGGTCTCCC
```

Figure 13:
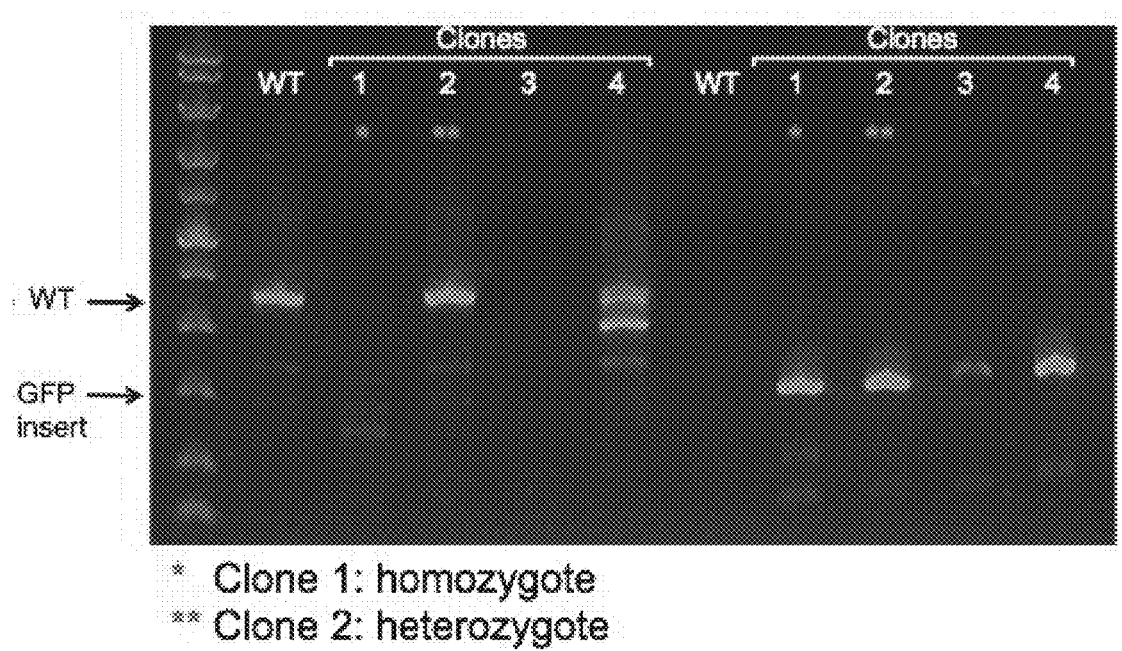
FIG. 13 depicts the use of nucleic acid amplification and analysis to identify on-target genome edits according to a specific embodiment of the disclosure.

The PCR-based amplification also included a second PCR reaction, having a forward primer F2 and reverse primer R2, which was designed to amplify the first 100 bps of an ARF1 allele having a GFP-encoding nucleic acid inserted therein (FIG. 13, right panel, lower band).

```
F2:
                                          (SEQ ID NO: 5)
    ACCTCCCCAACGCCATGAATGCGG

R2:
                                          (SEQ ID NO: 6)
    GTGGCATCGCCCTCGCCCTCG.
```

FIG. 13 is an image of an agarose gel following electrophoresis of amplified DNA from the select clones and staining with ethidium bromide. The lane labelled "WT" contains amplicons generated from DNA extracted from wild-type HeLa cells. Lanes labelled "Clone" 1, 2, 3, and 4 include amplicons generated from DNA extracted from the clones of selected cells from the ARF1/GFP Experiment. The lower band (indicated with an arrowhead and the label "GFP insert") corresponds to an amplicon comprising nucleic acid encoding GFP. The upper band (indicated with an arrowhead and the label "WT") corresponds to an amplicon of the endogenous ARF1 sequence; it is only present if the cells have at least one allele that lacks an on-target genome edit. As shown in FIG. 13, the lane for clone 2 has (i) a band indicating the presence of DNA encoding GFP at the ARF1 target site, and (ii) a band indicating the presence of DNA encoding WT ARF1. These bands indicate that clone 2 is heterozygous for the on-target genome edit—that is, only one of the chromosomes in clone 2 was subject to an on-target genome edit. In contrast, clone 1 has a single band indicating the presence of DNA encoding GFP at the ARF1 target site; clone 1 does not have a band indicating the presence of DNA encoding WT ARF1, indicating that clone 1 is homozygous for the on-target genome edit. As expected, the lane for the wild-type cells (WT) only has a band indicating the presence of DNA encoding WT ARF1.

Example 2

On-Chip Transfection of CHO Cells

A low conductivity buffer containing a mixture of Chinese Hamster Ovary ("CHO") cells and a plasmid vector comprising nucleic acid encoding GFP were imported into an OptoSelect™ chip (Berkeley Lights, Emeryville, Calif.). The chip included microfluidic channels and an OET-configured substrate, with a plurality of NanoPen™ chambers (i.e., sequestration pens) opening off of each microfluidic channel and the OET-configured substrate having a surface defining the base of the channels and sequestration pens. The OET-configured substrate included a layer of amorphous silicon. The CHO cells were electroporated (from 1.6V to 5V, for 8 to 80 ms) on chip using OET force, allowing the cells to take up the GFP plasmid.

Figure 14A:
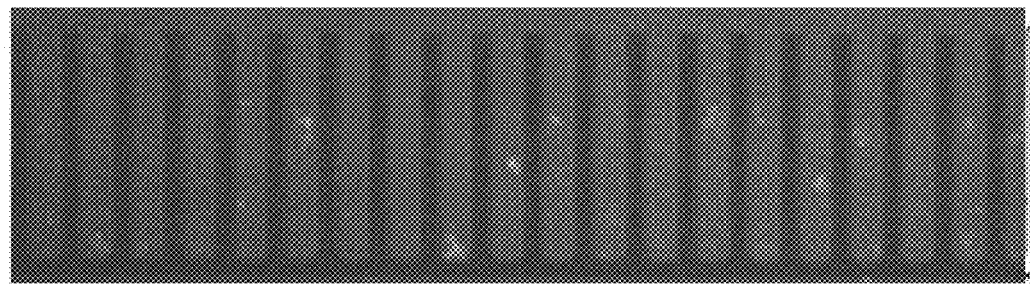
FIGS. 14A, 14B, 14C and 14D depict the use of electroporation to transfect cells in an area of a microfluidic device according to a specific embodiment of the disclosure.
Figure 14B:
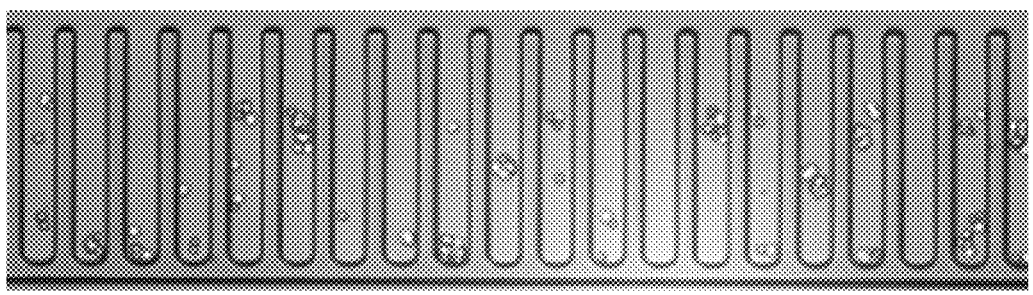
Figure 14C:
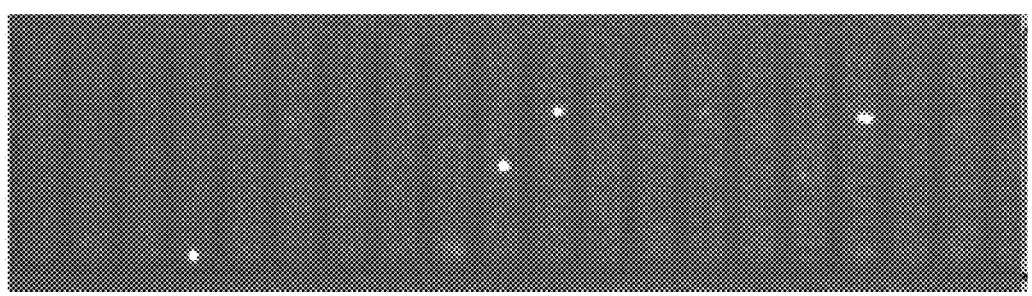
Figure 14D:
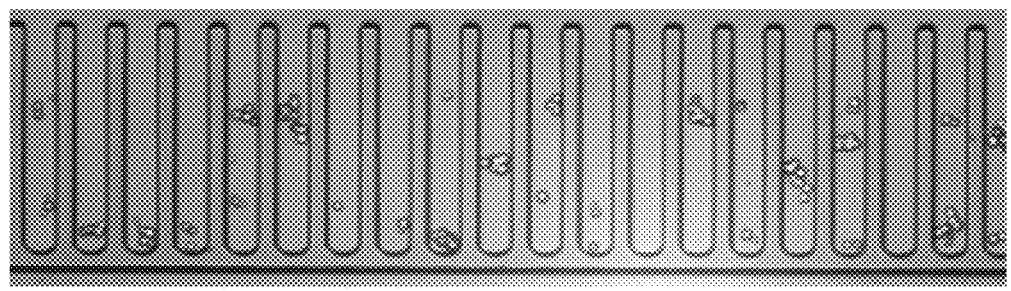

FIGS. 14B and 14D are brightfield images of the CHO cells on chip, minutes after electroporation (FIG. 14B) and one day after electroporation (FIG. 14D). FIGS. 14A and 14C, respectively, depict the GFP (shown in white) produced by the CHO cells minutes after electroporation and one day after electroporation. As shown in FIG. 14C, several cells successfully produce GFP one day after electroporation within the microfluidic device.

Example 3

Embodiments

The following numbered items provide further nonlimiting details on the embodiment described herein.

Item 1. A method of generating a clonal population of genetically modified cells in a microfluidic device comprising a sequestration pen, the method comprising: maintaining a first cell in the sequestration pen of the microfluidic device, wherein the first cell has undergone a genome editing process;
expanding the first cell into a clonal population of cells; and
detecting, in one or more cells of the clonal population, the presence of a first nucleic acid sequence, wherein the first nucleic acid sequence indicates the presence of an on-target genome edit in the clonal population of cells.

Item 2. The method of item 1, wherein the first cell is a mammalian cell.

Item 3. The method of item 2, wherein the first cell is a human cell, a rodent cell, a bovine cell, an ovine cell, a porcine cell, a canine cell, or a feline cell.

Item 4. The method of any one of items 1 to 3, wherein the first cell is an immunological cell.

Item 5. The method of item 4, wherein the immunological cell is chosen from a T cell, a B cell, an NK cell, a macrophage, or a precursor thereof.

Item 6. The method of any one of items 1 to 4, wherein the first cell is a stem cell.

Item 7. The method of item 6, wherein the stem cell is an embryonic stem cell, a mesenchymal stem cell, an umbilical vein mesenchymal stem cell, or an induced pluripotent stem cell (iPSC).

Item 8. The method of item 6, wherein the stem cell is a hematopoietic stem cell, an adipose-derived stem cell, a gingival stem cell, a renal stem cell, or a neural stem cell.

Item 9. The method of any one of items 1 to 4, wherein the first cell is a progenitor cell.

Item 10. The method of item 9, wherein the progenitor cell is an osteochondroprogenitor cell, a myofibroblast, a dermal fibroblast, or an endothelial progenitor cell.

Item 11. The method of any one of items 1 to 14, further comprising:
contacting the first cell with a genome editing biomolecule; and
introducing the first cell into the microfluidic device.

Item 12. The method of item 11, wherein the genome editing biomolecule comprises a donor template nucleic acid molecule.

Item 13. The method of item 11, further comprising:
contacting the first cell with a donor template nucleic acid molecule.

Item 14. The method of item 13, wherein the first cell is contacted with the genome editing biomolecule and the donor template nucleic acid molecule at substantially the same time.

Item 15. The method of any one of items 12 to 14, wherein the donor template nucleic acid molecule comprises all or part of the first nucleic acid sequence.

Item 16. The method of any one of items 11 to 15, wherein the step of transfecting the first cell is performed prior to the step of introducing the first cell into the microfluidic device.

Item 17. The method of any one of items 11 to 15, wherein the step of transfecting the first cell is performed after the step of introducing the first cell into the microfluidic device.

Item 18. The method of item 17, wherein transfecting the first cell is performed according to any one of items 46 to 84.

Item 19. The method of any one of items 11 to 18, further comprising selecting the first cell for transfection based on one or more characteristics selected from morphology, size, production of a protein of interest, the presence of one or more cell surface markers, and reaction with a specific antibody.

Item 20. The method of item 19, further comprising positioning the first cell in the sequestration pen, wherein said positioning is performed after selecting the first cell.

Item 21. The method of any one of items 1 to 20, wherein the microfluidic device comprises a substrate having a DEP configuration, and wherein the method further comprises positioning the first T cell in the sequestration pen using dielectrophoretic (DEP) force.

Item 22. The method of any one of items 1 to 21, wherein detecting the first nucleic acid sequence comprises:
selecting one or more cells from the clonal population of cells; and extracting nucleic acid from the one or more selected cells.

Item 23. The method of item 22, further comprising:
moving the one or more selected cells out of the first sequestration pen; and
exporting the one or more selected cells from the microfluidic device, wherein the nucleic acid is extracted outside of the microfluidic device.

Item 24. The method of item 22, further comprising: moving the one or more selected cells out of the first sequestration pen to a separate region within the microfluidic device, wherein the nucleic acid is extracted in the separate region.

Item 25. The method of any one of items 22 to 24, further comprising amplifying the extracted nucleic acid.

Item 26. The method of item 25, wherein amplifying the extracted nucleic acid comprises performing polymerase chain reaction (PCR) amplification.

Item 27. The method of item 25, wherein amplifying the extracted nucleic acid comprising performing whole genome amplification (WGA).

Item 28. The method of any one of items 25 to 27, wherein amplifying the extracted nucleic acid comprises amplifying the first nucleic acid sequence.

Item 29. The method of any one of items 22 to 28, wherein the extracted nucleic acid comprises genomic DNA.

Item 30. The method of any one of items 22 to 29, wherein the extracted nucleic acid comprises ribonucleic acid (RNA).

Item 31. The method of item 30, further comprising reverse transcribing the extracted RNA with a reverse transcriptase.

Item 32. The method of any one of items 1 to 31, wherein the on-target genome edit comprises a deletion of endogenous deoxyribonucleic acid (DNA) at a target site in the genome.

Item 33. The method of any one of items 1 to 32, wherein the on-target genome edit comprises an insertion of exogenous deoxyribonucleic acid (DNA) at a target site in the genome.

Item 34. The method of item 32, wherein the insertion encodes a functional biomolecule, a barcode, and/or a reporter molecule.

Item 35. The method of item 33 or 34, wherein detecting the presence of the first nucleic acid sequence comprises detecting all or part of the insertion.

Item 36. The method of any one of items 1 to 35, further comprising: detecting, in one of more cells of the clonal population, the presence of a second nucleic acid sequence, wherein the combination of the first nucleic acid sequence and the second nucleic acid sequence indicates the presence of the on-target genome edit in the clonal population of cells.

Item 37. The method of any one of items 1 to 36, further comprising: detecting, in one of more cells of the clonal population of cells, the presence of an additional nucleic acid sequence, wherein the additional nucleic acid sequence indicates the presence of an off-target genome edit in the clonal population of cells.

Item 38. The method of item 37, wherein the off-target genome edit comprises a deletion of endogenous DNA and/or an insertion of exogenous DNA at a site in the genome other than the target site.

Item 39. The method of any one of items 1 to 38, wherein the microfluidic device comprises a first portion having a substrate that has a dielectrophoresis (DEP) configuration and a second portion that has a substrate that has an electrowetting (EW) configuration, and wherein the sequestration pen is located in the first portion of the microfluidic device.

Item 40. The method of any one of items 1 to 38, wherein the microfluidic device comprises a first substrate having a dielectrophoresis (DEP) configuration and a second substrate having an electrowetting (EW) configuration, the first and second substrates connected via a bridging region, and wherein the sequestration pen is in a portion of the microfluidic device comprising the first substrate.

Item 41. The method of any one of items 1 to 40, wherein expanding the first cell into a clonal population of cells further comprises monitoring one or more characteristics of the cells of the clonal population for a period of time.

Item 42. The method of item 41, wherein the monitoring is performed periodically during the period of time.

Item 43. The method of item 41 or 42, wherein the monitoring comprises identifying changes in the size and/or morphology of the cells of the clonal population.

Item 44. The method of any one of items 41 to 43, wherein the monitoring comprises determining the rate of proliferation of the first cell into the clonal population of cells.

Item 45. The method of any one of items 41 to 44, wherein the monitoring comprises assessing the production of a protein of interest, the presence of one or more cell surface markers, and/or reaction with a specific antibody.

Item 46. A method of performing targeted genome editing within a microfluidic device, the method comprising:
selecting a first cell for genome editing;
positioning the first cell within an editing region of the microfluidic device; and
while the first cell is located within the editing region:
contacting the first cell with a genome editing biomolecule, the genome editing biomolecule configured to edit a genome of the first cell at a target site in the genome; and
allowing the genome editing biomolecule to edit the genome of the first cell at the target site.

Item 47. The method of item 46, wherein the genome editing biomolecule comprises an endonuclease.

Item 48. The method of item 46, wherein the genome editing biomolecule comprises a nucleic acid that encodes an endonuclease.

Item 49. The method of item 47 or 48, wherein the endonuclease is a programmable endonuclease.

Item 50. The method of item 49, wherein the programmable endonuclease is chosen from Cas9, Cpf1, and NgAgo.

Item 51. The method of any one of items 46 to 50, wherein the genome editing biomolecule comprises a targeting nucleic acid.

Item 52. The method of item 51, wherein the targeting nucleic acid comprises deoxyribonucleic acid (DNA).

Item 53. The method of item 51, wherein the targeting nucleic acid comprises ribonucleic acid (RNA).

Item 54. The method of item 51, wherein the genome editing biomolecule comprises one or more expression cassettes that encode the targeting nucleic acid and an endonuclease.

Item 55. The method of item 47 or 48, wherein the endonuclease comprises a TALEN protein or a zinc finger protein.

Item 56. The method of any one of items 46 or 48 to 54, wherein the genome editing biomolecule comprises a viral vector.

Item 57. The method of item 56, wherein the viral vector is a lentiviral vector.

Item 58. The method of item 57, wherein the lentiviral vector is integrase deficient.

Item 59. The method of item 56, wherein the viral vector is an adenoviral vector.

Item 60. The method of item 47 or 55, wherein the endonuclease is fused to a cell-penetrating peptide.

Item 61. The method of any one of items 46 to 60, wherein contacting the first cell with a genome editing biomolecule further comprises contacting the first cell with a donor template DNA.

Item 62. The method of item 61, wherein the genome editing biomolecule comprises the donor template DNA.

Item 63. The method of item 61, wherein the genome editing biomolecule and the donor template DNA are distinct molecules.

Item 64. The method of any one of items 61 to 63, wherein the donor template DNA comprises an insertion sequence, and wherein the insertion sequence optionally encodes a functional biomolecule, a barcode sequence, and/or a reporter molecule.

Item 65. The method of any one of items 46 to 64, wherein the step of contacting the first cell comprises permeabilizing the first cell.

Item 66. The method of item 65, wherein permeabilizing the first cell comprises electroporating or chemically permeabilizing the first cell.

Item 67. The method of any one of items 46 to 55 and 61 to 66, wherein the genome editing biomolecule is associated with a nanoparticle delivery vehicle or microstructure, and wherein contacting the first cell with a genome editing biomolecule comprises contacting the first cell with the nanoparticle delivery vehicle or microstructure.

Item 68. The method of any one of items 46 to 67, wherein the first cell is a mammalian cell.

Item 69. The method of item 68, wherein the first cell is a human cell, a rodent cell, a bovine cell, an ovine cell, a porcine cell, a canine cell, or a feline cell.

Item 70. The method of any one of items 46 to 69, wherein the first cell is an immunological cell.

Item 71. The method of item 70, wherein the immunological cell is chosen from a T cell, a B cell, an NK cell, a macrophage, or a precursor thereof Item 72. The method of any one of items 46 to 69, wherein the first cell is a stem cell.

Item 73. The method of item 72, wherein the stem cell is an embryonic stem cell, a mesenchymal stem cell, an umbilical vein mesenchymal stem cell, or an induced pluripotent stem cell (iPSC).

Item 74. The method of item 72, wherein the stem cell is a hematopoietic stem cell, an adipose-derived stem cell, a gingival stem cell, a renal stem cell, or a neural stem cell.

Item 75. The method of any one of items 46 to 69, wherein the first cell is a progenitor cell.

Item 76. The method of item 75, wherein the progenitor cell is an osteochondroprogenitor cell, a myofibroblast, a dermal fibroblast, or an endothelial progenitor cell.

Item 77. The method of any one of items 46 to 76, wherein the edit to the target site of the genome of the first cell comprises a deletion.

Item 78. The method of any one of items 46 to 77, wherein the edit to the target site of the genome of the first cell comprises an insertion of an exogenous nucleic acid sequence.

Item 79. The method of item 78, wherein the exogenous nucleic acid sequence comprises a nucleic acid sequence encoding a functional biomolecule, a barcode, and/or a reporter molecule.

Item 80. The method of any one of items 46 to 79, wherein at least one inner surface, or a portion thereof, of the microfluidic device is a conditioned surface.

Item 81. The method of item 80, wherein the microfluidic device comprises a sequestration pen, and wherein at least one inner surface of the sequestration pen is a conditioned surface.

Item 82. The method of item 80 or 81, wherein the conditioned surface comprises covalently-linked molecules, each having a linking group covalently bound to the at least one inner surface or the portion thereof and a moiety covalently bound to the linking group, wherein the moieties of the covalently-linked molecules provide a layer of organic and/or hydrophilic molecules suitable for maintenance and/or expansion of the genome-edited first cell.

Item 83. The method of item 82, wherein each moiety is a polymer comprising polyethylene glycol, saccharides, or amino acids.

Item 84. The method of item 82, wherein each moiety of a first subset of the covalently-linked molecules is a polymer that comprises amino acids, and wherein each moiety of a second subset of the covalently-linked molecules is a polymer that comprises polyethylene glycol or saccharides.

Item 85. The method of any one of items 1 to 45, wherein at least one inner surface of the sequestration pen is a conditioned surface.

Item 86. The method of item 85, wherein the conditioned surface comprises covalently-linked molecules, each having a linking group covalently bound to the at least one inner surface or the portion thereof and a moiety covalently bound to the linking group, wherein the moieties of the covalently-linked molecules provide a layer of organic and/or hydrophilic molecules suitable for maintenance and/or expansion of the genome-edited first cell.

Item 87. The method of item 86, wherein each moiety is a polymer comprising polyethylene glycol, saccharides, or amino acids.

Item 88. The method of item 86, wherein each moiety of a first subset of the covalently-linked molecules is a polymer that comprises amino acids, and wherein each moiety of a second subset of the covalently-linked molecules is a polymer that comprises polyethylene glycol or saccharides.

Item 89. The method of any one of items 1 to 45 or 85 to 88, wherein the microfluidic device comprises a plurality of sequestration pens, and wherein the method is performed on a plurality of cells to thereby generate a plurality of clonal populations of genetically modified cells.

Item 90. The method of item 89, wherein one or more steps of the method are performed on the plurality of cells in parallel.

Item 91. The method of any one of items 1 to 45 or 85 to 90, further comprising:
exporting one or more cells of a clonal population of genetically modified cells from the microfluidic device into a well plate, and
culturing the one or more exported cells in the well plate.

Item 92. A composition comprising a clonal population of genetically modified cells, wherein the clonal population was generated by any one of the methods of items 1 to 91.

Item 93. The composition of item 92 further comprising a plurality of clonal populations of genetically modified cells, wherein each clonal population was generated by any one of the methods of items 1 to 91.

Item 94. The composition of item 93, wherein the plurality of clonal populations together comprise at least 1000 genetically modified cells.

Item 95. The composition of item 93, wherein the plurality of clonal populations together comprise at least 10,000 genetically modified cells.

Item 96. The composition of any one of items 92 to 95 further comprising a pharmaceutically acceptable carrier.

Although specific embodiments and applications have been described in this specification, these embodiments and applications are exemplary only, and many variations are possible.

What is claimed is:

1. A method of generating a clonal population of genetically modified cells in a microfluidic device comprising a sequestration pen, the method comprising:
   maintaining a first cell in the sequestration pen of the microfluidic device, wherein the first cell has undergone a genome editing process;
   expanding the first cell into a clonal population of cells;
   detecting, in a first subset of the clonal population of cells, the presence of a first nucleic acid sequence by extracting nucleic acid from the first subset, wherein the first subset comprises one or more cells and the first nucleic acid sequence indicates the presence of an on-target genome edit in the clonal population of cells; and
   preserving a second subset of the clonal population of cells.

2. The method of claim 1, wherein the first cell is a mammalian cell.

3. The method of claim 1, wherein the first cell is a stem cell, a progenitor cell, or an immunological cell.

4. The method of claim 1, further comprising:
   contacting the first cell with a genome editing biomolecule; and
   introducing the first cell into the microfluidic device.

5. The method of claim 4, further comprising:
   contacting the first cell with a donor template nucleic acid molecule.

6. The method of claim 5, wherein the donor template nucleic acid molecule comprises all or part of the first nucleic acid sequence.

7. The method of claim 4, wherein the step of contacting the first cell with the genome editing biomolecule is performed prior to the step of introducing the first cell into the microfluidic device.

8. The method of claim 1, wherein the microfluidic device comprises a substrate having a DEP configuration, and
   wherein the method further comprises positioning the first cell in the sequestration pen using dielectrophoretic (DEP) force.

9. The method claim 1, wherein
   the extracted nucleic acid comprises genomic DNA.

10. The method of claim 9, further comprising:
    moving the first subset of cells out of the sequestration pen; and
    exporting the first subset of cells from the microfluidic device, wherein the nucleic acid is extracted outside of the microfluidic device.

11. The method of claim 9, further comprising:
    moving the first subset of cells out of the sequestration pen to a separate region within the microfluidic device, wherein the nucleic acid is extracted in the separate region.

12. The method of claim 9, further comprising amplifying the extracted nucleic acid.

13. The method of claim 1, wherein the on-target genome edit comprises a deletion of endogenous deoxyribonucleic acid (DNA) at a target site in the genome and/or an insertion of exogenous deoxyribonucleic acid (DNA) at the target site in the genome.

14. The method of claim 1, further comprising:
    detecting, in one of more cells of the clonal population, the presence of a second nucleic acid sequence, wherein the combination of the first nucleic acid sequence and the second nucleic acid sequence indicates the presence of the on-target genome edit in the clonal population of cells.

15. The method of claim 1, further comprising:
   detecting, in one of more cells of the clonal population of cells, the presence of an additional nucleic acid sequence, wherein the additional nucleic acid sequence indicates the presence of an off-target genome edit in the clonal population of cells.

16. The method of claim 1, wherein expanding the first cell into a clonal population of cells further comprises monitoring one or more characteristics of the cells of the clonal population for a period of time.

17. The method of claim 16, wherein the monitoring comprises assessing the production of a protein of interest, the presence of one or more cell surface markers, and/or reaction with a specific antibody.

18. A method of generating a clonal population of genetically modified cells in a microfluidic device comprising a sequestration pen, the method comprising:
   maintaining a first cell in the sequestration pen of the microfluidic device, wherein the first cell has undergone a genome editing process;
   expanding the first cell into a clonal population of cells; and
   detecting, in one or more cells of the clonal population, the presence of a first nucleic acid sequence,
   wherein at least one inner surface of the sequestration pen is a conditioned surface comprising covalently-linked molecules, each having a linking group (LG) covalently bound to the at least one inner surface and a moiety covalently bound to the linking group (LG) via a linker (L) having a linear backbone of 10 to 20 carbon atoms,
wherein the moieties of the covalently-linked molecules include amino acid-containing polymers suitable for maintenance and/or expansion of the genome-edited cell, and
   wherein the first nucleic acid sequence indicates the presence of an on-target genome edit in the clonal population of cells.

19. The method of claim 1, wherein the microfluidic device comprises a plurality of sequestration pens, and wherein the method is performed on a plurality of cells to thereby generate a plurality of clonal populations of genetically modified cells.

20. The method of claim 1, wherein the microfluidic device comprises an enclosure comprising:
   a flow region for containing a flow of a first fluidic medium; and
   the sequestration pen, wherein the sequestration pen comprises:
      an isolation region for containing a second fluidic medium, the isolation region having a single opening; and
      a connection region fluidically connecting the isolation region to the flow region;
   wherein the isolation region of the sequestration pen is an unswept region of the microfluidic device.

21. The method of claim 20, wherein the enclosure comprises a microfluidic channel, and at least a portion of the flow region is comprised by the microfluidic channel; and further wherein the connection region comprises a proximal opening into the microfluidic channel having a width $W_{con}$ ranging from about 20 microns to about 100 microns and a distal opening into said isolation region, and wherein a length $L_{con}$ of said connection region from the proximal opening to the distal opening is as least 1.0 times a width $W_{con}$ of the proximal opening of the connection region.

22. The method of claim 21, wherein the length $L_{con}$ of the connection region from the proximal opening to the distal opening is at least 1.5 times the width $W_{con}$ of the proximal opening of the connection region.

23. The method of claim 21, wherein the length $L_{con}$ of the connection region from the proximal opening to the distal opening is at least 2.0 times the width $W_{con}$ of the proximal opening of the connection region.

24. The method of claim 21, wherein the width $W_{con}$ of the proximal opening of the connection region ranges from about 20 microns to about 60 microns.

25. The method of claim 21, wherein (i) the length $L_{con}$ of the connection region from the proximal opening to the distal opening is between about 20 microns and about 500 microns; (ii) a width of the microfluidic channel at the proximal opening of the connection region is between about 50 microns and about 500 microns; and/or (iii) the proximal opening of the connection region is parallel to a direction of the flow of the first medium in the flow region.

26. The method of claim 21, wherein a height of the microfluidic channel at the proximal opening of the connection region is between 20 microns and 100 microns.

27. The method of claim 1, wherein the first cell is a human cell.

28. The method of claim 18, wherein the amino acid-containing polymers are extracellular matrix proteins.

29. The method of claim 18, wherein the moieties of the covalently-linked molecules include a mixture of polymers, the mixture further comprising polymers having alkylene oxide moieties.

30. The method of claim 18, wherein the moieties of the covalently linked molecules are covalently bound to the linker (L) via a coupling group (CG).

* * * * *

UNITED STATES PATENT AND TRADEMARK OFFICE
CERTIFICATE OF CORRECTION

| | |
|---|---|
| PATENT NO. | : 10,239,058 B2 |
| APPLICATION NO. | : 15/802174 |
| DATED | : March 26, 2019 |
| INVENTOR(S) | : Gregory G. Lavieu et al. |

It is certified that error appears in the above-identified patent and that said Letters Patent is hereby corrected as shown below:

In the Claims

Column 74, Claim 9, Line 40, "The method claim 1" should read --The method of claim 1--.

Signed and Sealed this
Second Day of July, 2019

Andrei Iancu
*Director of the United States Patent and Trademark Office*